US008119780B2

(12) United States Patent
Baker et al.

(10) Patent No.: US 8,119,780 B2
(45) Date of Patent: Feb. 21, 2012

(54) CHITOSAN-DERIVATIVE COMPOUNDS AND METHODS OF CONTROLLING MICROBIAL POPULATIONS

(75) Inventors: Shenda Baker, Upland, CA (US); William P. Wiesmann, Washington, DC (US); Shannon Ryan, Claremont, CA (US)

(73) Assignee: Synedgen, Inc., Claremont, CA (US)

( * ) Notice: Subject to any disclaimer, the term of this patent is extended or adjusted under 35 U.S.C. 154(b) by 0 days.

(21) Appl. No.: 11/657,382

(22) Filed: Jan. 24, 2007

(65) Prior Publication Data

US 2007/0281904 A1 Dec. 6, 2007

Related U.S. Application Data

(60) Provisional application No. 60/810,591, filed on Jun. 2, 2006, provisional application No. 60/838,780, filed on Aug. 18, 2006.

(51) Int. Cl.
*C08B 37/08* (2006.01)
*A01N 43/04* (2006.01)

(52) U.S. Cl. ............................................ 536/20; 514/55

(58) Field of Classification Search .................. None
See application file for complete search history.

(56) References Cited

U.S. PATENT DOCUMENTS

| | | | |
|---|---|---|---|
| 3,879,376 A | 4/1975 | Vanlerberghe et al. |
| 4,394,373 A | 7/1983 | Malette et al. |
| 4,532,134 A | 7/1985 | Malette et al. |
| 4,542,014 A | 9/1985 | Bresak et al. |
| 4,744,933 A | 5/1988 | Rha et al. |
| 4,749,620 A | 6/1988 | Rha et al. |
| 4,772,689 A | 9/1988 | Lang et al. |
| 4,822,598 A | 4/1989 | Lang et al. |
| 4,908,404 A | 3/1990 | Benedict et al. |
| 4,921,949 A | 5/1990 | Lang et al. |
| 4,957,908 A | 9/1990 | Nelson |
| 4,976,952 A | 12/1990 | Lang et al. |
| 5,015,632 A | 5/1991 | Nelson |
| 5,300,494 A | 4/1994 | Brode, II et al. |
| 5,510,102 A | 4/1996 | Cochrum |
| 5,538,955 A | 7/1996 | De Rosa et al. |
| 5,614,204 A | 3/1997 | Cochrum |
| 5,637,681 A | 6/1997 | Stockel |
| 5,730,876 A | 3/1998 | You et al. |
| 6,162,241 A | 12/2000 | Coury et al. |
| 6,465,626 B1 | 10/2002 | Watts et al. |
| 6,521,268 B2 | 2/2003 | You et al. |
| 6,696,261 B2 | 2/2004 | Patel et al. |
| 6,844,430 B2 | 1/2005 | Pesce et al. |
| 6,896,809 B2 | 5/2005 | Qian et al. |
| 6,958,325 B2 | 10/2005 | Domb |
| 7,053,068 B2 | 5/2006 | Prinz |
| 2001/0036934 A1 | 11/2001 | Hwang et al. |
| 2002/0150585 A1 | 10/2002 | Marciani |
| 2003/0147860 A1 | 8/2003 | Marchosky |
| 2003/0181416 A1 | 9/2003 | Comper |
| 2004/0028672 A1 | 2/2004 | Bjorck et al. |
| 2004/0103821 A1 | 6/2004 | Shobu et al. |
| 2004/0104020 A1 | 6/2004 | Davidson et al. |
| 2005/0800245 | 4/2005 | Hung et al. |
| 2006/0198786 A1 | 9/2006 | Wei et al. |
| 2008/0200948 A1 | 8/2008 | Utecht et al. |
| 2008/0207561 A1 | 8/2008 | Utecht et al. |
| 2008/0318868 A1 | 12/2008 | Bercovier et al. |
| 2009/0074824 A1 | 3/2009 | Vila Pena et al. |
| 2009/0075383 A1 | 3/2009 | Buschmann et al. |

FOREIGN PATENT DOCUMENTS

| | | |
|---|---|---|
| CA | 2126132 | 12/1995 |
| CN | 1519035 | 8/2004 |
| CN | 1587282 | 3/2005 |
| CN | 1587283 | 3/2005 |
| CN | 1701849 | 11/2005 |
| CN | 101239041 | 8/2008 |
| CN | 101285060 | 10/2008 |
| EP | 0319645 A1 | 6/1989 |
| EP | 1880738 | 1/2008 |
| FR | 2306997 A1 | 11/1976 |
| JP | 60233102 | 11/1985 |
| JP | 60233102 A1 | 11/1985 |
| JP | 10139889 | 5/1998 |
| JP | 10175857 | 6/1998 |
| JP | 2000302803 | 10/2000 |
| JP | 2003277401 | 10/2003 |
| JP | 2005247700 | 9/2005 |
| KR | 2002008436 | 1/2002 |
| KR | 20020037241 | 5/2002 |
| KR | 2003025023 | 3/2003 |
| KR | 2005082020 | 8/2005 |
| KR | 2007050586 | 5/2007 |

(Continued)

OTHER PUBLICATIONS

Vikhoreva. Carbohydrate Polymers 62 (2005) 327-332.*
Kagurai et al. JP 60-233102, translation.*
Anderson et al.; Intracellular bacterial biofilm-like pods in urinary tract infections. Science 301:105(2003).
Aronson et al.; In Harm's Way: Infections in Deployed American Military Forces; Clinical Inf. Disease vol. 43: 1045-1051(2006).
Avadi et al.; Dimethylmethyl chitosan as an antimicrobial agent: synthesis, characterization and antibacterial effects; Eur. Polymer J. 40, 1355-1361 (2004).
Dale et al.; Therapeutic Efficacy of "Nubiotics" against Burn Wound Infection by *Pseudomonas aeruginosa*; Antimicrobial Agents and Chemotherapy; pp. 2918-2923, 48:8 (2004).

(Continued)

*Primary Examiner* — Layla Bland
(74) *Attorney, Agent, or Firm* — Lando & Anastasi LLP

(57) ABSTRACT

The present invention is directed to chitosan-derivative compounds and structures, methods of making chitosan-derivative compounds and methods for controlling, inhibiting and enhancing microbial populations in a variety of environments. The present invention is also directed to the control, inhibition and enhancement of microbial populations in animals, particularly humans. The microbial populations include bacteria, viruses and other pathogens where control of microbial populations are a necessity. The chitosan-derivative compounds of the present invention include chitosan-arginine compounds, related chitosan-L/D unnatural amino acid compounds, chitosan-acid amine compounds, chitosan-L/D natural amino acid derivative compounds, co-derivatives of the chitosan-derivative compounds, salts of the chitosan derivative compounds, and chitosan-guanidine compounds.

12 Claims, 25 Drawing Sheets

FOREIGN PATENT DOCUMENTS

| | | |
|---|---|---|
| KR | 2008006242 | 1/2008 |
| WO | 9811903 | 3/1998 |
| WO | 03011912 A1 | 2/2003 |
| WO | 2004029096 | 4/2004 |
| WO | 2004041118 A2 | 5/2004 |
| WO | 2006029519 A1 | 3/2006 |
| WO | 2007028244 A1 | 3/2007 |
| WO | 2008042891 | 4/2008 |
| WO | 2008095586 | 8/2008 |
| WO | 2008095587 | 8/2008 |
| WO | 2008095588 | 8/2008 |

OTHER PUBLICATIONS

Davies; Understanding biofilm resistance to antibacterial agents; Nature Reviews Drug Discovery 2:114 (2003).

Hamman et al.; Effect of the type of base and number of reaction steps on the degree of quaternization and molecular weight of N-trimethyl chitosan chloride; Drug Dev. And Ind. Pharm 27(5), 373-380 (2001).

Ho et al.; Preparation and characterization of RGD-immobilized chitosan scaffolds; Biomaterials 26: 3197-3206 (2005).

Jeon et al.; Effect of antimicrobial activity by Chitosan oligosaccharide N-conjugated with Asparagine. Journal of Microbiology and Biotechnology., 11(2): 281-286 (2001).

Kim et al.; Synthesis of chitosan derivatives with quaternary ammonium salt and their antibacterial activity, Polymer Bulletin. 38, 387-393 (1997).

Klokkevold et al.; Effect of chitosan on lingual hemostasis in rabbits; J. Oral and Maxillofacial Surg. 49(8): 858-863 (1991).

Lim et al.; Review of chitosan and its derivatives as antimicrobial agents and their uses as textile chemicals, J. of Macromolecular Sci. C43(2), 223-269 (2003).

Liu et al. ; A chitosan-arginine conjugate as a novel anticoagulation biomaterial. J. of Materials Science: Materials in Medicine 15:1199-1203 (2004).

Liu et al.; Antibacterial action of chitosan and carboxymethylated chitosan; J. Appl. Poly. Sci. 79, 1324-1335 (2001).

Liu, H. et al., Chitosan kills bacteria through cell membrane damage. Internat. J of Food Microbio 95, 147-155 (2004).

Luppens et al.; Development of a standard test to assess the resistance of *Staphylococcus aureus* biofilm cells to disinfectants; Applied & Environmental Microbiology 68:4194 (2002).

Marreco et al.; Effects of different sterilization methods on the morphology, mechanical properties and cytotoxicity of chitosan membranes used as wound dressings, Wiley periodicals, 268-277(2004).

Maryanoff et al.; A convenient synthesis of guanidines from thioureas; J. Org. Chem. 51, 1882-1884 (1986).

Masuko, et al.; Chitosan-RGDSGGC conjugate as a scaffold material for musculoskeletal tissue engineering; Biomaterials 26: 5339-5347 (2005).

Mi et al.; Asymettric chitosan membranes prepared by dry/wet phase separation: a new type of wound dressing for controlled antibacterial release; J. Membrane Sci.; pp. 212, 237-254 (2003).

Moller et al.; Antimicrobial and physicochemical properties of Chitosan-HPMC-based films; J. Agric. Food. Chem. 52, 6585-6591 (2004).

Muzzarelli et al.; N-(carboxymethylidene) chitosan and N-(carboxymethyl) chitosan: novel chelating polyampholytes obtained from chitosan glyoxylate. Carbohyd. Res. 107, 199-214, (1982).

Muzzarelli et al.; Fungistatic activity of modified chitosan against *Saprolegnia parasitica*; Biomacromolecules, 2, 165-169 (2001).

O'Toole et al.; Biofilm formation as microbial development; Annual Review of Microbiology 54:49 (2000).

Putnam et al.; Antimicrobial Agents and Chemotherapy; pp. 2571-2572 49:6 (2005).

Qin et al.; Water-solubility of chitosan and its antimicrobial activity. Carbohydrate Polymers; 63: 367-374 (2006).

Rabea al.; Chitosan as antimicrobial agent: applications and mode of action; Biomacromolecules 4(6), 1457-1465 (2003).

Sashiwa et al.; Chemical modification of chitin and chitosan 2: preparation and water soluble property of N-acylated or N-alkylated partially deacetylated chitins Carbohydrate Polymers 39, 127-138 (1999).

Shima et al.; Antimicrobial action of epsilon-poly-L-lysine. J. Antibiot; 37:1449-1455 (1984).

Shin et al.; Molecular weight effect on antimicrobial activity of chitosan treated cotton fabrics; J. Appl. Poly Sci., 80, 2495-2501 (2001).

Sieval et al.; Preparation and NMR characterization of highly substituted N-trimethyl chitosan chloride; Carbohydrate Polymers 16, 157-165 (1998).

Stoodley et al.; Biofilms as Complex Differentiated Communities; Annual Review of Microbiology; 56:187 (2002).

Viljanen et al.; Effect of small cationic leukocyte peptides (defensins) on the permeability barrier of the outer membrane; Infect. Immun. September; 56(9): 2324-2329 (1988).

Watnick et al.; Biofilm city of microbes; Journal of Bacteriology 182:2675 (2000).

Zia et al.; Synthesis and antibacterial activity of quaternary ammonium salt of chitosan; Carbohydrate Res. 333, 1-6 (2001).

Bernatowicz et al.; 1H-pyrazole-1-carboxamidine hydrochloride: an attractive reagent for guanylation of amines and its application to peptide synthesis; J. Org. Chem. 57, 2497-2502 (1992).

Jia et al.; Synthesis and antibacterial activity of quaternary ammonium salt of chitosan; Carbohydrate Res. 333, 1-6 (2001).

Katritzky et al.; Recent developments in guanylating agents; ARKIVOC iv, 49-87 (2005).

Tsai et al.; Antibacterial Activity of Shrimp Chitosan against *Escherichia coli*; J. of Food Protection 62(3); pp. 239-243 (1999).

Yalpani, M. et al.; Antimicrobial Activity of Some Chitosan Derivatives pp. 543-548 in C. Brine et al. (Ed.), Advances in Chitin and Chitosan (1992).

Elsegood et al. "Binding and uptake of chylomicron remnants by primary and THP-1 human monocyte-derived macrophages: determination of binding proteins" Clin Sci (Lond). Aug. 2001; 101(2): 111-9.

Eperon et al. "The use of human monocytoid lines as indicators of endotoxin" J. Immunol Methods, Aug. 14, 1996; 194(2): 121-9.

Limulus Amebocyte Lysate (LAL test), Associates of Cape Cod Inc., E. Falmouth, MA Nov. 2003.

Moesby et al., "A comparative study of Mono Mac 6 cells, isolated mononuclear cells and Limulus amoebocyte lysate assay in pyrogen testing", Int. J. Pharm., Nov. 30, 1999; 191(2): 141-9.

Opal et al., "Anti-Inflammatory cytokines" Chest., Apr. 2000; 117(4): 1162-72.

Poole et al., "A rapid "one-plate" in vitro test for pyrogens" J. Immol. Methods, Mar. 1, 2003;274(1-2):209-20.

Reisman et al., "Modulation of interleukin-1 secretion by immunosupressive drugs, alone and in combination" Transplant Immunology, Mar. 3, 1995(1);45-9.

Taktak et al., "Assay of Pyrogens by interleukin-6 release from monocytic cell lines" J. Pharm. Pharmacol.; Aug. 1991 43(8): 578-82.

International Search Report for related application PCT/US2007/023850, dated Dec. 8, 2008.

Cárdenas et al., "Synthesis and characterization of carboxymethyl chitosan-arg and carboxymethyl chitosan-lys derivatives," Journal of the Chilean Chemical Society, 2004, vol. 49, No. 3, pp. 237-240.

Zhang et al., "Synthesis and antimicrobial activity of polymeric guanidine and biguanidine salts," Polymer, Oct. 1999, vol. 40, No. 2, pp. 6189-6198, Elsevier Science Publishers B.V, GB.

International Search Report from International Application No. PCT/US2007/002078 dated Feb. 4, 2008.

* cited by examiner

Modified chitosan inhibits a wide range of viruses

Figure 10

CHITOSAN-DERIVATIVE COMPOUNDS AND METHODS OF CONTROLLING MICROBIAL POPULATIONS

This application obtains priority from provisional application 60/810,591 filed Jun. 2, 2006 and from provisional application 60/838,780 filed Aug. 18, 2006

STATEMENT OF GOVERNMENT INTEREST

As outlined under 37 CFR 401.14(b), the United States government shall have a nonexclusive, nontransferable, irrevocable, paid-up license to practice or have practiced for or on behalf of the United States the subject invention.

BACKGROUND OF THE INVENTION

The understanding of the role of natural polysaccharides in controlling microbial populations by selective enhancement or inhibition is emerging. The field of biopolymers has evolved significantly due to the versatility of their applications and the greater understanding of their function in many natural symbiotic processes. This development is particularly true for chitosan, a polysaccharide which is naturally abundant and has been successfully utilized in diverse areas of agriculture, wastewater treatment, food technology, animal food stock, paper/textile manufacture, biotechnology and biomedical devices and products.

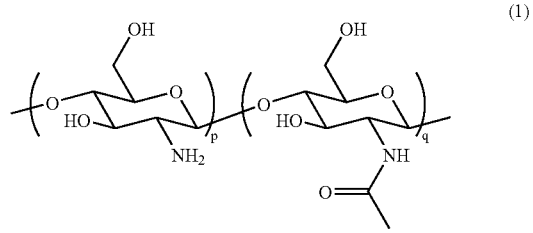

(1)

Chitin, a polymer of N-acetyglucosamine, is a cellulose-like biopolymer that is the main component of crustaceans (e.g. shrimp, crab, lobster) and is also present in the exoskeleton and the cell wall of fungi, insects and yeast. Chitosan, a principle derivative of chitin, is formed from chitin by deacetylation in the presence of alkali. It is the mostly deacetylated form of the naturally occurring polysaccharide chitin. The process of removing the acetyl group from poly-β(1→4)-N-acetyl-D-glucosamine to poly-β(1→4)-D-glucosamine causes the formation of primary amines. Chitosan is not a single polymeric molecule, but a class of molecules having different molecular weights and different degrees of deacetylation. The structure of chitosan and chitin is shown in (1), where p and q are the fractional relationship of the monomers glucosamine and N-acetyl glucosamine, respectively, and are between 0 and 1. The sum p+q=1. For chitin, q->1 and the molecule is nearly fully acetylated. Molecules where q<0.5 are considered chitosan. A key feature of chitosan is the positive charge of its amino group (—$NH_3^+$) when pH is below its pKa (~6.3). When the pH=pKa, 50% of the amines are positive. The fraction of amines that are positive increases exponentially as the pH decreases and decreases exponentially as the pH increases, by the Henderson-Hasselbach equation $$pH = pK_a + \log\frac{[NH_2]}{[NH_3^+]}.$$

At lower pH, native chitosan forms a polycationic structure that can interact with anionic compounds and macromolecular structures. While very low molecular weight chitosans with high degree of deacetylation are soluble at physiological conditions, most chitosans lack positive charge and are only soluble in acidic conditions. For example, chitosan is highly soluble in aqueous acetic acid.

Chitosan has numerous biological properties, including antimicrobial activity, hemostatic activity, acceleration of wound healing, tissue-engineering scaffolds, drug delivery, and antitumor activity. Additionally, chitosan, when biological burden is removed, is biodegradable and biocompatible with low toxicity to mammalian cells. It is also important to note that bacteria generally should not develop chitosan resistance.

Chitosan's unique biological properties make it medically important. Consequently, chitosan has been developed for a variety of applications using these properties such as biodegradability, non-toxicity and antibacterial activity against a broad spectrum of microorganisms. However, the use of chitosan is limited because of its insolubility at neutral and physiological pH. The present invention overcomes the limitations of the prior applications and methodologies of making and using chitosan, as discussed below.

It is well known that biopolymers that are natural polycations have a tendency to be antimicrobial. Defensins, for example, are small cationic polypeptides with antibacterial properties that are produced naturally by the human body. See Viljanen et al.; *Effect of small cationic leukocyte peptides (defensins) on the permeability barrier of the outer membrane*; Infect. Immun. September; 56(9): 2324-2329 (1988). Efforts to reproduce the effectiveness of natural polycations as antibacterials with limited toxicity have been met by limited success. The complexity of understanding the antibacterial properties results from the multiplicity of interactions required between the polycation and the bacteria. Some of the important factors that influence the antibacterial properties include degree of charge, distribution of charge, molecular weight, degree of hydrophobicity and placement of the charge relative to the polymer backbone. The magnitude of this latter effect is easily conceptualized from the experiments comparing poly-ε-lysine vs poly-α-lysine. See Shima et al.; *Antimicrobial action of epsilon-poly-L-lysine*. J. Antibiot; 37:1449-1455 (1984). Poly-ε-lysine has the positive charges located on the α-amine in close proximity to the linear polymer backbone. Poly-α-lysine has the positive charges located five bond lengths from the linear polymer backbone. Poly-ε-lysine was more active as an antibacterial than poly-α-lysine against 20 of 22 tested bacterial species. They also determined an optimal molecular weight. Additionally, they showed the importance of the positive charge by removing the effective amine by reaction with a variety of carboxylic acids with no positive charge. Furthermore, they showed that small oligomers of poly-ε-lysine interfered with protein synthesis in *E. coli* more than poly-α-lysine. These results suggest a complicated interplay between charge, molecular weight, and charge placement on antibacterial effectiveness.

Nonfunctionalized Chitosan and Salts

While several mechanisms have been proposed for chitosan's antimicrobial activity, the exact mechanism is still unclear. The currently accepted antimicrobial mechanism is based on the interaction of the positively charged chitosan with the negatively charged residues on bacterial cell surface. It is believed that this charge interaction alters bacterial surface morphology and either damages the membrane to induce membrane permeability that causes leakage of intracellular substances (e.g. electrolytes, proteins, nucleic acids, glucose, and lactate dehydrogenase), or develops an impermeable layer around the cell and prevents nutrients from entering the bacteria. Another proposed mechanism suggests that positively charged chitosan interacts with cellular DNA through chitosan penetration into the cells, consequently acting as a barrier to RNA and protein synthesis.

Chitosan or chitosan derivatives that are described with antibacterial activity are considered to be bacteriocidal or bacteriostatic, often with little distinction between the two mechanisms. A bacteriocidal material kills the live bacteria or some fraction therein. A bacteriostatic material hinders the growth of bacteria or some fraction therein but does not imply whether or not bacteria are killed or their growth inhibited.

Chitosan's antimicrobial activity is affected by several factors such as source of chitosan, molecular weight (MW), degree of deacetylation (DD), chitosan concentration, pH, temperature, solution cations and polyanions, bacterial species and the phase of bacterial growth. A variety of studies have demonstrated the need for positively charged or other soluble chitosans in attempts to address the mechanism of activity. See Muzzarelli et al.; *N-(carboxymethylidene) chitosan and N-(carboxymethyl) chitosan: novel chelating polyampholytes obtained from chitosan glyoxylate*. Carbohyd. Res. 107, 199-214, (1982); and Moller et al.; *Antimicrobial and physicochemical properties of Chitosan-HPMC-based films*; J. Agric. Food. Chem. 52, 6585-6591 (2004).

Studies on the mechanism of bactericidal activity of chitosan acetate suggest that cell membranes of *Escherichia coli* and *Staphylococcus aureus* are damaged by the chitosan and become permeable, likely a result of the electrostatic interactions between the positive amines on the chitosan and the negative phosphoryl groups of the phospholipids comprising the cell membrane. See Liu, H. et al., *Chitosan kills bacteria through cell membrane damage*. Internat. J of Food Microbio 95, 147-155 (2004). Another reference discloses the use of O-carboxymethylated and N,O-carboxymethylated chitosans as antibacterials due to the compounds' ability to bind to DNA and the subsequent inhibition of DNA transcription. See Liu et al.; *Antibacterial action of chitosan and carboxymethylated chitosan*; J. Appl. Poly. Sci. 79, 1324-1335 (2001). Another reference discloses a comprehensive survey of the proposed mechanisms of antimicrobial activity including antifungal, antibacterial and antiviral properties (highlighting the influence of MW, pH, polynucleotide binding, cell permeability, binding of essential minerals by chitosan, and its limitations above pH 6.5). See Ravbea et al.; *Chitosan as antimicrobial agent application and mode of action*; Biomacromolecules 4(6), 1457-1465 (2003). Yet another reference discloses that water soluble chitins and chitosans without sufficient positive charge or MW are not antibacterial, whereas insoluble, high MW chitosans are effective if placed in acidic media, again suggesting that positive charge plays a role in mediating bacteriocide. See Qin et al.; *Water-solubility of chitosan and its antimicrobial activity*. Carbohydrate Polymers; 63: 367-374 (2006).

A careful study using temperature and a variety of pH's showed the dramatic effect of the degree of protonation, ie positive charge, on the antibacterial activity of chitosan against *E. coli*. For pH's between 5 and 9, they showed a dramatic and continual increase in cell death as the pH increased, with nearly no activity at pH 9. See Tsai et al.; *Antibacterial Activity of Shrimp Chitosan against Escherichia coli*; J. of Food Protection 62(3); pp. 239-243 (1999).

Several patents disclose applications of nonfunctionalized chitosan for absorbent materials, drug delivery, biocompatible/bioabsorbable materials, hemostatic agents, filters, textiles, crosslinked gels, as a carrier for soluble or active antibacterial and antimicrobial agents, as a chelating and flocculation method for metals in water, as biodegradable and/or edible films, shellacs and sheets, as well as an odor control agent, hydrophilic absorbent and biodegradable/biocompatible structural support for co-derived scaffolds. Chitosan is broadly represented in the patent and academic literature in the insoluble form.

Chitosan of significant MW is insoluble at physiological pH. However these references differ from the present invention by disclosing soluble chitosan compounds formed by intentional breakdown of molecular weight. U.S. Pat. No. 5,730,876 to You et. al discloses a method for fractionating low molecular weight, soluble chitosans through reaction with enzymes and acid and subsequent ultrasonic membrane filtration to bring the MW from over 100 kDa to 10,000 kDa or less. Reducing molecular weight is a common way to improve solubility of chitosan, but it does nothing to increase the positive charge on the polysaccharide. Patents disclosing the production of water soluble chitosans teach the desirability of formulations that are soluble at pH 7. In order to make such chitosans that are not derivatized, the molecular weight must be decreased dramatically, the degree of deacetylation high (depending on the MW) and may or may not have antibacterial effects, depending on the composition of the additives. For example, U.S. Pat. No. 4,532,134 to Malette et al. discloses a water-soluble chitosan that is used to treat wounds as a hemostatic agent. These low MW, low positive charge nonfunctionalized chitosans are not related to the current application.

Chitosan Mixtures (Compositions)

Many of the prior art references disclose the uses of mixtures of chitosan and atoms, chemicals (natural or synthetic), polymers or polypeptides which impart new properties to the entire composition including antibacterial or antimicrobial properties. Mixtures are a homogenous (same phase) or heterogeneous (different phases) composition of chitosan and any small molecule, polymeric molecule, or any form of solvent, stabilizing agent, or polyion. Chemically, physically, and functionally, heterogenous and homogeneous mixtures are not identical to single molecule comprised of components of the mixture.

For example, a number of patents discuss mixtures comprised of chitosan and these other agents, but do not constitute a compound or molecule. For example, US patent application publication US/2004/0104020 A1 to Davidson et al. discloses chitosan compositions for hair care, odor control, blood management, fabric treatment, plant care, water purification and drug delivery using a network of nano-sized fibers. This reference is not directed to antibacterials but is directed to the broad uses of chitosan and the mixtures of chitosan. This serves as one example of any number of nonfunctionalized chitosan compositions reflecting its broad usage independent of or including antimicrobial properties.

The prior art also discloses polycations that are useful in a number of broad formulations with or without chitosan. Chitosan and arginine or lysine, positively charged amino acids, or polymeric combinations of poly-arginine or poly-lysine, usually in the L stereo isomer, of the same often appear simultaneously on these lists as cationic biopolymers, but are used independently and not dependent on the combined properties for functionality. Examples of these include the following. U.S. Pat. No. 5,614,204 to Cochrum discloses "selective vascular embolization" utilizing an occlusion agent that may be alginate, chitosan or poly-L-amino acid. Poly L-amino acids include poly-L-lysine, poly-L-arginine, poly-L-glutamic acid, poly-L-histidine, poly-α-D-glutamic acid or a mixture of the above. As a mixture and as an occluding agent, the components of this composition teach away from the applications and activities and compounds of our application. See also U.S. Pat. No. 5,510,102 to Cochrum. U.S. Pat. No. 4,749,620 to Rha et al discloses microencapsulation including chitosan as a polymer selected from a group consisting of chitosan and poly-L-lysine. See also U.S. Pat. No. 4,744,933 to Rha et al. The utility and composition of the above references teach away from the present invention as discussed below. Japanese Patent 10175857 to Sekisui Chem. Co. Ltd. discloses a healing agent comprising a commercial ointment with a carbohydrate that is a mixture of positive material in a hydrocarbon base. This reference is directed to the addition of arginine, glutamate and their derivatives to the ointment, followed by the same commercial ointment with the addition of chitin, chitosan and their derivatives to ointment. Mutual benefit is not noted. US 2004/0103821 A1 to Shobu, et al., discloses a food and/or medicament coating of an insoluble shellac comprising a basic amino acid (e.g. arginine) and/or chitosan. This reference is however directed to an insoluble mixture.

Interestingly, chitosan and the positively charged amino acids appear in the patent literature not in combination, but due to their similar constituency as positively charged polycations in groups where they co-reside. See, for example, US Patent Publication US 2004/0028672 to Bjorck, et al. which discloses methods for identifying agents including L-arginine and chitosan, for treating chronic and acute microbial infections. This patent discloses polycations that may be screened for antimicrobial activity. Additionally, this reference is directed to only homopolymers of arginine or chitosan individually.

Chitosan and Antivirals or Antibacterials

Because chitosan is often used as a drug carrier, much of the patent literature teaches to the adhesive and biocompatible properties of chitosan and of chitosan's role as a component in compositions that contain antiviral or antibacterial active agents. For example, U.S. Pat. No. 6,465,626 October 2002 to Watts et al teaches that chitosan is one of many adhesive materials that can be used in pharmaceutical applications. The antiviral component is an agent ICAM-1.

Similarly, other patents teach to mixtures of low molecular weight chitosans that are soluble, but in compositions that antimicrobial activity only in the presence of another molecule, an active antimicrobial agent. For example, U.S. Pat. No. 5,730,876 You et al. teaches separation and purification of low molecular weight chitosan using multi-step membrane separation process and only claims antibacterial properties in the presence of elecampane (Inula Helenium L.) root extract. The active antimicrobial agent is the elecampane. Further, the teachings of U.S. Pat. No. 6,521,268 to You et al., disclose a "natural cell carrier" of water-soluble chitosan and elecampane extract—antibacterial, anti-inflammatory and broad antibacterial spectrum for food, cosmetics and medicine, and discusses the antibacterial mechanism as chitosan binding to telechoic acid in all bacterial membranes. It is the carrier, but also adjuvant to the true antibiotic and inflammatory elecampane. This patent teaches the role of chitosan in binding a cell membrane which supports the need for a water-soluble chitosan, but limits the membrane association to a telechoic acid. The patent teaches away from a high molecular weight antibacterial chitosan derivative.

Chitosan Salts

Chitosan can be prepared in an acidic solution and precipitated with active salts. For example, U.S. Pat. No. 4,957,908 to Nelson teaches that chitosan salts can be useful to help impart desirable properties, in this case for antimicrobial activity that does not adsorb quickly into the skin and can be used for dermatological items such as soaps and shampoos. Zinc and sodium pyrithione are used as antifungals and antibacterials, but absorb into the skin. By making a particular salt of the chitosan, they can make chitosan pyrithione that is as effective as their original material but dissolves more slowly. Similarly, U.S. Pat. No. 5,015,632 to Nelson discloses a salt of chitosan that is to provide slow release of an anionic salt, pyrithione, from films. It is used as an antimicrobial agent in dermatological items, but derives its properties from the pyrithione. This chitosan salt has the same antibacterial efficacy as the sodium salt of the same anion and thus teaches away from the present invention. U.S. Pat. No. 5,300,494 to Brode II et al. disclose a series of chitosan salts (in particular lactate salts) that act as carrier films for pharmaceutically active drugs (particularly quaternary ammonia compounds and salts). As thin films that retain moisture and the ability to retain and slowly deliver a drug, in this case an antiviral. These serve as examples of any chitosan salts that bear antimicrobial capacity due to the anionic salt, a salt mixture with an antibacterial salt rather than as the free compound.

U.S. Pat. No. 6,844,430 B2 to Pesce et al. disclose the use of aminopolysaccharide salts for the control of odor in sanitary products, diapers et al. and where a preferred saccharide is chitosan. The chitosan is prepared with a number of salts including the amino acids such as arginine and lysine. As salts, they are counterions and not part of the molecule but produce the desired biocompatibility. This example teaches to the ability to use salts to provide additional activity in a chitosan formulation, but does not teach the present invention.

Chitosan Derivatives

Interest has developed over the years in controlling the properties of chitosan by performing chemical modifications on the polymer backbone. For chemical reactions that retain the polymeric form of the chitosan, there are only two types of fairly highly reactive moieties on the monomers: the hydroxyl group and the amine group. The two hydroxyl groups have slightly different reactivity but can be functionalized by hydroxy active agents at high pH on either the acetylated or deacetylated monomers of the chitosan. The primary amine of the deacetylated monomer of the chitosan is available for reaction at moderate pH above 6 or so where a significant number of the amines are deprotonated. These chemistries provide new chitosan compounds bearing different properties from the original chitosan polymer.

Hydroxide Chemistry

Other patents teach the desirability of functionalization of chitosans to achieve particular goals. For example, US Patent Publication US 2003/0181416 A1 to Comper, discloses primarily Dextran which when sulfonated is effective in vivo in the treatment or prevention of viral, bacterial and parasitic infections. This reference teaches that many other polysaccharides are not antimicrobial or antiviral and teaches the desirability of controlling the molecular weight of polysaccharides for optimal in vivo and in vitro microbial activity. This reference also teaches the desirability of controlling the pH to improve deliverability of the active ingredients. The sulfated polysaccharides include two chitosan derivatives where the antimicrobial properties are imparted by negatively charged sulfates.

Carboxyalkylated chitosan derivatives, sulfonyl chitosan derivative, carbohydrate-branched chitosan derivatives, chitosan-iodine complexes and other miscellaneous derivatives were also developed. See Muzzarelli et al.; *N-(carboxymethylidene) chitosan and N-(carboxymethyl) chitosan: novel chelating polyampholytes obtained from chitosan glyoxylate.* Carbohyd. Res. 107, 199-214 (1982); Chen et al.; *Antimicrobial effect and physical properties of sulfonated chitosan*; Advances in Chitin Science, Vol III, 278-282 (1998); Yalpani et al.; *Antimicrobial activity of some chitosan derivatives*, Advances in chitin and chitosan; 543-548 (1992); U.S. Pat. No. 5,538,955 to De Rosa et al (1996); and Muzzarelli et al.; *Fungistatic activity of modified chitosan against Saprolegnia parasitica*; Biomacromolecules, 2, 165-169 (2001). The limited application and range of these derivatives teach to the need for more thoughtful application of chemical knowledge to the control of solubility and antibacterial properties.

Amine Chemistry-quaternization

The primary amine on the glucosamine monomer of chitosan can be the basis for a number of reactions, the most important in the literature being quaternization. To quaternize the amine on chitosan, three additional groups must be added, taking the primary amine to a quaternary amine with a permanent positive charge. A quaternary amine is fairly electrophilic, but can remain stable in the absence of any available nucleophiles. Many of these derivatives add functional groups or modify the carbohydrate with non-biological moieties that render the molecule different than any naturally occurring molecule, and thus the toxicity of the molecule is unknown.

Much of chitosan chemistry has centered on the reactive amine that results from the deacetylation process of chitin. A quaternized chitosan derivative was developed by introducing quaternary ammonium salts onto the chitosan backbone. See Kim et al.; *Synthesis of chitosan derivatives with quaternary ammonium salt and their antibacterial activity*, Polymer Bulletin. 38, 387-393 (1997) and Zia et al.; *Synthesis and antibacterial activity of quaternary ammonium salt of chitosan*; Carbohydrate Res. 333, 1-6 (2001). The antibacterial activity and water solubility of this derivative was increased with the decrease in the chain length of alkyl substituent. Although there are other methods for producing and analyzing quaternized amines on chitosan, a sampling of methods is presented. See Hamman et al.; *Effect of the type of base and number of reaction steps on the degree of quaternization and molecular weight of N-trimethyl chitosan chloride*; Drug Dev. And Ind. Pharm 27(5), 373-380 (2001); Avadi et al.; *Dimethylmethyl chitosan as an antimicrobial agent: synthesis, characterization and antibacterial effects*; Eur. Polymer J. 40, 1355-1361 (2004); Sashiwa et al.; *Chemical modification of chitin and chitosan 2: preparation and water soluble property of N-acylated or N-alkylated partially deacetylated chitins* Carbohydrate Polymers 39, 127-138 (1999); and Sieval et al.; *Preparation and NMR characterization of highly substituted N-trimethyl chitosan chloride*; Carbohydrate Polymers 16, 157-165 (1998). The quaternary amine has its positive charge surrounded by bulky methyl or even more sterically constraining longer hydrocarbons, but clearly teaches to the importance of positive charge in the antibacterial properties and solubility of chitosan.

The prior art is rich with the synthesis and applications of chitosans with methodology to produce the quaternary amine. A series of patents teach the importance of solubility for materials having necessary activity at physiological pH. For example, a series of patents describe the creation of and use of the quaternary amines as foaming and stabilizing agents in cosmetic compositions. For example, U.S. Pat. No. 4,772,689 to Lang et al. discloses the quaternary chitosan derivatives with hydroxy and propyl substitutions on the amine that are used in cosmetic compositions for the treatment of hair or skin, characterized by a content of new quaternary chitosan. Also disclosed are the new quaternary chitosan derivatives per se as well as processes for their preparation. The chitosan derivatives have a good substantivity, particularly to hair keratin, and prove to have hair strengthening and hair conditioning characteristics. U.S. Pat. No. 4,976,952 to Lang et al. discloses a cosmetic agent for the treatment of the hair and skin that contains macromolecular surface-active, quaternary N-substituted chitosan derivatives with a variety of degrees of substitution and pendant groups on the amine. This invention also comprises chitosan derivatives distinguished particularly by their surface-active properties, for example, their foam-forming and emulsifying properties, and by their hair-setting and hair-conditioning effect. Similar to these are U.S. Pat. Nos. 4,921,949; 4,822, 598 and 4,772,689 all to Lang et al. These describe the action of cation-active polymers, particularly polymers which have quaternary ammonium groups, as conditioning compositions in cosmetic compositions, particularly for the treatment of hair. Based upon a reciprocal action between their ammonium groups and the anionic groups of the hair, the cation-active polymers possess a great affinity for keratin fibers. These series of patents teach to the desirable interactions of polycations and polyanions for particular applications and the ability to modify chitosan to achieve and control those interactions.

Amine Chemistry-acid Coupling

Amines are typically coupled to carboxylic acids using peptide coupling chemistry. These chemistries continue to be performed in organic solvents, primarily for the synthesis of polypeptides and short proteins. Only recently were many of the coupling agents modified to be active in aqueous solutions See *Bioconjugate Techniques* Greg. T. Hermanson (Elsevier, Academic Press: USA) (1996).

Few descriptions exist of chitosan derivatives N-conjugated with different amino acids. Jeon et al., describe low molecular weight chitosan polymers (less than 10,000 Da) with asparagine, glycine, alanine, aspartic acid, cysteine and methionine. However they do not disclose or describe the inherent solubility issues of their chosen amino acids. Rather Jeon et al. rely on inherent solubility provided by selecting low molecular weight chitosan, thereby limiting the applicability of their compounds. Additionally, Jeon et al do not utilize the positively charged amino acids nor do they disclose or describe any correlation between solubility and charge. It is important to note that Jeon et al. focus upon aspargine, an amino acid that is neutral at all pH's. Thus Jeon et al suggest that neutral amines at physiologic pH contribute to antimicrobial activity. This implication teaches away from the present invention. Furthermore, the coupling method disclosed by Jeon et al requires the use of N,N'-dicyclohexylcarbodiimide (DCC) as a coupling agent which is not water soluble. The reaction is preformed in 4:1 methanol:water mixtures with triethyl amine (TEA) as a base to bring the pH to 6.8. After reaction, deprotection is performed in trifluoroacetic acid to remove the boc protecting groups thereby further reducing the MW and producing a large distribution that is not addressed for the various chitosan products disclosed by Jeon et al. Furthermore, the activity disclosed in Jeon et al is not unlike the variability exhibited by low molecular weight chitosan. Thus, Jeon et al fail to teach control of higher weight chitosans, as per the present invention. See Jeon et al.; *Effect*

*of antimicrobial activity by Chitosan oligosaccharide N-conjugated with Asparagine. Microbial. Biotechnol.* 11(2): 281-286 (2001).

It is known that chitosan is an avid coagulant and that chitosan of different molecular weights are utilized to induce clotting and provide hemostasis. See U.S. Pat. No. 4,394,373 to Malette et al. It is also important to note that there are scant disclosures of the desirability of producing arginine bound to chitosan as anticoagulation biomaterials. However, no disclosure is made of the fact that the methodology as disclosed, produces polymers of their chosen amino acids. Additionally, no disclosure is made of any manner of limiting the formation or coupling of poly-amino acids to chitosan as is necessary for the formation of chitosan-arginine. As is well understood by one of ordinary skill, that a mechanism for limiting the formation or coupling of poly amino acids to chitosan is essential to the formation of chitosan-arginine. Additionally, no disclosure is made as to the relevance of charge density to antibacterial properties of chitosan-arginine. Thus, in the absence of such a teaching, severe doubt must be raised as to the probability that the formation of chitosan-arginine has indeed occurred and in such desirable quantities to perform the described utility. See Liu et al.; *A chitosan-arginine conjugate as a novel anticoagulation biomaterial.* J. of Materials Science: Materials in Medicine 15:1199-1203 (2004).

Chinese Patent 1519035A1 provides limited disclosure of the ability to make chitosan-arginine for the purpose of biomedical polymers for in vivo implants. This reference is directed to the inhibition of hemagglutination by chitosan-arginine based upon their disclosure that arginine derivatized chitosan has a longer hemagglutination time than chitosan alone. However, it is important to note that several patents and purchasable products directly contradict the assertion that chitosan based materials can inhibit hemagglutination. See U.S. Pat. No. 4,394,373 to Malette et al. and U.S. Pat. No. 6,162,241 to Coury et al. See also, Klokkevold et al.; *Effect of chitosan on lingual hemostasis in rabbits*; J. Oral and Maxillofacial Surg. 49(8): 858-863 (1991).

The methodology of Chinese Patent 1519035A1 includes peptide coupling that is well known in the literature, and thereafter subjecting the arginine-chitosan product/pre-product to a magnetic field. No disclosure is made as to the relevance of the magnetic field. The references cited by the presently discussed publication evidence an absence of interest in chemically protecting the α-primary amine on the arginine and thus, an inability to control the chemistry at that amine. The importance of control of the primary active amine results in the ability to control coupling, as discussed above. Thus, an active primary amine that is similar in activity to the amine on the chitosan will inevitably react with the coupling agents to react with the activated carboxylate group of other arginines resulting in poly-arginine, either attached to the chitosan or copolymerized in solution. A method of controlling activity on this reaction site is necessary to the production of the chitosan-arginine products as disclosed, and an absence of such a disclosure must lead one of ordinary skill to the conclusion, that the present publication has only addressed the desirability of the formation of such compounds, and not the actual disclosure of such compounds. Additionally, this reference requires insolubility, a characteristic that teaches away from the present invention, particularly antibacterial applications.

A number of patents teach to the addition of amino acids for desirable properties. U.S. Pat. No. 4,908,404 to Benedict et al. discloses that a polymeric backbone of polypeptides having primary or secondary amines can be functionalized with combinations of synthetic amino acids for creating strong bioadhesive materials that are compatible with living tissues. While general teachings of the desirability of coupling multiple components on a cationic backbone are disclosed, the reference is markedly distinguished from the present invention as discussed below.

Further addition of short polypeptides has been attempted on chitosan to stimulate cell growth or adhesion. See Ho et al.; *Preparation and characterization of RGD-immobilized chitosan scaffolds*; Biomaterials 26: 3197-3206 (2005)]. Ho et al describe attaching the four amino-acid polypeptide RGDS through a carbodiimide coupling scheme for the purposes of coupling free amines of the R (arg) peptide as well as the amine on the chitosan. Ho et al also disclose coupling of short polypeptides to an insoluble chitosan matrix for chitosan scaffolds. Another reference discloses coupling a longer polypeptide using an activated reagent that removes the need for protecting the amine on the amino acids. See Masuko, et al.; *Chitosan-RGDSGGC conjugate as a scaffold material for musculoskeletal tissue engineerin*; Biomaterials 26: 5339-5347 (2005). This same coupling agent is also taught in U.S. Pat. No. 7,053,068 to Prinz. Prinz also discloses a method for reacting the amines on chitosan with iminothiolactones, which impart a positive charge to the chitosan and provide an excellent coupling group for thiol chemistry. These can be made to gel or crosslinked for controlled release drug delivery. This reference provides a substantial teaching of the strength of active amine groups and the need for careful control of the chitosan reactive amine for practical coupling.

Textiles

Additional studies include the different responses by bacteria subjected to a range of molecular weight chitosans prepared on textiles. Though very limited in scope, additional variables that are considered in a small number of bacterial studies are; degree of deacetylation, pH, cations and anions present in solution. See Shin et al.; *Molecular weight effect on antimicrobial activity of chitosan treated cotton fabrics*; J. Appl. Poly Sci., 80, 2495-2501 (2001); and Lim et al.; *Review of chitosan and its derivatives as antimicrobial agents and their uses as textile chemicals*, J. of Macromolecular Sci. C43(2), 223-269 (2003). Wound treatments have also been addressed by utilizing a combination of chitosan with silver sulfadiazine for wound dressings and burns. See Mi et al.; *Assymetric chitosan membranes prepared by dry/wet phase separation: a new type of wound dressing for controlled antibacterial release*; J. Membrane Sci.; pp. 212, 237-254 (2003). Additionally wound dressings have also utilized chitosan in combination with glycerol, chitin and ethylene oxide. See Marreco et al.; *Effects of different sterilization methods on the morphology, mechanical properties and cytotoxicity of chitosan membranes used as wound dressings*, Wiley periodicals, 268-277 (2004).

Chitosan-guanidine

The addition of a guanidinium group to a primary amine impart positive charge or polarity or to act as an intermediate step in chemical reactions has been developed primarily in organic solvents. Use of a known guanidinylation (guanilating) reagent, formamidine sulfinic acid, has been demonstrated in absolute methanol for small molecules containing primary amines. See Katritzky et al.; *Recent developments in guanylating agents*. ARKIVOC iv, 49-87 (2005); and Maryanoff et al.; *A convenient synthesis of guanidines from thioureas*; J. Org. Chem. 51, 1882-1884 (1986).

Very little has been reported in the literature for chemical functionalization of the primary amine on chitosan by direct guanidinylation. Due to chitosan's insolubility in organic solvents, syntheses are restricted to aqueous solutions. The effectiveness of chitosan functionalization by typical guanylating agents in water is a challenge, as these are somewhat different than the conditions under which these reagents were originally intended to operate. Reaction with formamidine sulfinic acid is an atom-economical reaction with no by-products, and the sulfinate provides the salt to the positive guanidinyl product.

The chemistry of another guanylating reagent, 1H-pyrazole-1-carboxamidine hydrochloride, has also been examined for primary amines. See Bernatowics et al.; *1H-pyrazole-1-carboxamidine hydrochloride: an attractive reagent for guanylation of amines and its application to peptide synthesis*; J. Org. Chem. 52, 2497-2502 (1992). This reactant can be synthesized and characterized in gram quantities in a single synthetic operation.

The bioactivity of biguanides and chitosan with related biguanidinylations have been disclosed in the prior art. Japanese Patent 60233102 to Toshio discloses a chitosan derivative from dicyandiamine or dyanamide to produce a coagulating material and metal ion absorbant that has biguanide or and or guanidine groups. This reference is distinguished from the present invention because it fails to teach structure and does not provide disclosure of the relevance of solubility charge and antimicrobial properties of the compound.

Microbial Populations

A variety of debilitating diseases and syndromes are the result of poorly regulated microbial populations. Many symptoms of disease are produced by the concurrent bacterial infections that encroach upon weakened immune systems and tissues. A dramatic rise in use of common antibacterials has resulted in the concurrent rise of antibacterial resistant species. Wounds, lacerations and abrasions as well as burns and ulcers are dermal occurrences that are easily contaminated by a variety of environmental bacteria. Prosthetic joint sites where rubbing and abrasion often regularly occur are a common site for chronic infections. Furthermore, microbial imbalances in the gut are fairly frequent. One important example is the peptic ulcer, which is primarily caused by the acid-loving *Helicobacter pylori*, a gram negative bacterium. Inflammatory bowel syndromes, such as Crohn's disease or ulcerative colitis, are the result of the body's inability to control bacterial residence in the gut and the leakage of bacteria across the gut membranes. Peritonitis is an inflammation of the peritoneum and can result the dramatic translocation of bacteria across the gut walls and membranes.

Bacteria have been considered free floating organisms, but in the natural world, most bacteria (~99.5%) aggregate in biofilms and behave differently than their planktonic forms. See O'Toole et al.; *Biofilm formation as microbial development*; Annual Review of Microbiology 54:49 (2000); Watnick et al.; Biofilm city of microbes; Journal of Bacteriology 182: 2675 (2000); Stoodley et al.; Biofilms as Complex Differentiated Communities; Annual Review of Microbiology; 56:187 (2002). Bacterial biofilm formation is an industrial problem affecting water purification systems, heat exchangers and biological sensors. Biofilms serve as a continuous source of planktonic bacteria, which, when released from biofilms, seed formation of new biofilms in new locations.

Biofilms are also a major cause of human disease; chronic bladder infections, colitis, conjunctivitis, and periodontal disease are only a few among many well-established examples See Davies; *Understanding biofilm resistance to antibacterial agents*; Nature Reviews Drug Discovery 2:114 (2003). Biofilms problematically colonize medical devices such as catheters (e.g. urinary catheters are among the worst), contact lenses and artificial implants such as pacemakers, stents, dental and breast implants, and heart-valves among many others. See id. These biofilms are highly resistant both to clearance by the immune system and to antibiotic treatments.

Inside the body, biofilms serve as a protected source of continuously shed bacteria and biofilm fragments. The sloughed-off materials seed into the surrounding tissues and the circulatory system leading to recurrent acute infection. See Anderson et al.; *Intracellular bacterial biofilm-like pods in urinary tract infections*. Science 301:105 (2003). In addition to releasing the extracellular matrix materials, the biofilm-resident bacteria also show protective behaviors (e.g. expression of multidrug efflux pumps) which may play an important role in evolution of multi-drug resistant nosocomial infection. For example, *Pseudomonas aeruginosa*, a common nosocomial pathogen and an adept biofilm-former, is multi-drug resistant at an alarming rate of 95% in the planktonic form.

Biofilm bacteria display profoundly decreased sensitivity to biocides and antibiotics, becoming 10-1000 fold more resistant than the same type of bacteria grown in planktonic culture. See Luppens et al.; *Development of a standard test to assess the resistance of Staphylococcus aureus biofilm cells to disinfectants*; Applied & Environmental Microbiology 68:4194 (2002). Controlling bacterial populations in biofilms is clearly a challenge.

The most common causes of diarrheal diseases are *E. coli, Campylobacter jejuni* and *Shigella*. There are no vaccines approved by the FDA to prevent infection. Intense psychological and physical stressors often lead to respiratory infections such as bacterial pneumonia and streptococcal infections as well as increased susceptibility to viral influenza. *Escherichia coli* are responsible for a variety of diarrheal and intestinal diseases. Diarrhea treated with ciprofloxacin substantially increases the antimicrobial resistance rates for multiple antibiotics, although they appear to return to pretreatment levels within a month. See Shannon et al.; *Antimicrobial Agents and Chemotherapy*; pp. 2571-2572 49:6 (2005). Outbreaks of *E. coli* poisoning due to improper food storage are not infrequent and can lead to high mortality rates due to the specific shiga-like toxins produced by strains such as the O157:H7. Other enteropathic bacteria with devastating effects include *Campylobacter* species, *Salmonella* species, *Shigella* species, and *Vibrio* species, which can produce gastroenteritis with severe diarrhea, nausea and vomiting.

A number of bacteria are associated with battlefield wounds but translate directly into the civilian population. *Acinetobacter baumannii*, a bacterium found in soil and water, has resulted in wound, respiratory, and bloodstream infections. The bacterium poses a danger due to its ability to survive on surfaces for up to 20 days and its apparent resistance to most known antibacterials. *Acinetobacter* is one of the most common gram-negative bacteria to colonize the skin of hospital personnel, potentially increasing the likelihood of nosocomial infection amongst other patients. *A. baumannii* can easily lose susceptibility to the antibiotics available. Only three drugs have been known to have exhibited efficacy against *A. Baumannii*. Imipenem carries a risk of seizure, amikacin, does not work for bone infections and has not been effective against some strains of the bacteria, and colistin, an antibiotic with severe toxic effects on the kidneys. See Aronson et al.; *In Harm's Way: Infections in Deployed American Military Forces*; Clinical Inf. Disease Volume 43: 1045-1051 (2006).

Major complications of burn injuries include fluid loss and wound sepsis due to bacterial infections; a common cause is the *Pseudomonas aeruginosa* organism, which can be difficult to treat due to its resistance to antibiotics. Oral antibiotics, with the exceptions of the fluoroquinolones, are generally ineffective against most serious skin and soft tissue infections by *P. aeruginosa*. See Dale et al.; *Therapeutic Efficacy of "Nubiotics" against Burn Wound Infection by Pseudomonas aeruginosa*; Antimicrobial Agents and Chemotherapy; pp. 2918-2923, 48:8 (2004). Burrowing bacteria such as the *Proteus* are particularly difficult to treat in deep wounds and burns.

A variety of other pathogens have emerged as multi drug resistant. *Klebsiella pneumoniae* can cause nosocomial wound infections and is resistant to ampicillin. Many strains have acquired resistance to carbenicillin, quinolones, and increasingly to ceftazidime. The bacteria remain largely susceptible to aminoglycosides and cephalosporins. Cutaneous infection from *Leishmania major* generally results in chronic, painless skin lesions. *Leishmania tropica* and *Leishmania infantum-donovani* may be associated with visceralization and more chronic, reactivating illness. While treatment controls the clinical disease, it does not destroy the organism. Methicillin resistant *Staphylococcus aureus* (MRSA) is resistant to methicillin and other more common antibiotics such as oxacillin, penicillin and amoxicillin. MRSA infections occur most frequently among persons in hospitals and healthcare facilities who have weakened immune systems. From 1995 to 2004, the percentage of resistant bacteria in ICU patients has increased from <40 to 60% [National Nosocomial Infections Surveillance System, CDC].

In addition, viruses are an important set of microbes that infect almost any type of body tissue, including the brain. Often the use of antibiotics complicates viral infections. Most treatments for viral infections are preventative in the form of vaccines, as the vast majority of human viral infections are controlled by the immune system. However, materials are needed to prevent or treat serious viral infections or reduce viral infectivity.

The present invention overcomes the limitations of the prior art as discussed above and present chitosan derivative compounds that are discussed hereinbelow.

SUMMARY OF THE INVENTION

It is, therefore, an objective of the present invention to control microbial populations in a variety of environments.

It is also another objective of the present invention to inhibit and/or enhance microbial subpopulations and pathogens in a wide variety of environments.

It is yet another objective of the present invention to inhibit of growth of exogenous bacteria, mycoplasma and biofilms.

It is yet another objective of the present invention to promote wound healing due to second and third degree burns, chronic ulcers, bed sores, etc.

It is yet another objective of the present invention to provide chitosan derivative compounds that are capable of controlling, treating and preventing the growth of microbial populations.

It is yet another objective of the present invention to provide chitosan-arginine compounds, and chitosan-guanidine compounds, that are soluble at physiologic pH and utilized to control, treat and prevent the growth of microbial populations.

It is yet another objective of the present invention to provide chitosan-unnatural amino acid compounds, chitosan-acid amine compounds, chitosan-natural amino acid compounds, co-derivatives of chitosan derivative compounds, salts of chitosan derivative compounds and salts of co-derivatives of chitosan derivative compounds that are soluble at physiologic pH and utilized to control, treat and prevent the growth of microbial populations.

It is yet another objective of the present invention to provide a method of synthesizing chitosan-arginine compounds that are soluble at physiologic pH for controlling, treating and preventing the growth of microbial populations.

It is also another objective of the present invention to provide a method of synthesizing chitosan-unnatural amino acid compounds, chitosan-acid amine compounds, chitosan-natural amino acid compounds, co-derivatives of chitosan derivative compounds, salts of chitosan derivative compounds and salts of co-derivatives of chitosan derivative compounds that are soluble at physiologic pH for controlling, treating and preventing the growth of microbial populations.

These and other objectives are discussed hereinbelow.

BRIEF DESCRIPTION OF THE DRAWINGS

FIG. 2 (c) shows the effect of chitosan-arginine (7% functionalized) on *Salmonella enteritidis* 8W 2310 at 24 hours.

FIG. 10 shows chitosan-arginine's effect on viral infectivity of herpes virus, EMCV, influenza virus and vaccinia virus.

FIG. 18 (b) shows chitosan-guanidine's bacteriocidal effect on *S. pyogenes* (Strep A).

FIG. 18 (c) shows chitosan-guanidine's bacteriocidal effect on *B. subtilis*.

FIG. 18 (d) shows chitosan-guanidine's bacteriocidal effect on *A. baumannii*.

FIG. 18 (e) shows chitosan-guanidine's bacteriocidal effect on *S. epidermidis*.

FIG. 18 (f) shows chitosan-guanidine's bacteriocidal effect on *S. aureus*; and FIG. 18 (g) shows chitosan-guanidine's bacteriocidal effect on *P. fluorescens*.

FIG. 18 (h) shows the summary of chitosan-guanidine's bacteriocidal effect on *E. coli, S. pyogenes* (Strep A), *B. subtilis, A. baumannii, S. epidermidis, S. aureus,* and *P. fluorescens*.

FIG. 19 (b) shows the bacteria count of *S. aureus* after 1 hour exposure to chitosan-guanidine.

FIG. 19 (c) shows the bacteria count of *S. pyogenes* (Strep A) after 1 hour exposure to chitosan-guanidine.

FIG. 19 (d) shows the bacteria count of *A. baumannii* after 1 hour exposure to chitosan-guanidine.

FIG. 19 (e) shows the bacteria count of *S. epidermidis* after 1 hour exposure to chitosan-guanidine.

FIG. 19 (f) shows the bacteria count of *P. fluorescens* after 1 hour exposure to chitosan-guanidine.

FIG. 19 (g) shows the bacteria count of *E. coli* after 1 hour exposure to chitosan-guanidine.

DETAILED DESCRIPTION OF THE EMBODIMENTS

Figure 1A:
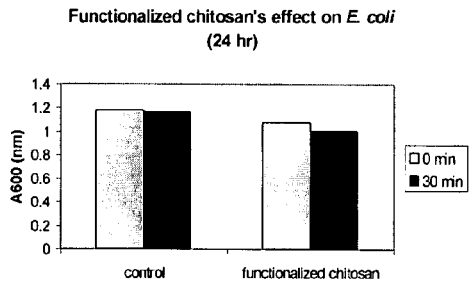
FIG. 1(a) shows the effect of chitosan-arginine (7% functionalized) on *E. coli* at 24 hours.
Figure 1B:
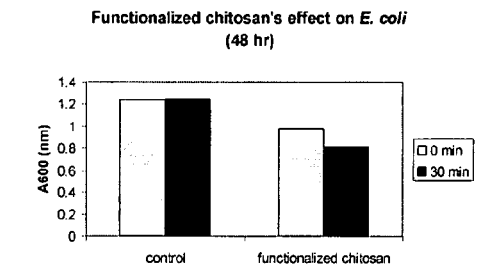
FIG. 1(b) shows the effect of chitosan-arginine (7% functionalized) on *E. coli* at 48 hours.
Figure 1C:
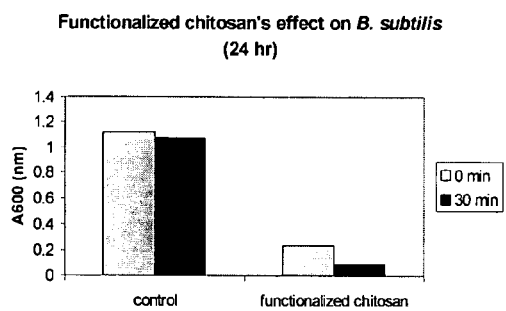
FIG. 1(c) shows the effect of chitosan-arginine (7% functionalized) on *B. subtilis* at 24 hours.
Figure 1D:
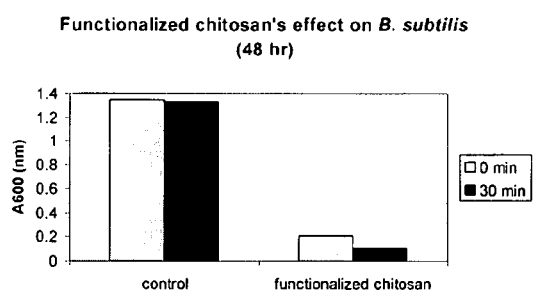
FIG. 1(d) shows the effect of chitosan-arginine (7% functionalized) on *B. subtilis* at 48 hours.
Figure 1E:
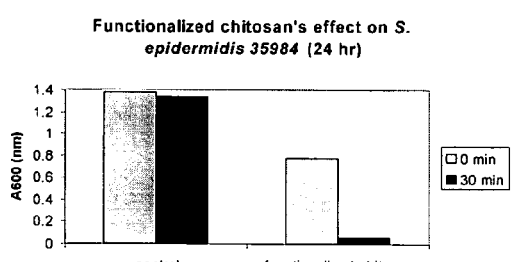
FIG. 1(e) shows the effect of chitosan-arginine (7% functionalized) on *S. epidermidis* 35984 at 24 hours.
Figure 1F:
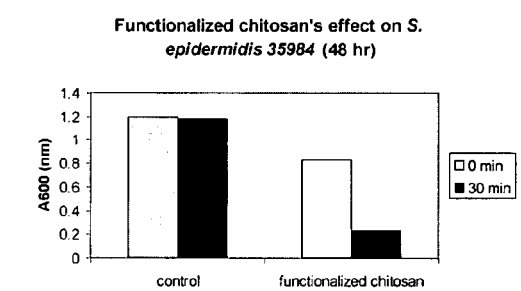
FIG. 1(f) shows the effect of chitosan-arginine (7% functionalized) on *S. epidermidis* 35984 at 48 hours.
Figure 1G:
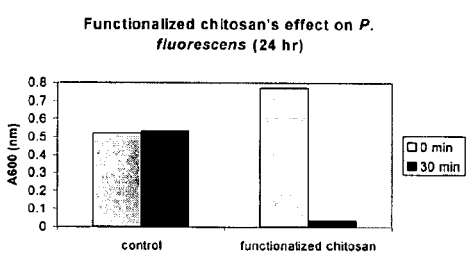
FIG. 1(g) shows the effect of chitosan-arginine (7% functionalized) on *P. fluorescens* 700830 at 24 hours.
Figure 1H:
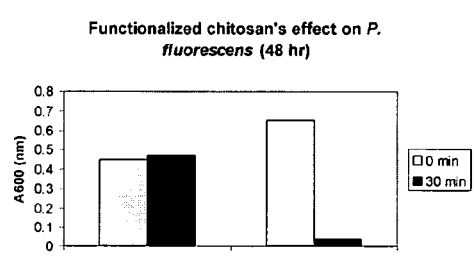
FIG. 1(h) shows the effect of chitosan-arginine (7% functionalized) on *P. fluorescens* 700830 at 48 hours.
Figure 1I:
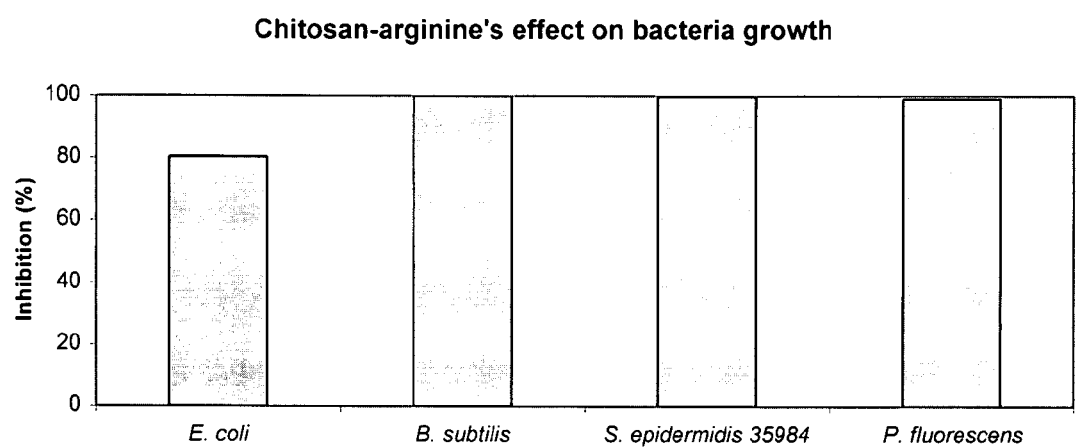
FIG. 1(i) shows the summary inhibitory effect of chitosan-arginine (7% functionalized) on *E. coli, B. subtilis, S. epidermidis* 35984 and *P. fluorescens* 700830 at 48 hours incubation FIG. 2 (a) shows the effect of chitosan-arginine (7% functionalized) on *Klebsiella pneumoniae* 85W 1880 at 24 hours.

The present invention is directed to the control of microbial populations in a variety of environments. Inhibition and/or enhancement of particular subpopulations of microbes and pathogens is desirable in a wide variety of environments. For the purposes of the present invention, microbial populations include, but are not limited to, bacteria, mycobacteria, mycoplasma, viruses, protozoas and prions. For example, control of bacterial populations, including the general microbiota balance, is important in gut health. Additionally, the impermeability of the peritoneum to selective bacteria, control of inflammatory bowel syndrome and control of enteropathic diseases are also highly desired. Growth of cells in cell culture media requires the inhibition of growth of exogenous bacteria, fungi and mycoplasma. Wound healing, such as in chronic ulcers, bed sores, lacerations and other sources of potential infections, requires inhibition of bacterial growth as well as enhancing cellular signals that promote wound healing. Oral care involves selective control of bacterial populations as well. Control of bacterial populations in burn induced wounds, particularly in $2^{nd}$ and $3^{rd}$ degree burn wounds, requires a soluble antibacterial that penetrates into corrugated and necrotic tissue crevices where bacteria reside. Bacterial populations as well as biofilm growth, particularly in the lung must also be minimized. Growth enhancement of livestock, such as poultry, ruminants, etc, are also controlled by selective use of antibacterials as food additives. As is understood to one skilled in the art, the applications of the present invention can be extended to any areas where control and/or inhibition of microbial populations is desirable.

The present invention is also directed to the prevention of bacterial and/or pathogenic infection or contamination, as well as the prevention of biofilm formation. Additionally, this invention is particularly important in precluding contamination of pre-sterilized medical materials such as, but not limited to, textiles, IV bags and tubing, catheters, masks, medical materials such as medical grade latex, PVC, silicone, rubber, or the like.

The present invention accomplishes the control of microbial populations, the prevention of bacterial or and/or pathogenic infection or contamination, and prevention of biofilm formation by providing chitosan derivative compounds including but not limited to chitosan-arginine compounds, chitosan-guanidine compounds, chitosan-unnatural amino acid compounds, chitosan-acid-amine compounds, chitosan-natural amino acid compounds, co-derivatives of the just described compounds and the salts thereof. These compounds are capable of being formed into soluble powders, films, coatings, gels, laminate, nanoparticles, impregnated onto biohazard masks or the basis of the mask, woven and non-woven fibers, nanofibers, encapsulated for pharmaceutical applications, time-released pharmaceutical composition, and mixtures of different chitosan derivative compounds. Additionally, the chitosan derivative compounds of the present invention have ultra-low endotoxin levels. The chitosan-derivative compounds of the present invention are efficacious over a broad pH range, ie, 1-10. However in accordance with the present invention these chitosan-derivative compounds provide markedly improved antimicrobial properties and solubility at physiologic pH. Physiologic pH is defined as the pH range between 6.8 and 7.4.

Chitosan is the deacetylated form of chitin. Although chitosan itself has some antibacterial activity, this activity is limited by its solubility and lack of significant positive charge at physiological pH. It is known that at low pH, chitosan forms a polycationic structure that can interact with anionic compounds and macromolecular structures. Since the degree of protonation increases with increased acidic conditions, solubility in aqueous solutions also increases. This increased solubility and protonation is directly proportional to increased antibacterial activity. Conversely, the degree of aqueous solubility decreases with decreased acidic conditions, as does antibacterial activity.

The chitosan-derivative compounds, of the present invention, overcome the issues of solubility and charge as well as molecular weight, charge density, charge distribution and placement of charge in order to provide improved and selective antibacterial activity. Like the fibrous material of all polysaccharides including chitosan, these chitosan derivative compounds retain the properties of a natural biomaterial that is not metabolized, not absorbed in the body and does not cross the blood brain barrier. Because of these properties, these chitosan derivative compounds are a novel and powerful class of antibiotics.

Control of molecular weight, charge density, charge distribution and placement of charge from the chitosan backbone allows for selective microbicidal activity. The backbone of the chitosan polysaccharide, as shown in (1) above, is a linear chain of glucose-substituted monomers (also referred to as "glucose monomers", below) connected by a glycosidic bond. Each of the glucose monomers has either an amine or an acetyl amine, indicated by the fractions p and q, respectively, where p+q=1 and where p≧0.5. Functionalization of the chitosan backbone, occurs at either the primary amine or either of the two hydroxyl groups on the glucose ring. To optimize functionalization opportunities, the primary amine of the chitosan backbone is the reactive site. To optimize control of microbial populations, the present invention is directed to correlating the sensitivity of different microbial species and strains to the molecular weight of the chitosan-derivative compounds.

In accordance with the present invention, the sensitivity of different microbial species and strains is also dependent on the charge density of the chitosan derivative compounds, which is in turn directly related to the degree of functionalization. Functionalization is defined as the coupling of a molecule containing a carboxylic acid to the primary amine. Functionalization is also defined as the direct guanidinylation of the primary amine. The functionalized chitosan-derivative compounds of the present invention are developed to vary in molecular weights and charge densities depending upon their use. The degree of functionalization imparts a particular charge density to the chitosan derivative compounds. For a particular molecular weight, the higher the functionalization with positive charge, the higher the charge density on the polymer chain. However, it is important to note that compounds having very high degrees of functionalization may be toxic to mammalian cells. Increased charge density produces higher solubility and higher efficiency of microbiostatic or microbiocidal activity. Increased charge density also increases the interactions with mammalian cell membranes. Thus, this invention is also directed to balancing functionalization with toxicity in mammals and humans, so as to provide optimal efficacy and minimal toxicity in all environments and utilities.

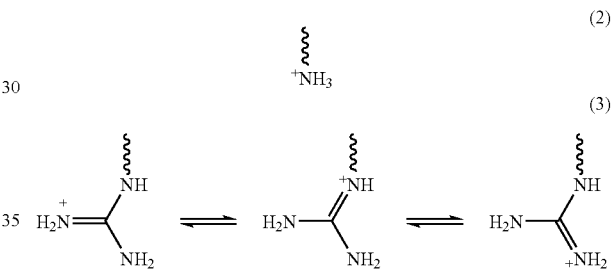

The sensitivity of different microbial species and strains is also dependent upon the charge distribution of the compounds. The charge distribution is either a single point charge as shown in (2) or a resonance structure as shown (3). A point charge must be located at a particular site for optimal interaction whereas a charge distribution interacts simultaneously with multiple negative charges or polar groups.

The sensitivity of different microbial species and strains is dependent upon the position of the charge relative to the chitosan backbone, (1), of the chitosan-derivative compounds, discussed below. Additionally, the position of the charge is also varied by choice of the functionalizing group, as described below. Finally, the sensitivity of different microbial species and strains is also dependent on compound dosage relative the concentration of microbial species.

The present invention provides protonated and positively charged chitosan-derivative compounds that are soluble and/or active at physiologic pH while imparting significant antimicrobial activity. Depending on its application, the present invention incorporates these positively charged chitosan compounds as bacteriocidal or bacteriostatic agents. These compounds will have minimal residual endotoxin and protein concentrations.

This invention is also directed to the control of microbial populations through the antimicrobial activity of chitosan-derivative compounds, an activity that is controlled by charge density imparted by the degree of functionalization of the chitosan-derivative compounds and by overall molecular weight. The antibacterial activity is broad spectrum and is concentration dependent. In accordance with the present invention the molecular weight of the chitosan derivative compounds is between 25,000 Da and 1,000,000 Da.

Particular classes and/or species of microbes can be targeted by manipulation of composition and formulation of the chitosan-derivative compounds. These include but are not limited to gram-positive bacteria, gram negative bacteria, mycobacteria, mycoplasma, and viruses, protozoas and prions. Specific targeted bacteria include but are not limited to those listed in Table 1.

TABLE 1

| Gram negative | |
|---|---|
| *Escherichia coli* | gastroenteritis, urinary tract infections |
| *Pseudomonas aeruginosa* | predominant infection in patients with cystic fibrosis |
| *Pseudomonas fluorescens* | plant infections and a model for *P. aeruginosa* (CF and burn ward infections |
| *Acinetobacter baumannii* | battle wounds |
| *Klebsiella pneumonia* | pneumonia in community settings (tends to affect people with underlying diseases, such as alcoholism, diabetes and chronic lung disease |
| *Shigella flexneri* | gastroenteritis and a model for dysentery |
| *Salmonella typhi* | gastroenteritis |
| *Proteus mirabilis* | wound infection, septicemia and pneumonias, mostly in hospitalized patients |
| Gram positive | |
| *Bacillus subtilis* | model for anthrax and *Bacillus cereus* |
| *Staphylococcus aureus* | boils, hospital infections, toxic shock |
| *Staphylococcus epidermidis* | hospital infections, especially catheters |
| *Streptococcus mutans* | key bacteria in biofilm of teeth, required for most tooth decay |
| *Streptococcus pyogenes* (Strep A) | a cause of 'strep throat", impetigo and necrotizing fasciitis |

Viruses are small particles containing either DNA or RNA encapsulated by protein coat, occasionally containing lipids. In their infective form outside a cell, the particle is a virion that may be infective. The present invention is also directed to the prevention of viral infection. In a preferred embodiment, the chitosan-derivative compounds of the present invention are utilized as surface binding agents. Surface binding applications include, but are not limited to masks, gloves, clothing, textiles, wipes, etc. Surface applications also include, but are not limited to chitosan-derivative compounds as binding agents in solution. Table II, below, lists viruses that were studied, and the applications of the chitosan-derivative compounds against the viruses. As is understood by one of ordinary skill, Table II is exemplary of tested viruses and does not encompass the entire group of viral pathogens against whom the compounds of the present invention are effective.

TABLE II

| Viruses Tested | Description |
|---|---|
| influenza A (H1, N1) | major pathogen of humans and a model for H5N1 (bird flu) |
| vaccinia virus (Copenhagen strain) | model for small pox, monkey pox and *Molluscom Contagium* (a pathogen of HIV patients) |
| herpes simplex 1 (sp7 strain) | pathogenic, neuroinvasive strain obtain from a fatal neonatal infection. |
| encephalomyocarditis virus | picornavirus that is a model for polio, foot and mouth disease (a major threat to cattle, sheep, horses) and hepatitis A |

The present invention is directed to the following chitosan-derivative compounds:
(A) Chitosan-Arginine compounds;
(B) Related chitosan-L/D unnatural amino acid compounds;
(C) Chitosan-acid amine compounds;
(D) Chitosan-L/D natural amino acid derivative compounds;
(E) Co-derivatives of the chitosan-derivative compounds;
(F) Salts of the chitosan derivative compounds; and
(G) Chitosan-guanidine compounds.

In accordance with a preferred embodiment, selectivity of microbiocidal activity is controlled by degree of chitosan-derivative functionalization and by use of particular molecular weights. Targeted delivery of chitosan-arginine and the chitosan-derivative compounds to particular locations in the body is controlled by manipulation of composition and formulation of these chitosan-derivative compounds. It is within the scope of the present invention to control solubility via selective natural and unnatural amino acid derivatization, via acid-amine derivatization, and by mixtures of derivatives and antibacterial properties at various pH.

(A) Chitosan-arginine Compounds:

The present invention is directed to chitosan-arginine compounds, where the arginine is bound through a peptide (amide) bond via its carbonyl to the primary amine on the glucosamines of chitosan. Chitosans with any degree of deacetylation greater than 50% are used with arginine functionalization between 2% and 50%. The degree of functionalization imparts a specific charge density to the chitosan-arginine compound. For a particular molecular weight, the higher the functionalization with positive charge, the higher the charge density on the polymer chain. However, it is important to note that the issue of increased functionality is tempered by potential increases in toxicity with mammalian cells at very high degrees of functionalization. Increased charge density produces higher solubility and higher efficiency of microbiostatic or microbiocidal activity. Increased charge density also increases the interactions with mammalian cell membranes. In accordance with this present invention, it is important to balance functionalization with toxicity to provide optimal efficacy and minimal toxicity in all uses or utilities.

Broad control over bacterial populations is achieved by utilizing a large range of molecular weights of chitosan-arginine compounds. In accordance with the present invention, the chitosan-arginine compounds have molecular weights (MW) between 25,000 and 1,000,000 Da. Lower MW's chitosan-arginine compounds are effective and soluble with lower percent functionalization than larger MW chitosan-arginine compounds. Depending upon application, the chitosan-arginine compounds having greater MW distribution and narrowly focused polydispersity are within the scope of the present invention.

(4)

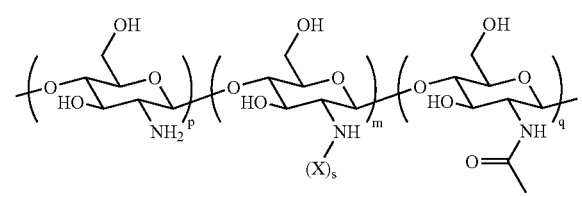

where X is:

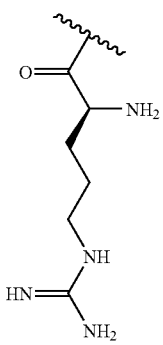

(5a)

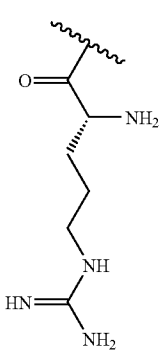

(5b)

In accordance with the present invention, chitosan-arginine compounds, where X is as shown in (5a) as L-arginine and in (5b) as D-arginine, exhibits a random distribution of arginine on the primary amines with a numerical ratio of functionalized to nonfunctionalized amines as indicated in (4) as p and q. The guanidine group on the arginine can be protonated as shown in (3). In this case, s=1. The position of each of the m monomers with the arginine functionalized primary amine is distributed along the backbone where m is 0.02-0.50, related to the degree of functionalization of the primary amines. The subscripts p and q represent the degree of deacetylation such that q is between 0.50 and 0.01 and the position of each of the p or q monomers is distributed along the backbone randomly. As is understood by one of ordinary skill in the art, the representation of monomers in this format indicates a number distribution and not a physical placement as a block copolymer. In a preferred embodiment q is less than 0.20. The sum p+q+m=1. Note that not all of the monomers on the chitosan backbone are deacetylated. Given a particular degree of deacetylation the number of free amines is calculated. Upon reaction with arginine, the degree of functionalization is determined relative to the number of free amines and is presented as a percent, $m/(1-q) \cdot 100\%$. The upper limit of functionalization is determined by both sterics and electrostatics. The tert-butyloxycarbonyl (boc)-arginine is similar in size to a glucose monomer, and has some fairly extensive rotational degrees of freedom. However, the positive charge with its extensive resonance over three atoms as shown in (3) provides an electrostatic repulsion that is difficult to overcome, even in very high salt concentrations. Consequently, an upper limit of approximately 0.50 fractional functionalization is reasonably achieved.

Non-boc-protected arginine, polyarginine functionalization is as described in (4) above where s, a polymerization factor between 1 and 10 as described by comb-like polymers with up to 50% of the total MW fulfilled by arginine, and a random distribution of polyarginine lengths and positions. One of ordinary skill in the art will recognize that the functionalized chitosans will have an average degree of functionalization and polymerization. The polymerization factor, s, thus need not be an integer as s is averaged over m reactive sites.

A preferred embodiment of the present chitosan-arginine compound shown in (6), below is the L-stereoisomer of arginine coupled to chitosan. Here, m is 0.02-0.50, related to the degree of functionalization of the primary amines. The subscripts p and q represent the degree of deacetylation such that q is between 0.50 and 0.01 and the position of each of the p or q monomers is distributed along the backbone randomly. As is understood by one of ordinary skill in the art, the representation of monomers in this format indicates a number distribution and not a physical placement as a block copolymer. In a preferred embodiment q is less than 0.20. The sum p+q+m=1. Note that not all of the monomers on the chitosan backbone are deacetylated. Given a particular degree of deacetylation the number of free amines is calculated. Upon reaction with arginine, the degree of functionalization is determined relative to the number of free amines and is presented as a percent, $m/(1-q) \cdot 100\%$. The upper limit of functionalization is determined by both sterics and electrostatics. The tert-butyloxycarbonyl (boc)-arginine is similar in size to a glucose monomer, and has some fairly extensive rotational degrees of freedom. However, the positive charge with its extensive resonance over three atoms as shown in (3) provides an electrostatic repulsion that is difficult to overcome, even in very high salt concentrations. Consequently, an upper limit of approximately 0.50 fractional functionalization is reasonably achieved.

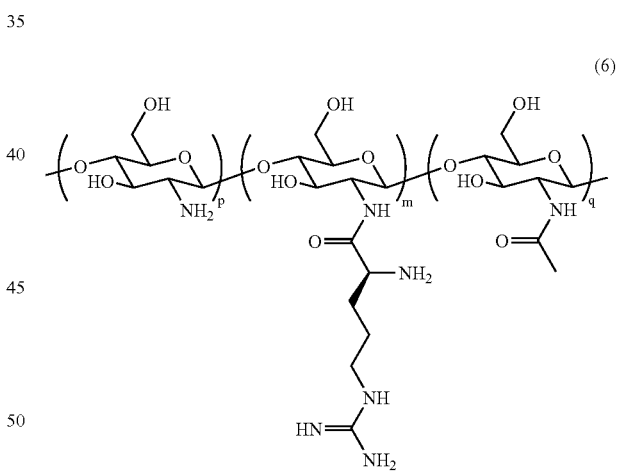

(6)

In a preferred embodiment, soluble chitosan-arginine is used as an antibacterial in burn and wound treatment. A solution of chitosan arginine (dissolved in any biocompatible aqueous solution, salve or cream) is delivered to the burn or wound site. Chitosan-arginine is used as a preventative treatment or a treatment to reduce infection. Many wounds become chronically infected such as dermal ulcers including diabetic ulcers and decubitous ulcers (bed sores) or appear to be caused by infection such as the gastric ulcer by *H. pylori*. Other ulcers of the gut and digestive system include peptic, gastric, stomach, aphtous, duodenal, or esophageal ulcers.

Burn morphologies, particularly in severe cases of 3$^{rd}$ degree burns, provide an exceptional medium for bacteria to grow. Necrotic and dying tissue provides nooks and crannies in which bacteria thrive and gauzes and bandages do not access. The soluble chitosan-arginine provides an increased antibacterial efficacy Examples 1 though 13, below show in-vitro activity of chitosan-arginine (L stereochemistry) compounds with a preferred molecular weight distribution between 25 kDa and 350 KDa. As shown below, these compounds are soluble at physiologic pH and have broad antimicrobial activity against both gram-negative and gram-positive bacteria. Also as shown below, the chitosan-arginine compounds are also active against both planktonic bacteria and bacteria in biofilms. In addition to having bactericidal activity against bacteria in preformed biofilms, the chitosan-arginine compounds also inhibits biofilm formation. Furthermore, chitosan-arginine with broad MW distribution is used to control bacterial growth in tissue culture media at a concentration that is non-toxic to mammalian cells. The activity of chitosan-arginine is dependent upon the charge density and shows different efficacy with different bacteria. The examples also show in-vitro activity of chitosan-arginine to bind virions and reduce infectivity. Finally, the chitosan-arginine compounds show an increase in survivability by 100% over standard burn care protocol:

EXAMPLE 1

Broad Bacteriocidal Properties of Chitosan Arginine: Planktonic Growth

The bacteriocidal activities of chitosan-arginine was compared for both gram-positive and gram-negative bacteria. 6% functionalized chitosan-arginine that is highly positively charged without the addition of an acid, and having broad molecular weight distribution between 25 kDa and 350 KDa, was tested at physiological pH. Both pathogenic and non-pathogenic bacteria 'model' bacteria were tested either in either planktonic growth conditions. Five gram-negative bacteria, *Escherichia coli*, *Pseudomonas fluorescens*, *Klebsiella pneumoniae*, *Shigella flexneri* and *Salmonella enteritidis*; and two gram-positive bacteria, *Bacillus subtilis*, *Staphylococcus epidermidis* were tested. The non-pathogenic bacteria were chosen because they are models for their pathogenic counterparts: *Escherichia coli* K12 is a model for enterotoxigenic *E. coli* (ETEC), enteroinvasive *E. coli* (EIEC), enterohemorrhagic O157:H7 *E. coli* (EHEC), enteropathogenic *E. coli* (EPEC), and enteroaggregative *E. coli* (EAggEC). *Pseudomonas fluorescens* is a model for *P. aeruginosa* and *Burkholderia*. *Bacillus subtilis* is a model for *B. anthracis* and *B. cereus*. *Staphylococcus epidermidis* is a model for *S. aureus* and *S. saprophiticus*. The effect of chitosan-arginine on the bacterial growth in planktonic cultures was determined by measuring the optical densities (600 nm) of the liquid growth medium at various times post inoculation. All were grown overnight in trypticase soy broth (TSB). The original cell density is uniformly ~$10^9$ cells at which point the media is replaced by media containing 0.1% chitosan-arginine 7% functionalized. As seen in FIGS. 1(*a*) through 1(*h*), 7% functionalized chitosan-arginine was very effective at bacteriocide of *B. subtilis*, *S. epidermidis*, and *P. fluorescens* at 24 and 48 hours at physiological pH and displayed a weaker inhibitory activity against *E. coli*. The two bars in the data indicate the initial OD at 0 min that contains both live and dead cells and the OD at 30 min which indicates the remaining live bacteria. This data demonstrates a dramatic inhibition of the planktonic proliferation of *B. subtilis*, *S. epidermidis*, and *P. fluorescens*, with viability decreasing by >99% at the concentration <<0.1%. Samples for viable cell counts were taken from the solutions above. 100 µL of each solution were plated on agar and plates were incubated for ~26 hrs at 37° C. Live cells per mL of original solution were calculated, giving rise to the summary corroborating data in FIG. 1(*i*). Thus, with the exception of *E. coli* which is inhibited ~80%, chitosan-arginine effectively kills >99% of these bacteria at very low doses and possesses a broad and varied spectrum of antibacterial properties.

EXAMPLE 2

Minimum Inhibitory Dose of Pathogen Models

Figure 2A:
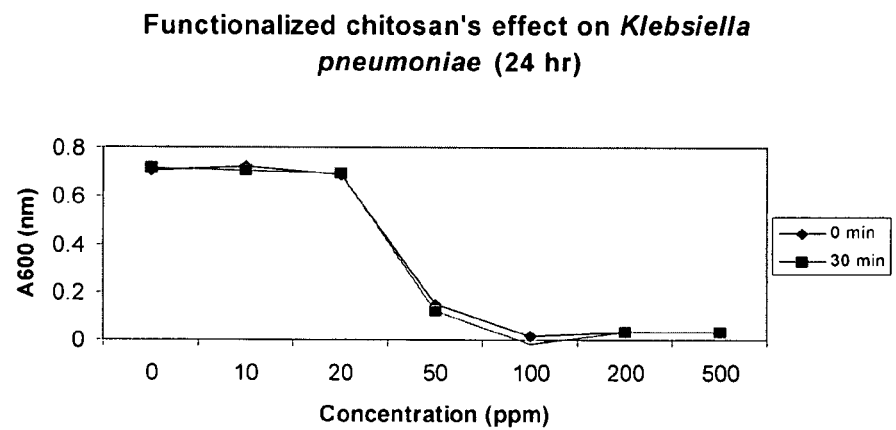
FIG. 2 (b) shows the effect of chitosan-arginine (7% functionalized) on *Shigella flexneri* 85W 2332 at 24 hours.
Figure 2B:
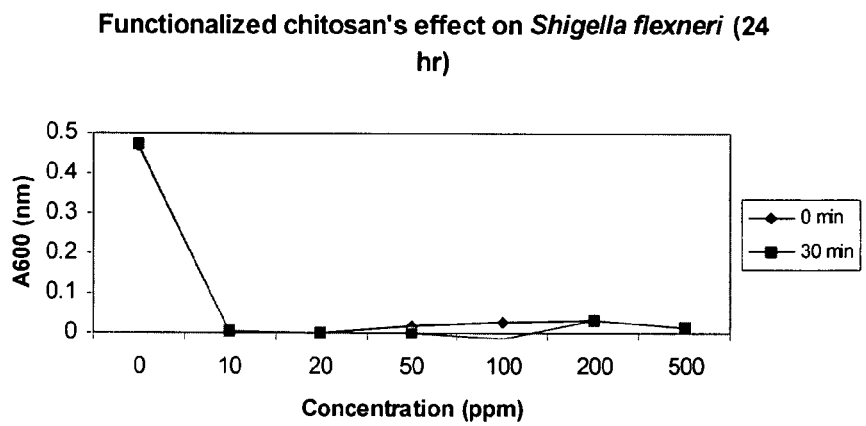
Figure 2C:
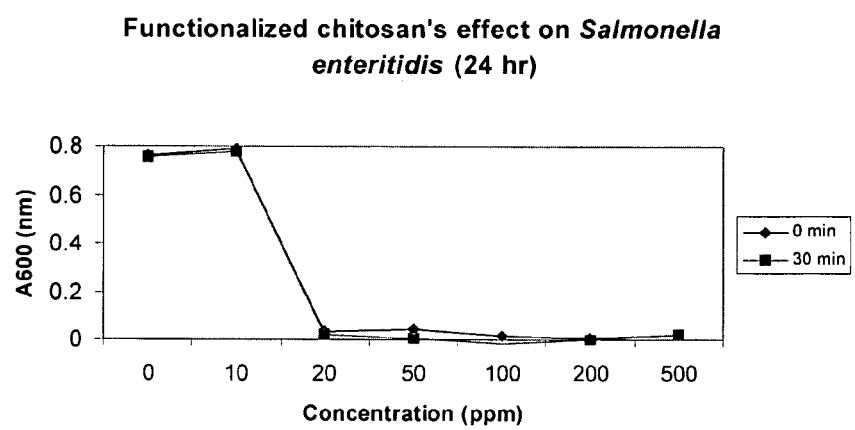
Figure 3A:
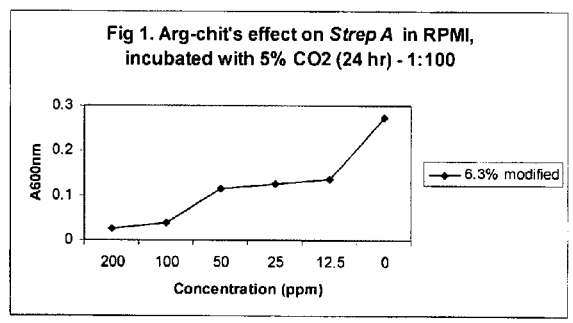
FIG. 3(a) shows the bacteriocidal effect of chitosan-arginine (6.3% functionalized) for *Streptococcus pyogenes* (Strep A) in cell culture media for $10^7$ cells.
Figure 3B:
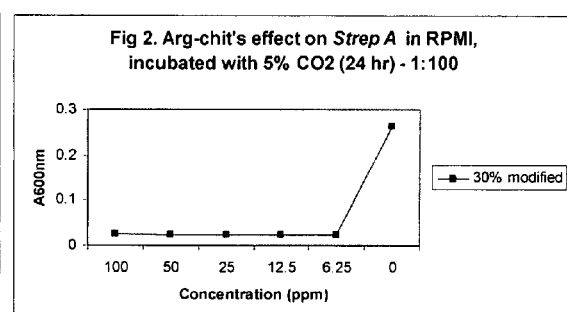
FIG. 3(b) shows the bacteriocidal effect of chitosan-arginine (30% functionalized) for *Streptococcus pyogenes* (Strep A) in cell culture media for $10^7$ cells.
Figure 3C:
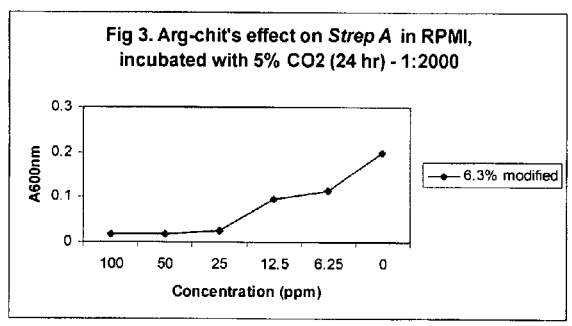
FIG. 3(c) shows the bacteriocidal effect of chitosan-arginine (6.3% functionalized) for *Streptococcus pyogenes* (Strep A) in cell culture media for $2 \times 10^5$ cells.
Figure 3D:
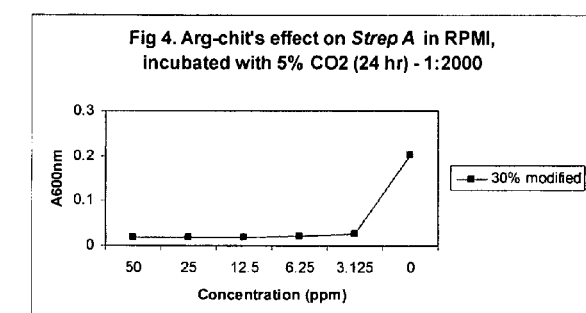
FIG. 3(d) shows the bacteriocidal effect of chitosan-arginine (30% functionalized) for *Streptococcus pyogenes* (Strep A) in cell culture media for $2 \times 10^5$ cells.

The effect of chitosan-arginine on the bacterial growth in planktonic cultures of the gram negative pathogens *Klebsiella pneumoniae*, *Shigella flexneri* and *Salmonella enteritidis* was determined by measuring the optical densities (600 nm) of the liquid growth medium at various times post inoculation. The bacteria *Klebsiella pneumoniae*, *Shigella flexneri* and *Salmonella enteritidis* were grown overnight in Nutrient Broth, all at 37° C. with shaking. The original cell density was uniformly ~$10^9$ cells, and the 0 dose of chitosan-arginine was performed using nanopure water as the control. The effect on viability as a function of dose of chitosan arginine was determined via standard plate counts. 7% functionalized chitosan-arginine at physiological pH dramatically inhibited the planktonic proliferation of *K. pneumoniae*, *S. flexneri*, and *S. enteritidis* in 24 hrs as demonstrated in FIGS. 2(*a*), 2(*b*) and 2(*c*) respectively, with viability decreasing by >99% at the concentration between 10 and 500 ppm. The minimum inhibitory concentrations (MICs) were observed for *K. pneumoniae*, *S. flexneri*, and *S. enteritidis* to be ~100 ppm, ~10 ppm, and ~20 ppm respectively. Based on these findings, the effectiveness of chitosan-arginine against other bacterial types can be determined based upon optimal minimal inhibitory concentration (MIC) of chitosan-arginine for each bacteria.

EXAMPLE 3

Effect of Charge Density on Bacteriocide

The mechanism of antibacterial action of chitosan-arginine is dependant on the addition of positive charges and increased solubility. As demonstrated in FIG. 3, the amount of positive charge on the chitosan-arginine affects its bacteriocidal dose. The effect of two derivatives of chitosan-arginine, functionalized at 7% and 30% with a broad MW distribution between 25 kDa and 300 kDa were demonstrated for *Staphylococcus pyogenes* (Staph A) in cell culture media for two different innoculation doses of Staph A. Staph A was inoculated into cell culture media, RPMI, for an overnight growth at 37° C. with shaking, where the growth saturates as the nutrients get depleted, resulting in a consistent density that is about $10^9$ ($OD_{600}$<<0.7) cells per ml for all strains tested. This fresh overnight growth was diluted to 1:100 or 1:2000 into RPMI and initial optical density (OD) measurements at 600 nm were taken to establish the baseline OD for a given concentration of cells. To individual wells, doses of chitosan-arginine, as described above, were added at 100, 50, 25, 12.5 and 6.25 ppm for the 7% chitosan-arginine and 50, 25, 12.5, 6.25 and 3.125 ppm for the 30% chitosan-arginine. The surviving bacteria were grown for the subsequent 24 hours in the presence of the chitosan-arginine at 37° C. in the presence of $CO_2$ with shaking. The final ODs (corroborated by plate counts) were plotted, as shown in FIG. 3. As demonstrated in FIGS. 3(*a*) and 3(*c*) the 7% functionalized chitosan-arginine inhibited the 1:100 fully at 100 ppm and the 1:2000 dilution fully at 25 ppm. At concentrations lower than these optimal relative amounts to cell density, the 7% chitosan-arginine was not 100% efficient. However, as demonstrated in FIGS. 3(*b*) and 3(*d*), the 30% functionalized chitosan-arginine was effective at inhibiting bacterial growth with nearly 100% efficacy for all doses examined for both Strep A concentrations. The efficiency of bacteriocide was controlled by the charge density as determined by functionalization.

EXAMPLE 4

Biofilm Inhibition

Figure 4:
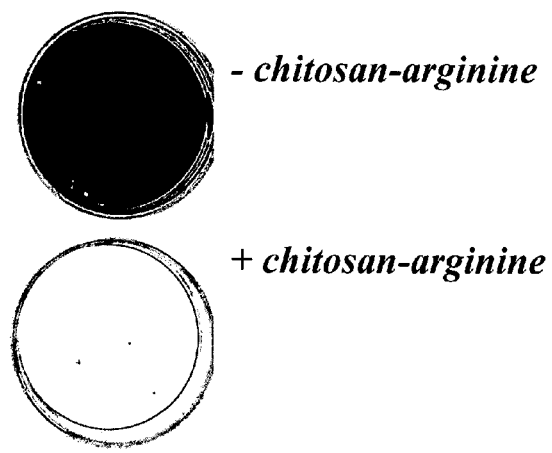
FIG. 4 shows chitosan-arginine's ability to inhibit the formation of biofilms of *S. epidermidis*.

The efficacy of chitosan-arginine on biofilm formation was demonstrated using the following assay: bacteria (*S. epidermidis*) were inoculated into LB and grown overnight to saturation; this resulted in a final density of about $10^9$ ($OD_{600}$<<0.7) cells per ml for all strains tested. This fresh overnight growth was then diluted 1:1000 into LB to the final bacterial concentration of $10^9$ ($OD_{600}$<<0.1). Equal aliquots of thus diluted bacteria were placed either into 30 mm tissue culture plates and the functionalized chitosan added to the desired final concentration (0.1% or 1000 ppm in this figure). The plates were incubated for 24 hours at 37 deg. C. without shaking. Thereafter, the media with the non-adherent, planktonic bacteria, was poured off and the biofilm which adheres to the bottom of the dish, stained with 1% crystal violet and photographed. The extent of biofilm formation was quantified by staining with 1% crystal violet. As Seen in FIG. 4, the film grew wells in the absence of chitosan arginine and chitosan-arginine significantly inhibited the formation of biofilm.

EXAMPLE 5

Bacteriocidal Activity in Biofilms

Figure 5A:
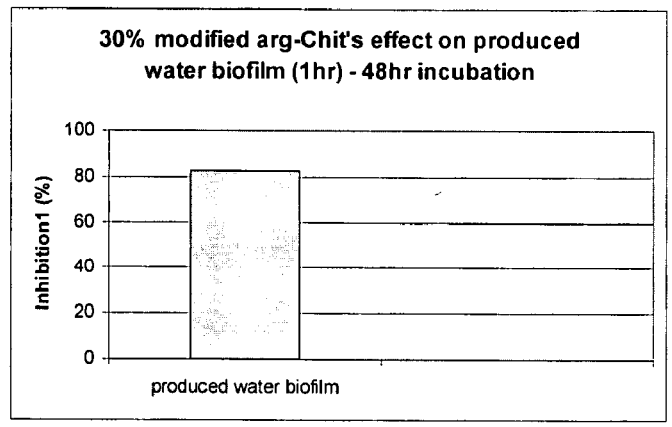
FIG. 5(a) shows chitosan-arginine's bacteriocidal activity in natural water preformed biofilms.
Figure 5B:
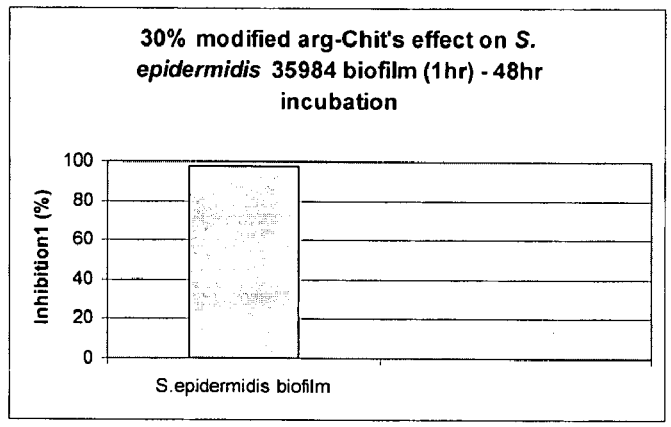
FIG. 5(b) shows chitosan-arginine's bacteriocidal activity in preformed biofilms of *S. epidermidis*.
Figure 5C:
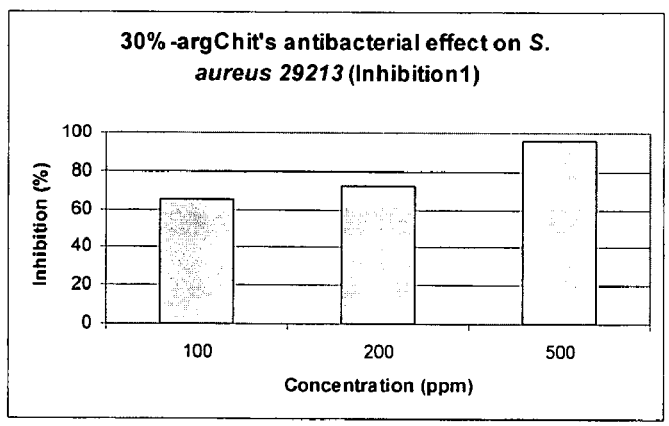
FIG. 5(c) shows chitosan-arginine's dose response of bacteriocidal activity in preformed biofilms of *S. aureus*.
Figure 6A:
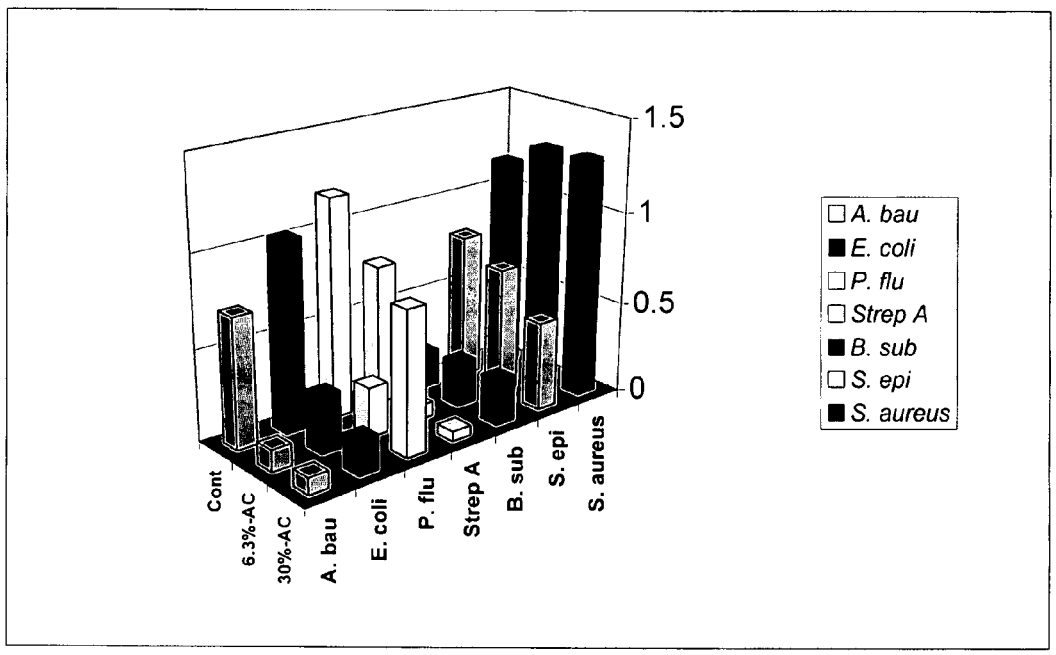
FIG. 6(a) shows the charge density and broad spectrum antibacterial effect of chitosan-arginine (6.3% and 30% functionalized) for *A. baumannii, E. coli, P. fluorescens, S. pyogenes* (Staph A), *B. subtilis, S. epidermidis*, and *S. aureus* at 24 hrs., with a 1:50 dilution.
Figure 6B:
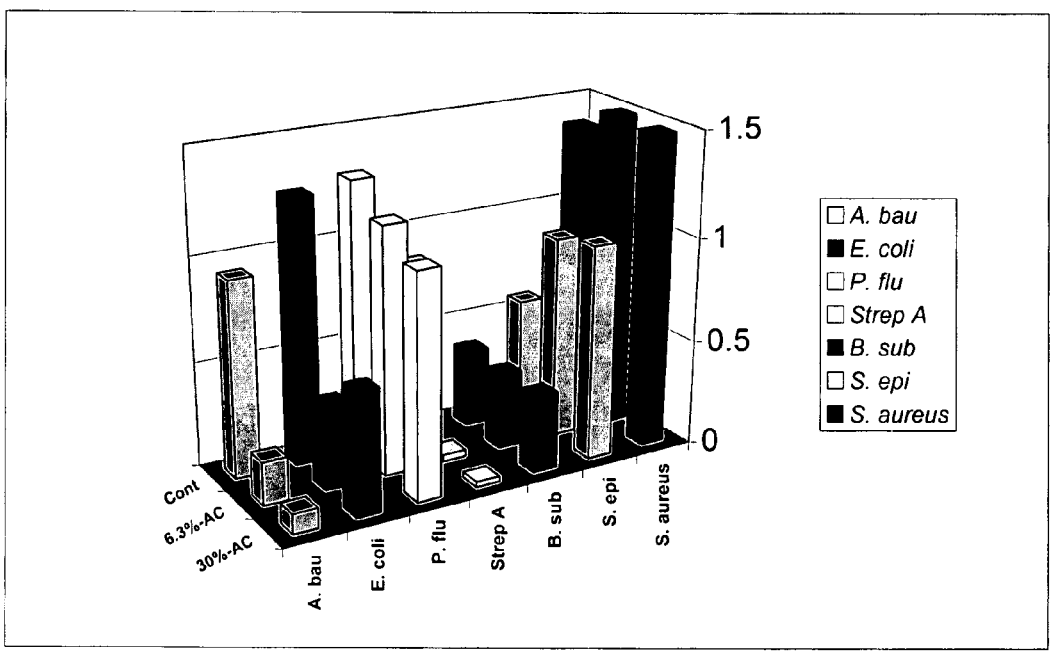
FIG. 6(b) shows the charge density and broad spectrum antibacterial effect of chitosan-arginine (6.3% and 30% functionalized) for *A. baumannii, E. coli, P. fluorescens, S. pyogenes* (Staph A), *B. subtilis, S. epidermidis,* and *S. aureus* at 48 hrs., with a 1:50 dilution.
Figure 6C:
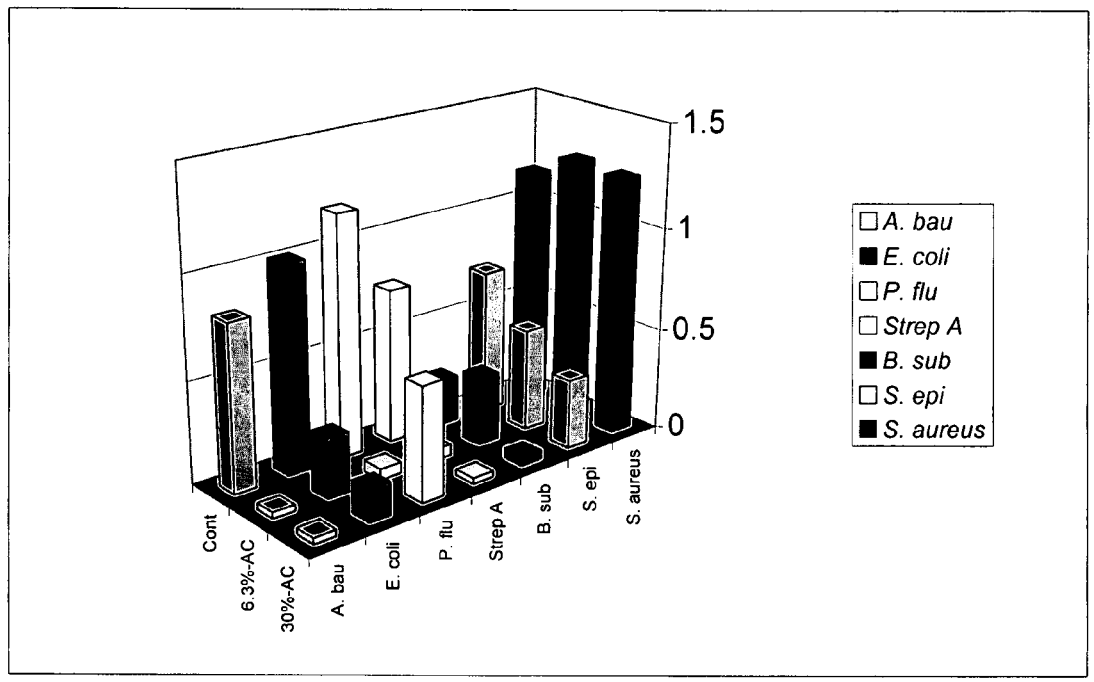
FIG. 6(c) shows the charge density and broad spectrum antibacterial effect of chitosan-arginine (6.3% and 30% functionalized) for *A. baumannii, E. coli, P. fluorescens, S. pyogenes* (Staph A), *B. subtilis, S. epidermidis,* and *S. aureus* at 24 hrs., with a 1:1000 dilution.
Figure 6D:
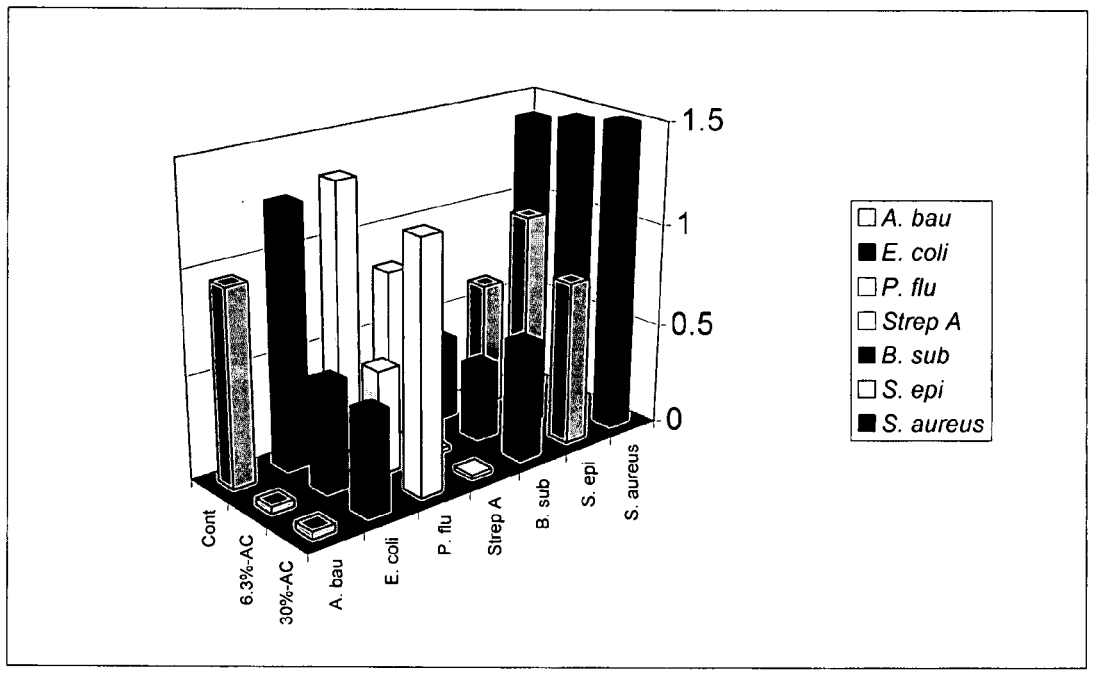
FIG. 6(d) shows the charge density and broad spectrum antibacterial effect of chitosan-arginine (6.3% and 30% functionalized) for *A. baumannii, E. coli, P. fluorescens, S. pyogenes* (Staph A), *B. subtilis, S. epidermidis,* and *S. aureus* at 48 hrs., with a 1:1000 dilution.

The efficacy of chitosan-arginine on controlling bacteria in preformed biofilms was demonstrated using liquid growth media inoculated with *S. epidermitis* in the absence of chitosan-arginine. The biofilm was allowed to form. The biofilms were grown as described above, in LB and in the absence of any AC, using either naturally occurring bacteria in produced water or a selection of biofilm-forming pathogens. After the 24 hour growth period, the planktonic bacteria were removed as above and the biofilms exposed to 5000 ppm of 30% arginine-chitosan for one hour. The chitosan-arginine was then washed off, the biofilm scraped into phosphate buffered saline (PBS) and resident bacteria re-suspended using a Dounce homogenizer. The suspended bacteria were serially diluted in PBS and plated onto LB-agar plates which then were incubated at 37° C. for 48 hours. The resulting colonies were counted and compared to the control with no exposure to chitosan-arginine. The number of viable bacteria in the treated biofilm were back-calculated and are shown in FIG. 5. As shown in FIG. 5(*a*), chitosan-arginine significantly killed over 80% in the resident preformed natural water-based bacterial film. FIG. 5(*b*) demonstrates that chitosan-arginine also kills the resident bacteria of *S. epidermidis*. The dose response of preformed biofilms of *S. aureus* is shown in FIG. 5(*c*). At doses as low at 100 ppm for 1 hr, over 60% of the bacteria in the biofilm are killed with increasing activity to >95% at 500 ppm. Thus chitosan-arginine exposure to preformed biofilms for periods as short as 1 hour had bacteriocidal activity with increasing activity at increasing doses nearing 100% at 500 ppm for *S. aureus*.

EXAMPLE 6

Bacteriocide of a Broad Spectrum of Bacteria

The bacteriocidal activity of 7% functionalized and 30% functionalized chitosan-arginine with a MW distribution between 25 kDa and 300 kDa was tested for a broad range of gram positive and gram negative bacteria including *A. baumannii, E. coli, P. fluorescens, S. pyogenes* (Staph A), *B. subtilis, S. epidermidis,* and *S. aureus.* The different efficacies of the chitosan-arginine compounds were demonstrated using a fixed concentration of the 7% and 30% functionalized chitosan-arginine for a final concentration of 100 ppm, and all bacteria were tested with a Nanopore water control. All bacteria, except *A. baumannii*, were inoculated into Luria Broth (LB) and grown overnight to saturation. *A. baumannii* was grown in Nutrient Broth; the final density is about $10^9$ ($OD_{600}$<<0.7) cells per ml for all strains tested. The fresh overnight growth was then diluted 1:50 or 1:1000 into RPMI (without serum) to the final bacterial concentration of $2\times10^7$ or $10^6$, respectively ($OD_{600}$<<0.1). Equal aliquots of the diluted bacteria were placed into wells of a 96 well tissue culture plate and the functionalized chitosan added (100 ppm). The cultures were then incubated at 37° C. with continuous shaking in the presence of 5% atmospheric $CO_2$. Bacterial growth was monitored by periodic recording of the $OD_{600}$ for the subsequent 24 and 48 hours. The results were plotted in FIGS. 6(*a*) and 6(*b*) (1:50, cell density $2\times10^7$ cells/ml) for 24 and 48 hours respectively and plotted in FIGS. 6(*c*) and 6(*d*) (1:1000, cell density $1\times10^6$ cells/ml). The data clearly shows that the majority of the gram positive strains were profoundly inhibited in growth over the 24 hour period by the presence of functionalized chitosan-arginine, with the exception of *S. aureus*. The antibacterial resistant and gram negative *A. baumannii* was dramatically inhibited by both the 7% and 30% chitosan arginine at both dilutions. It is further clear that inhibition occurred in a concentration-dependent manner, whereby the higher concentrations of chitosan-arginine inhibit bacterial growth more than the lower concentrations in most cases. Finally, it is clear that the 30% chitosan arginine has a greater growth-inhibitory effect on these bacteria than the 7% chitosan arginine, thus illustrating the dependency of the growth inhibition on the charge density on the functionalized chitosan.

EXAMPLE 7

Bacteriostasis in Cell Culture Media

Figure 7A:
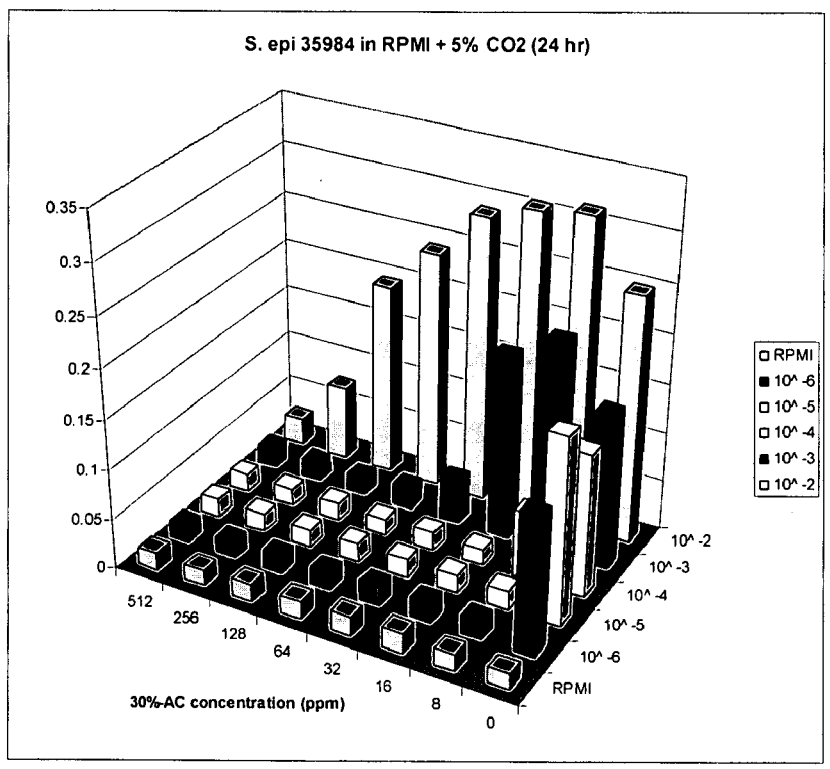
FIG. 7(a) shows the bacteriostatic effects of chitosan-arginine in cell culture media for *S. epidermidis* 35984.
Figure 7B:
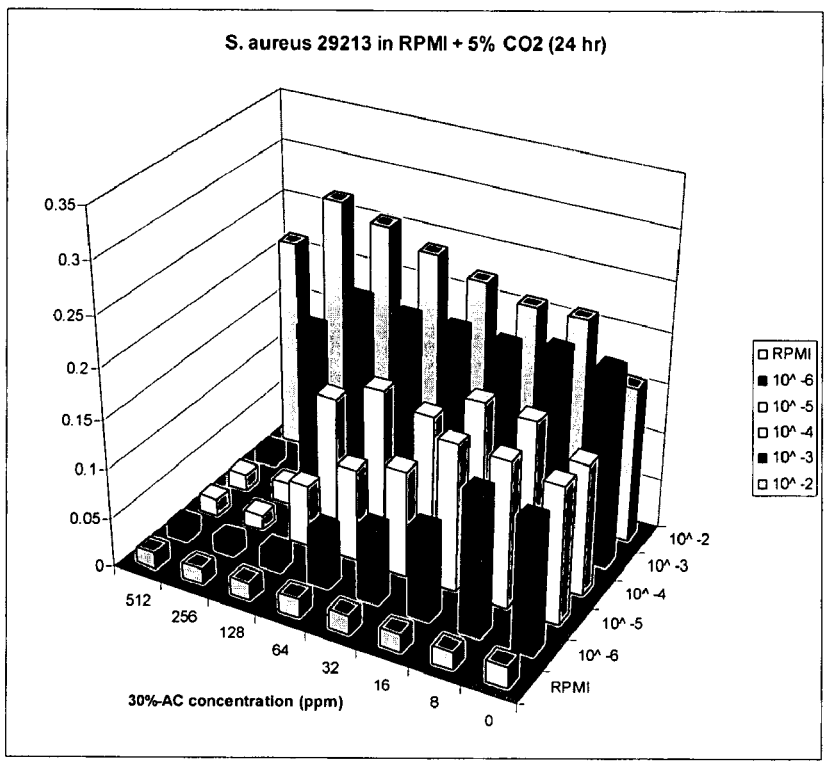
FIG. 7(b) shows the bacteriostatic effects of chitosan-arginine in cell culture media for *S. aureus* 29213.
Figure 7C:
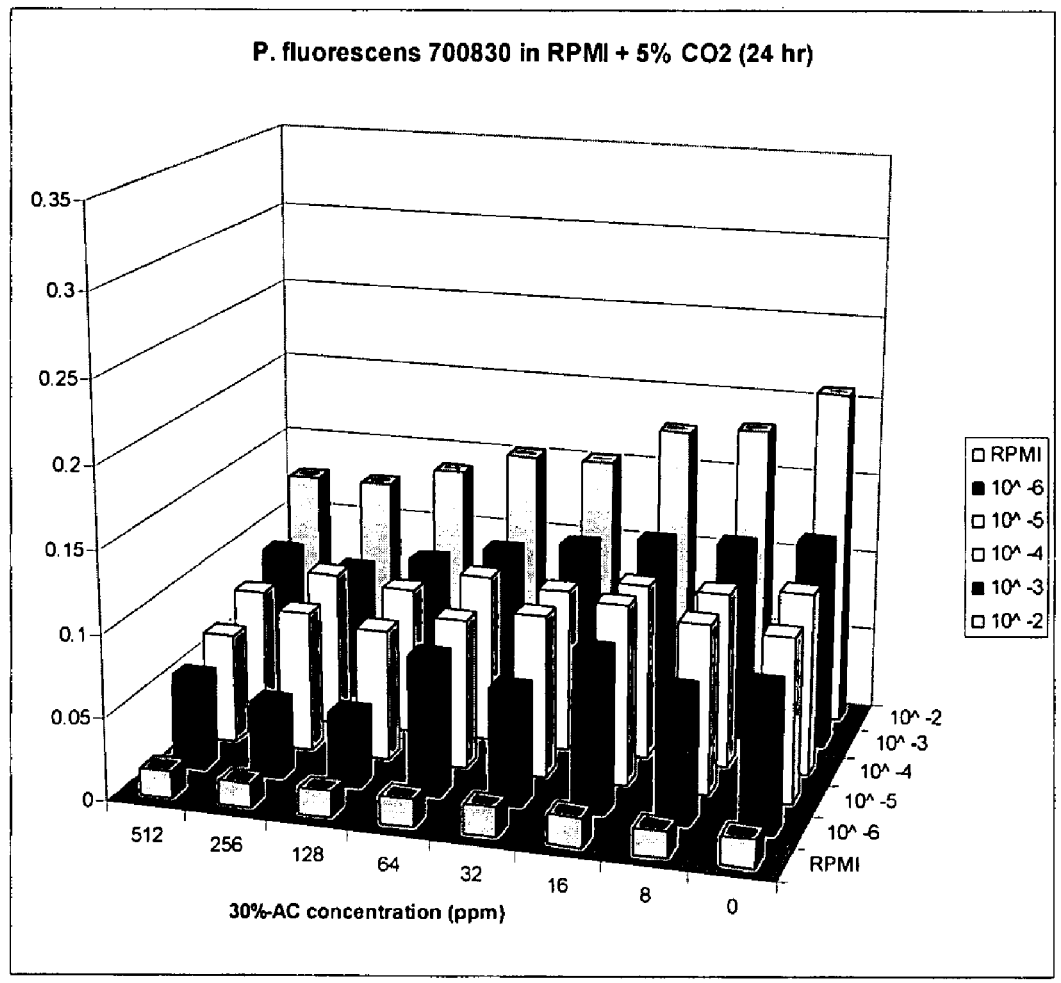
FIG. 7(c) shows the bacteriostatic effects of chitosan-arginine in cell culture media for *P. fluorescens* 700830.

Two gram positive and one gram negative bacteria (*Staphylococcus epidermidis* 35984, *Staphylococcus aureus* 29213 and *Pseudomonas fluorescens* 700830, respectively) were tested for control of growth in cell culture media, RPMI. Bacteria were inoculated into RPMI and grown overnight to saturation resulting in a final density of about $10^9$ ($OD_{600}$<<0.7) cells per mL for all strains tested. This fresh overnight growth was then diluted 1:100 ($10^{-2}$), 1:1000 ($10^{-3}$), 1:10000 ($10^{-4}$), 1:100000 ($10^{-5}$), 1:1000000 ($10^{-6}$), into RPMI to the final bacterial concentration of $10^7$, $10^6$, $10^5$, $10^4$, or $10^3$ cells/mL, respectively. Equal aliquots of thus diluted bacteria were placed into wells of a 96 well tissue culture plate and the chitosan-arginine 30% functionalized was added to the desired final concentration (0-512 ppm) with Nanopure water as the 0 dose control. The cultures were then incubated at 37° C. with continuous shaking. Bacterial growth was monitored by either periodic recording the $OD_{600}$ for the subsequent 24 hours. The results shown in FIG. 7(*a*)

demonstrates that at all but the highest concentrations of *S. epidermidis*, chitosan-arginine inhibits all growth and kills the bacteria relative to the control group. The dose response of *S. aureus* is demonstrated in FIG. 7(*b*) where at all bacterial concentrations except $10^7$ and $10^6$ cells/mL show an increasing effectiveness in bacteriostasis as the does increases from 8 ppm to 256 ppm where all cell growth is inhibited, even for the $10^6$ cells/mL. The effect of chitosan-arginine on *P. fluorescens* as demonstrated in FIG. 7(*c*) to be not as dramatic for this gram negative bacteria as for the previous two gram positive bacteria, but the dose response is much more uniform over all concentrations and shows significant inhibition of growth at all concentrations.

EXAMPLE 8

Cytotoxicity in Cell Culture Media

Figure 8A:
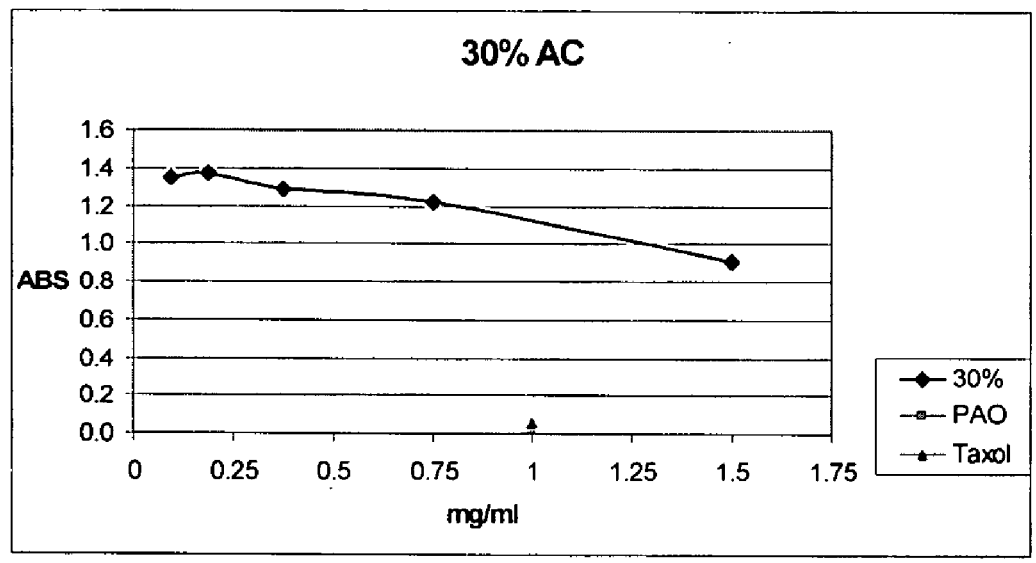
FIG. 8(a) shows the limited cytotoxic effects of chitosan-arginine ~30% on HeLa cells.
Figure 8B:
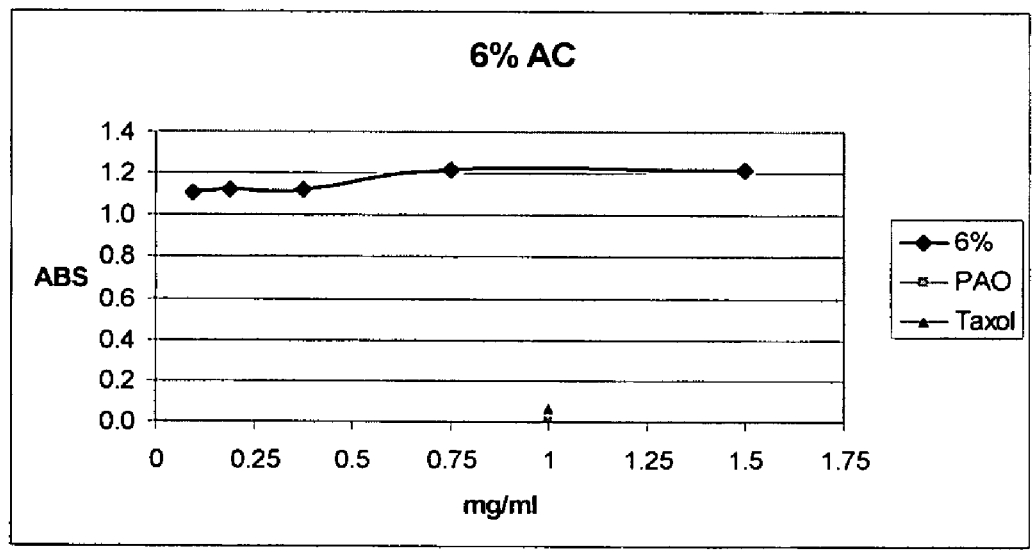
FIG. 8(b) shows the limited cytotoxic effects of chitosan-arginine 6% on HeLa cells
Figure 9A:
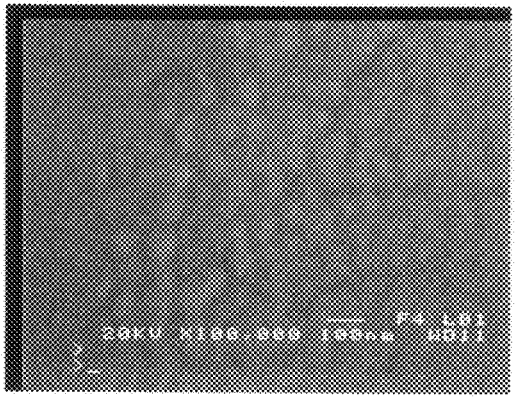
FIG. 9(a) shows an SEM image of amino-functionalized glass
Figure 9B:
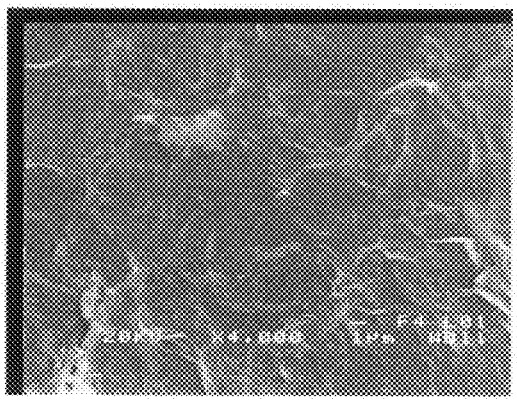
FIG. 9(b) shows an SEM image of chitosan arginine bound to amino-functionalized glass.
Figure 9C:
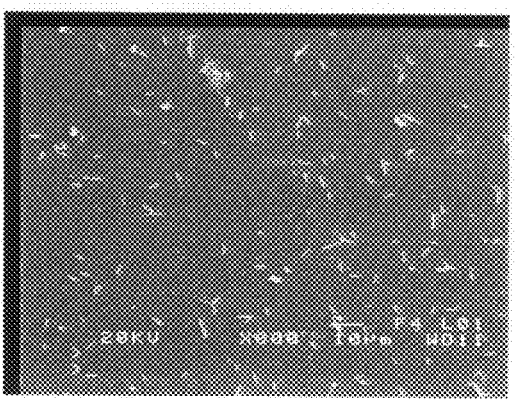
FIG. 9(c) shows an SEM image of amino-functionalized glass exposed to *Pseudomonas fluorescens*.
Figure 9D:
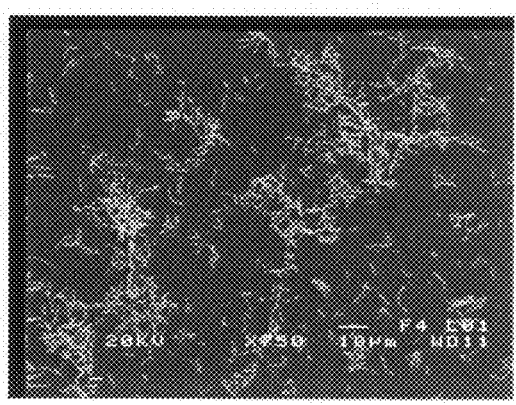
FIG. 9(d) shows an SEM image of chitosan-arginine coated glass exposed to *Pseudomonas fluorescens*.

Chitosan-arginine was used to limit bacterial contamination of mammalian cell culture. Toxicity tests of chitosan-arginine with both 7% and 30% functionalization demonstrated that these moieties were non-toxic to human cells in culture. MTT assays, which are a standard assay to determine cytotoxicity, were used on HeLa cells. HeLa (human epithelial cells) cells were plated into 96 well tissue culture plates at a final density of $5\times10^4$ cells per ml of RPMI with 10% serum and allowed to adhere to the bottom of the culture dish, overnight. The following day, the media was replaced with media containing the indicated amounts of chitosan arginine (final concentration 0-500 ppm). One micromolar phenylarsine oxide (PAO) and taxol were used as positive controls for cytotoxicity. Cells were incubated for 48 hours in 5% $CO_2$ at 37° C. At the end of the 48 hour period, MTT reagent was added to a final concentration of 0.5 mM and cells were allowed to incubate for additional 2 hours. During this period, mitochondria in the healthy cells convert the yellow MTT into dark blue formazan crystals while the dead cells are unable to do so. Media was removed and the cells & crystals dissolved with DMSO. The resulting deep blue color was measured at 490 nm using a plate reader. As shown in FIG. 8, chitosan-arginine exhibited very low toxic activity across a broad range of concentrations. The efficacy of controlling bacterial growth in cell culture media was then demonstrated using chitosan-arginine at concentrations that were sub-lethal to mammalian cells in culture. This effect is demonstrated in FIG. 8(*a*) where for the most potent chitosan-arginine (30%), 90% HeLa viability remains up to 750 ppm, well above all targeted antibacterial concentrations. Furthermore, the 7% chitosan-arginine exhibited no toxicity at any concentration up to 1500 ppm. In both cases, 1 micromolar concentration of both PAO and taxol killed ~100% of all HeLa cells.

EXAMPLE 9

Ability of Chitosan-Arginine Surfaces to Bind Bacteria (*Pseudomonas fluorescens*)

In order to demonstrate the ability of chitosan-arginine treated surfaces to bind bacteria tightly, chitosan-arginine was chemically cross-linked to glass, a surface that lends itself to electron microscopy but has minimal bacterial binding activity. Chitosan-arginine was covalently bonded to glass via the following protocol: glass slides (12 mm glass cover slips) were cleaned in ethanol for 1 hour. The glass was then air dried and flame sterilized. The glass was then "amonized" by treatment with 1% aminopropyltriethoxysilane (APTES) in acetone. After 15 minutes the glass washed with 100% ethanol and air dried. The glass was then coated with chitosan-arginine in phosphate buffered saline (1 mg/ml) in the presence of 1% glutaraldehyde. After 30 minutes, unbound material washed away with water. The chitosan-arginine (7% functionalized) on glass plates were exposed to a solution of 109 *Pseudomonas fluorescens*, rinsed with water, then treated for and subjected to scanning electron microscopy. As shown in FIG. 9(*a*), the APES modified glass is smooth whereas it is slightly rougher with rounded aggregates upon covalently binding chitosan-arginine as shown in FIG. 9(*b*). *P. fluorescens* attaches only very weakly as shown in FIG. 9(*c*). However, the binding of the rodlike and fairly uniform sized bacteria onto the chitosan-arginine modified surface is shown in FIG. 9(*d*). The density of bacteria relative to the control demonstrates the efficiency of chitosan-arginine binding of a gram-negative bacteria to a surface.

EXAMPLE 10

Loss of Viral Infectivity

In order to demonstrate chitosan-arginine's broad antiviral activity, a wide variety of viruses were tested in-vitro. The following viruses were utilized in the antiviral studies: 1) encephalomyocarditis virus (EMCV), B strain, a member of the picornavirus family which have a positive sense RNA genome, lack enveloped virions and replicate in the cytoplasm of the host. EMCV can infect a wide variety of cell types and is a model other picornaviral infections such as rhinovirus, hepatitis A, Coxsackie virus and poliovirus. 2) H1N1 influenza virus a member of the orthomyxovirus family which have a negative RNA genome, have enveloped virions and replicate in the nucleus and cytoplasm of the host cell. This is a cell culture adapted strain of H1N1 that was isolated from a clinical case of human influenza. 3) Vaccinia virus a member of the pox family, which has a dsDNA genome, enveloped virions and replicate in the cytoplasm of host cells. Vaccinia virus (VV) infects a wide variety of cells leading to a systemic infection which can be lethal. VV is the best characterized model for both small pox and monkey pox infection of humans. 4) The SP7 strain of Herpes simplex 1 (HSV1) is a member of herpes family; which has double-stranded DNA genomes, enveloped virions and replicate in both the nucleus and cytoplasm of the host cell. The SP7 strain is a neuron-virulent strain of HSV1 that was isolated from a fatal neonatal infection. In this study, $10^4$ infectious units (virions) were exposed to 30% functionalized chitosan-arginine for 15 minutes and then assayed for a loss in infectivity via standard plaque assay. The following viruses were tested: influenza A (H1, N1), vaccinia virus (Copenhagen strain), herpes simplex 1 (SP7 strain) and encephalomyocarditis virus (B strain). As shown in FIG. 10, a 2-3 fold reduction in virus titer was observed in all four viruses tested. Thus soluble chitosan-arginine inactivates both enveloped and non-enveloped viruses.

EXAMPLE 11

Inhibition of Influenza Infection of MDCK Cells

Figure 11A:
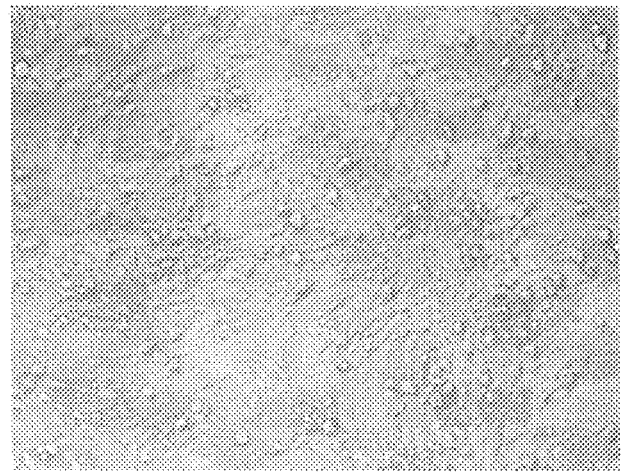
FIG. 11(a) shows the morphology of MDCK cells exposed to nonfunctionalized chitosan and influenza virus (H1, N1 [control]).
Figure 11B:
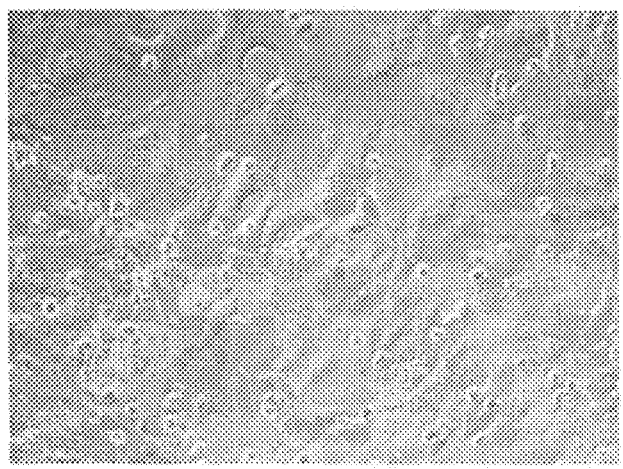
FIG. 11(b) shows the morphology of MDCK cells exposed to chitosan-arginine and influenza virus (H1, N1).
Figure 11C:
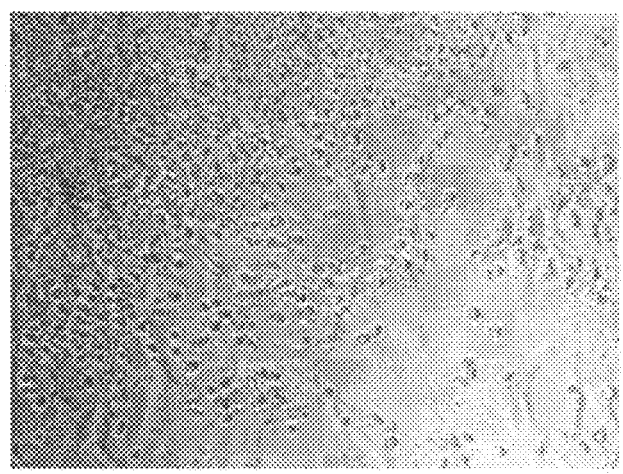
FIG. 11(c) shows the morphology of MDCK cells infected by influenza virus (H1, N1).
Figure 12:
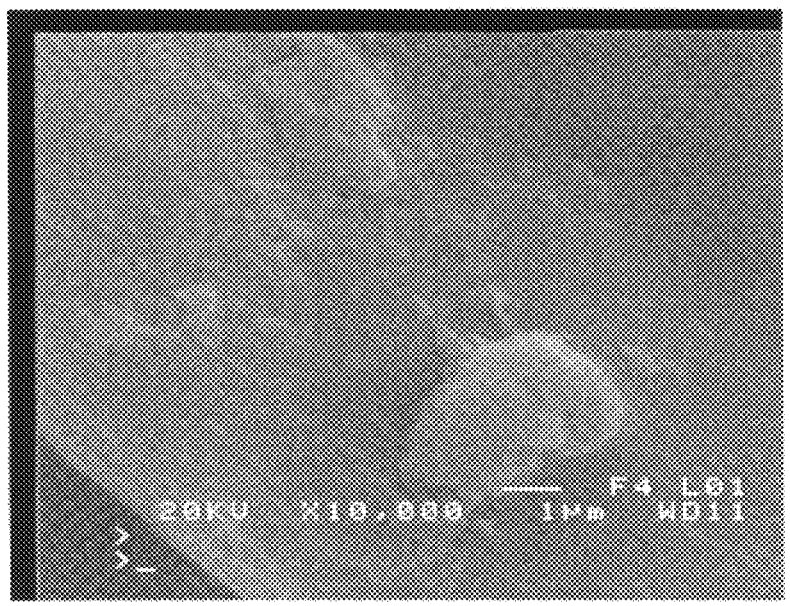
FIG. 12(a) shows amino-functionalized glass exposed to influenza virus (H1, N1).
FIG. 12(b) shows amino-functionalized glass bound to chitosan-arginine (6% functionalized).
FIG. 12(c) shows amino-functionalized glass-bound to chitosan-arginine and exposed to influenza virus (H1, N1).
Figure 12:
Figure 12E:
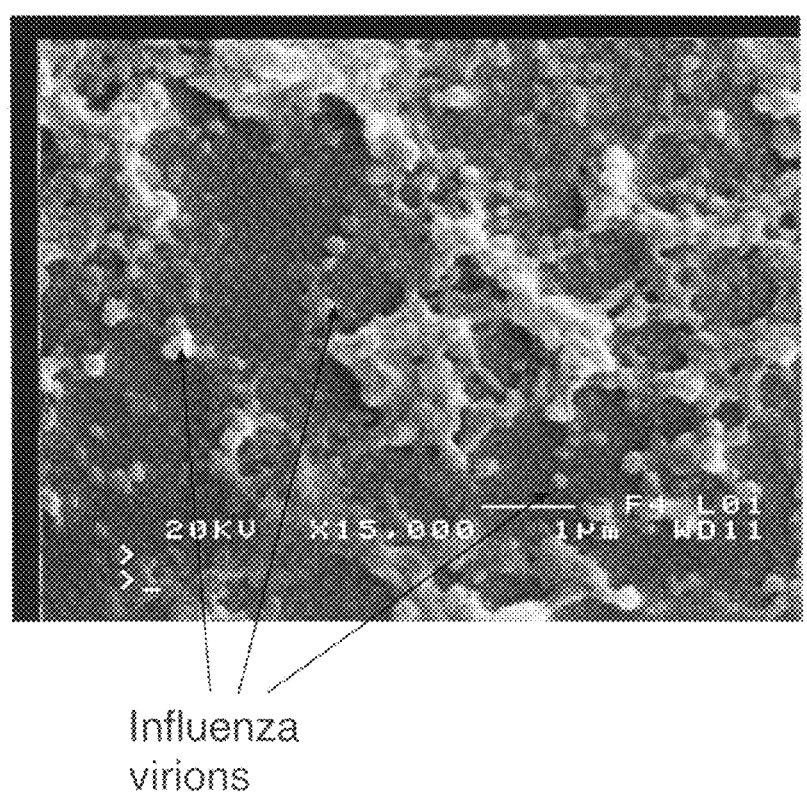
Figure 13:
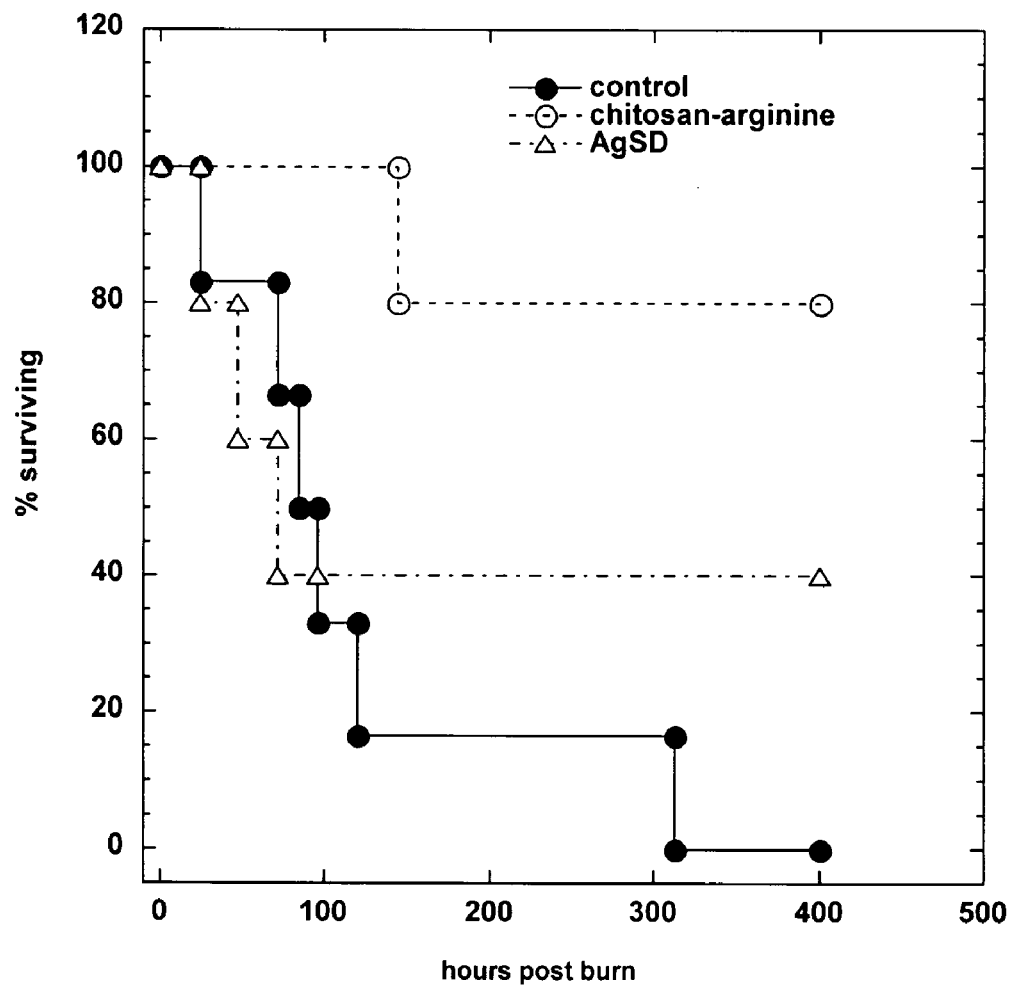
FIG. 13 shows the ability of chitosan-arginine to improve survivability by 100% in-vivo mouse $3^{rd}$ degree burns infected with *Proteus mirabilis*.

The ability of chitosan-arginine to inhibit influenza virus and thereby protect mammalian cells in culture is shown in FIG. 11. In this experiment, a known amount of influenza virions (H1, N1) was either mock treated with a control or exposed to 7% functionalized chitosan-arginine for 5 min. prior the exposing MDCK cells to the virus. The inhibitory affect of functionalized chitosan on influenza was visualized by light microscopy. When this stain of influenza virus infects MDCK cells, a characteristic cytopathic effect that includes a rounding of the infected cells, which eventually separate from and then float off the growth substrate. As shown in FIG. 11(*a*), cells that were pretreated with underivatized ultrapure chitosan had rounded indicating infection. FIG. 11(*b*) shows that MDCK cells pretreated for 5 minutes with chitosan-arginine had significantly less rounded cells and the attached monolayer, demonstrating considerably less early signs of rounding. Un-pretreated MDCK cells are infected and shown in FIG. 11(*c*) as a control for comparison.

EXAMPLE 12

Binding of Influenza

In order to demonstrate virus binding to chitosan-arginine treated surfaces, chitosan-arginine was chemically cross-linked to glass, a surface that lends itself to electron microscopy but has no appreciable viral binding activity. Chitosan-arginine was covalently bonded to glass via the following protocol: glass slides (12 mm glass cover slips) were cleaned in ethanol for 1 hour. The glass was then air dried and flame sterilized. The glass was then "amonized" by treatment with 1% aminopropyltriethoxysilane (APTES) in acetone. After 15 minutes the glass was washed with 100% ethanol and air dried. The glass was then coated with chitosan-arginine in phosphate buffered saline (1 mg/ml) in the presence of 1% glutaraldehyde. After 30 minutes, unbound material washed away with water. The chitosan-arginine (7% functionalized) on glass plates were either exposed to $10^4$ influenza virions or mock treated and then subjected to scanning electron microscopy. The 7% chitosan-arginine had broad molecular weight distribution between 25 kDa and 350 kDa. All substrates were exposed to $10^4$ influenza H1N1 virions for 15 min., washed with isotonic buffer, and then subjected to electron microscopic analysis to detect virion binding. Mock binding followed the same procedure in the absence of virions. As Seen in FIG. 12(*a*), the mock modified glass with only APTES did not bind influenza virions. The morphology changes associated with chitosan-arginine binding on the surface were generally minimal with an occasional aggregate as shown in FIG. 12(*b*). The binding of the spherical and fairly uniform sized virions onto the chitosan-arginine modified is shown in FIG. 12(*c*). The density of virions relative to the controls demonstrates the efficiency of chitosan-arginine binding of viral particles.

EXAMPLE 13

Treatment of Infected 3$^{rd}$ Degree Burns in Mice

Mice were given a ~1 $cm^2$ 3$^{rd}$ degree dorsal burn that was immediately contaminated with $10^8$ *Proteus mirabilis*. Mice were treated daily with 100 μL of 1% solution of 7% functionalized chitosan-arginine dissolved in water, treated with a uniform coating of silver sulfadiazine cream to coat the surface of the wound or treated with nothing. Survivability is plotted as a function of hours post burn and infection. Note that all mice without treatment succumbed and died. With the standard of care treatment of silver sulfadiazine cream, 40% of the mice survive after 400 hours whereas with the chitosan arginine, 100% improvement is observed and 80% of the mice survive.

(B) Chitosan-unnatural Amino Acid Compounds:

Additional control of the selectivity of chitosan-derivative compounds is achieved by functionalization of the chitosan backbone, (7), below, where X' compounds are unnatural amino acid shown in structures (8a) through (8c) and their guanidinylated counterparts as shown in (9a) through (9c), where r is an integer from 1-8. The amine in (8a) through (8c) is protonated as in (2). The guanidine in (9a) through (9c) is protonated as in (3). The position of X' is independent of distribution along the backbone and m is 0.02-0.50, related to the degree of functionalization of the primary amines. The subscripts p and q represent the degree of deacetylation such that q is between 0.50 and 0.01. In a preferred embodiment q is less than 0.20. The sum p+q+m=1 and s=1. Note that not all of the monomers on the chitosan backbone are deacetylated. Given a particular degree of deacetylation the number of free amines is calculated. Upon reaction with the unnatural amino acid, the degree of functionalization is determined relative to the number of free amines and is presented as a percent, $m/(1-q)\cdot 100\%$. The unnatural amino acid structures as taught by the present invention are distinguished from arginine by having a different carbon chain length. The variation in r provides control of the location of the charge relative to the chitosan backbone. The choice of an amine terminal group as shown here in (8a) through (8c) or a guanidine terminal group as shown here in (9a) through (9c) provides control of charge distribution. The unnatural amino acid structures are also distinguished from the arginine by having either a single charge on a amine at the terminal end of an amino acid or as a broad charge distribution on a resonant guanidinyl group as shown in (2) and (3), above.

(7)

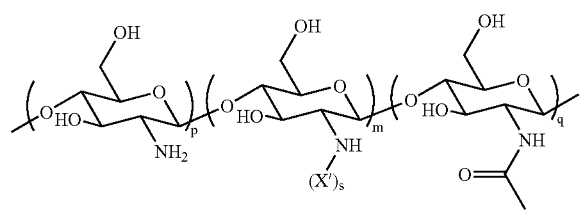

Where X' is (8a)

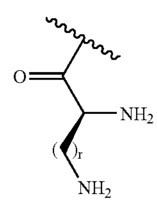

(8b)

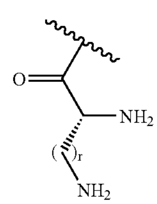

(8c)

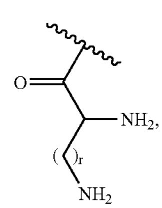

or

-continued

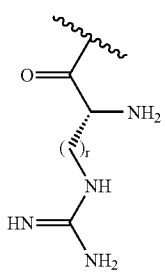

(9a)

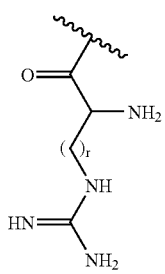

(9b)

(9c)

For non-boc-boc-protected unnatural amino acids with terminal amines as shown in (8a) through (8c), above and non-boc-protected unnatural amino acids with terminal guanidines as shown in (9a) through (9c), above, polyamino acid functionalization is as shown in (7) above; where s, a polymerization factor, is between 1 and 10, as described by comb-like polymers with up to 50% of the total MW fulfilled by X'. One of ordinary skill in the art will recognize that the functionalized chitosans will have an average degree of functionalization and polymerization and can polymerize through the alpha amine and/or the terminal amine. The polymerization factor, s, thus need not be an integer, as s is averaged over m reactive sites.

Related chitosan-L/D unnatural amino acid compounds include but are not limited to 2,3-diaminopropionic acid; 2,4-diaminobutyric acid; 2,5-diaminopentanoic acid (ornithine) and their guanidinylated derivatives.

(C) Chitosan-acid-amine Compounds:

For the purposes of distinguishing the chitosan acid-amine derivative compounds from the relevant chitosan-amino acid derivative compounds, acid-amine compounds include both and acid and an amine. In order to functionalize chitosan with an acid-amine group, the α-amine of an amino acid requires protection in the synthesis and subsequent deprotection by an acid. Higher MW chitosan derivatives are attained by eliminating the deprotection steps. Furthermore, the α-amine does not contribute significant charge at pH 7 and supports a less reactive carboxyl group. However, the terminal amine is protected by boc before reaction. If the amine is guanidinylation, boc-protection is not necessary. Additional control of the selectivity of chitosan-derivative compounds is achieved by functionalization of the chitosan backbone by X" as shown in (10), below, where X" are acid-amines as shown in structures (11) or their related guanidinylated counterpart shown in (12), where r represents integers from 1-6. The amine in (11) can be protonated as in (2). The guanidine in (12) can be protonated as in (3). The position of X" is independent of distribution along the backbone and m is 0.02-0.50, related to the degree of functionalization of the primary amines. The subscripts p and q represent the degree of deacetylation such that q is between 0.50 and 0.01. In a preferred embodiment q is less than 0.20. The sum p+q+m=1. Upon reaction with the acid-amine, the degree of functionalization is determined relative to the number of free amines and is presented as a percent, m/(1−q)·100%. The acid-amine structures, as taught by the present invention, are distinguished from the arginine and natural and unnatural amino acids by the omission of the α-amine associated with the acid of a biologically relevant amino acid. This omission also reduces the charge at the most proximal position to the chitosan backbone. The α-amine has a pKa of ~6 so that the α-amine of functionalized natural and unnatural amino acids are only fractionally charged at physiological pH. The omission of the α-amine contributes little to the change in positive charge. The acid-amine structures are also distinguished from the arginine by having a different carbon chain length. The variation in r provides control of the location of the charge relative to the chitosan backbone. The choice of an amine terminal group as shown in (11), below, or a guanidine terminal group as shown in (12), below, provides control of charge distribution.

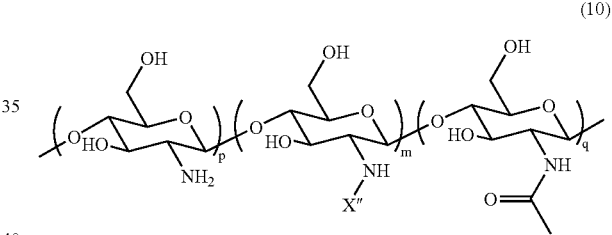

(10)

Where X" is:

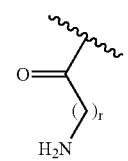

(11)

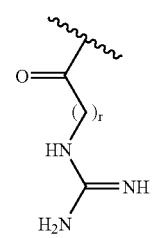

(12)

Chitosan-acid amine derivative compounds, include but are not limited to, 2-amino-ethanoic acid, 3-amino-propanoic acid, 4-amino-butanoic acid, 5-amino-pentanoic acid, 6-amino-hexanoic acid and their guanidinylated derivatives.

(D) Chitosan-natural Amino Acid Compounds:

In accordance with the present invention, additional control of the selectivity of chitosan-derivative compounds is achieved by functionalization of the chitosan backbone by X'" as shown in (13), below. In a preferred embodiment, X'"

is the charged natural amino acid lysine (pka ~10). As shown in (14a), below X''' is L-lysine and as shown in (14b), below X''' is D-lysine. Additionally X''' are also the charged natural amino acids histidine (pka ~6), aspartic acid (asp), and glutamic acid (glu). Here, m is between 0.02-0.50 and is related to the degree of functionalization relative to the number of free amines as m/(1−q)·100%. The subscripts p and q represent the degree of deacetylation such that q is between 0.50 and 0.01. In a preferred embodiment q is less than 0.20. The sum p+q+m=1 and s=1. The upper limit of functionalization is determined by both sterics and electrostatics as described above. The boc-protected amino acids are similar in size to a glucose monomer, and have some fairly extensive rotational degrees of freedom. However, the electrostatic repulsion is difficult to overcome, even in very high salt concentrations. Consequently, an upper limit of approximately 0.50 fractional functionalization is achieved.

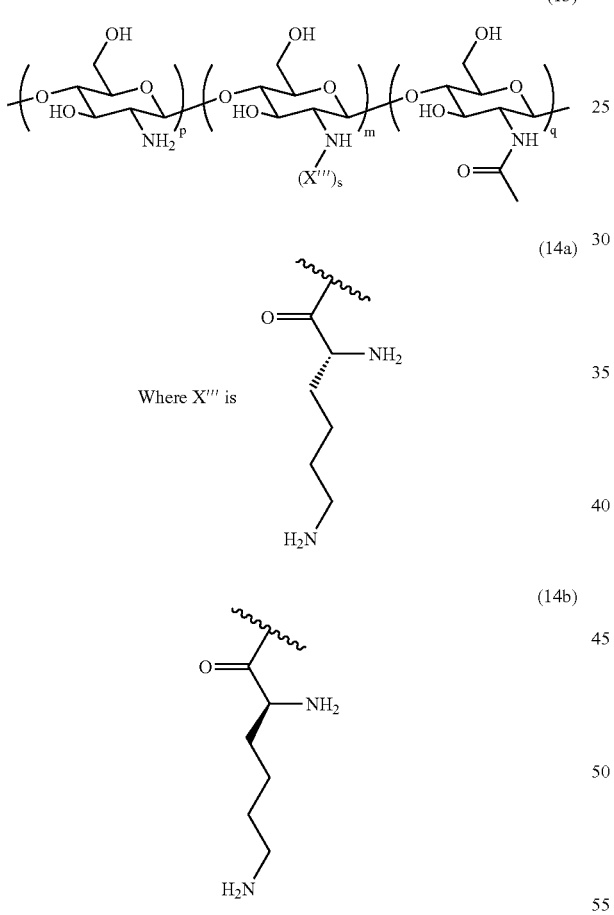

For non-boc-protected amino acids, poly amino acid functionalization is as described in (13), above, where s, a polymerization factor, is between 1 and 10 as described by comb-like polymers with up to 50% of the total MW fulfilled by X'''. One of ordinary skill in the art will recognize that the functionalized chitosans-natural amino acid compounds will have an average degree of functionalization and polymerization. The polymerization factor, s, thus need not be an integer, as s is averaged over m reactive sites.

A preferred embodiment of the present invention, shown in (15) below, is the L-stereoisomer of lysine coupled to chitosan. Here, m is between 0.02-0.50 and is related to the degree of functionalization relative to the number of free amines as m/(1−q)·100%. The subscripts p and q represent the degree of deacetylation such that q is between 0.50 and 0.01. In a preferred embodiment q is less than 0.20. The sum p+q+m=1 and s=1. The upper limit of functionalization is determined by both sterics and electrostatics as described above. The boc-protected amino acids are similar in size to a glucose monomer, and have some fairly extensive rotational degrees of freedom. However, the electrostatic repulsion is difficult to overcome, even in very high salt concentrations. Consequently, an upper limit of approximately 0.50 fractional functionalization is achieved.

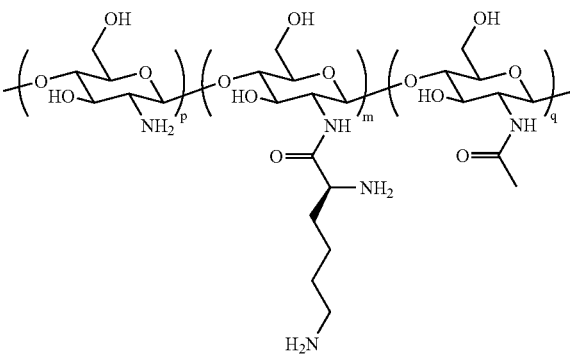

(E) Co-derivatives of Chitosan Derivative Compounds:

In accordance with the present invention, additional wound healing effects, cell stimulation and molecular tracking are achieved by functionalized chitosan-co-derivative compounds including, but not limited to, iron chelating molecules and antioxidants, as shown in (16) through (19), below. In (16), below, X is (5a), (5b) or (6), above. In (17), below, X' is (8a) through (9c), above. In (18), below, X'' is (11) or (12), above. In (19), below, X''' are the natural amino acids: lysine (pka ~10), histidine (pka ~6), aspartic acid (asp), and glutamic acid (glu). In (16) through (19), m is related to the degree of functionalization of X, X', X'', or X''' such that the degree of functionalization is reported as a percent where m/(1−q)·100%. In (16) through (19), Y includes, but are not limited to, desferoxamine (desferrioxamine), alpha hydroxy acids, poly alpha hydroxy acids, retinol, alpha lipoic acid, flavinoids, coenzmye Q, Q10, fluorescein, Texas Red, rhodamine, Prodan, polypeptides and chemical cellular growth factors. Y also includes, but are not limited to, lysine (lys), histidine (his), aspartic acid (asp), glutamic acid (glu), alanine (ala), aspargine (asn), glutamine (gln), methionine (met), proline (pro), threonine (thr), serine (ser), tyrosine (tyr), and cysteine (cys). Additionally, Y is a naturally hydrophobic or weakly hydrophobic amino acids including, but not limited to, tryptophan (trp), phenylalanine (phe), valine (val), leucine (leu) and isoleucine (ile) where X≠Y and X'''≠Y. Y is selected such that it is insoluble until in the lowest physiologically applicable pH. As understood by one of ordinary skill, Y is not limited to above compounds but includes others in this class of compounds. In (16) through (19), n is related the degree of functionalization of Y such that the degree of functionalization is reported as a percent where n/(1−q)·100%, where n is 0.001 to 0.10; p and q represent the degree of deacetylation such that q is between 0.50 and 0.01. In a preferred embodiment q is less than 0.20 and p+q+m+n=1.

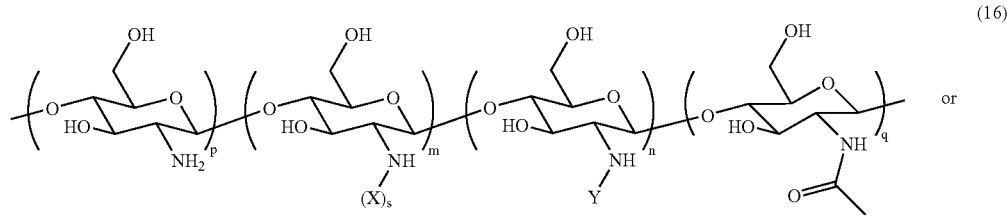

(16)

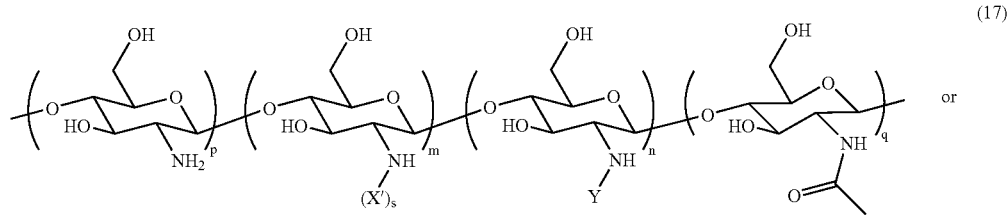

(17)

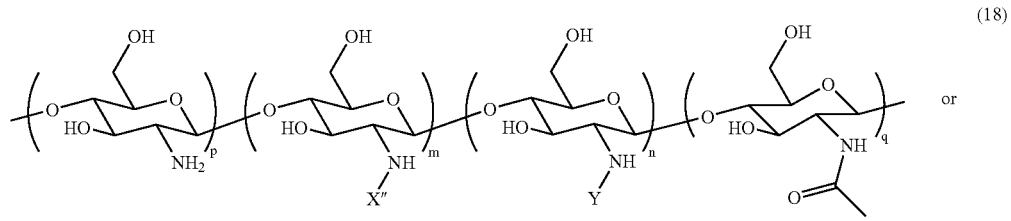

(18)

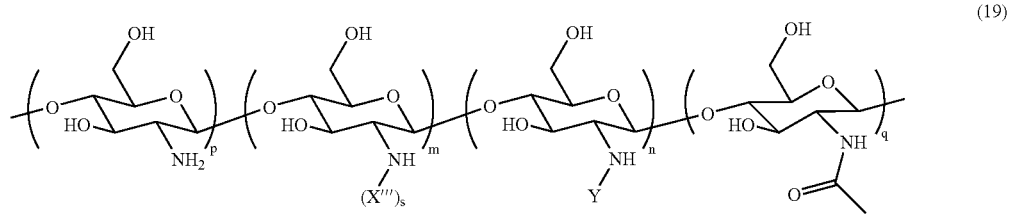

(19)

Co-derivatives of the above defined chitosan-derivative compounds include but are not limited to desferoxamine (desferrioxamine), alpha hydroxy acids, poly alpha hydroxy acids, retinol, alpha lipoic acid, flavinoids, coenzmye Q, Q10, fluorescein, Texas Red, rhodamine, Prodan, cellular growth factors, iron chelating agents, antioxidants, indicating fluorescent markers, cell growth factors and the natural amino acids listed above;

(F) Salts of Chitosan Derivative Compounds and of Co-derivatives of Chitosan Derivative Compounds:

In accordance with the present invention, salts of the chitosan-derivative compounds taught in (A) through (D), above, and salts of the chitosan-co-derivative as taught in (E), above, are precipitated with an anionic counterion to form the compounds shown in (20) through (27), below. Solid chitosan derivative compounds as shown in (4), (7), (10) and (13) are precipitated with an anionic counterion as shown in (20) through (23), where the counterion Z includes, but is not limited to chloride, hydroxide, phosphate, carbonate, acetate, lactate, citrate, cinnamate, oxalate, glutamate in ratios equivalent to or greater than the positive charge on the chitosan. For chitosan-derivative compounds having a degree of polymerization, $s=1$, $a=1$. For derivatives where $s>1$, a is a scaling factor that depends on the pH and the pKa of the functionalizing molecule and is equally balanced by the counterion charge.

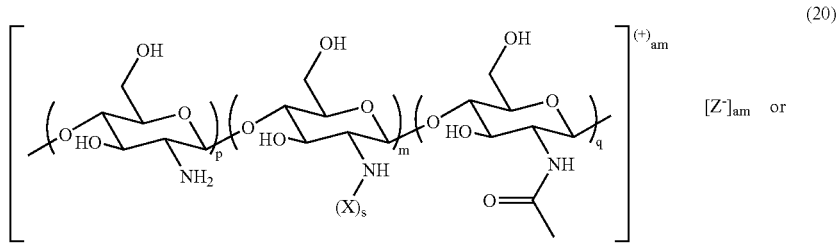

(20)

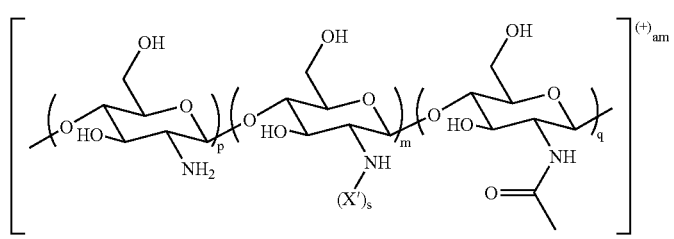
(21)
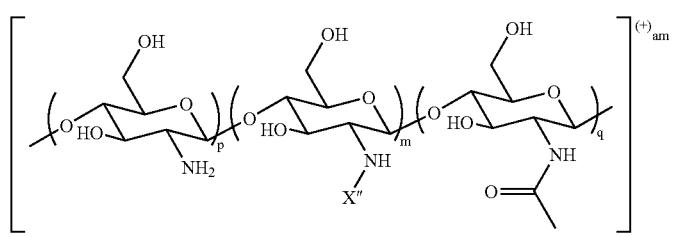
(22)
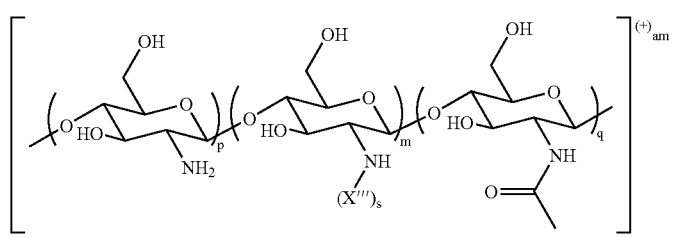
(23)
Solid chitosan-derivative compounds as shown in (16) through (19), above, are precipitated with an anionic counterion as shown in (24) through (27) where the counterion Z includes, but is not limited to, chloride, hydroxide, phosphate, carbonate, acetate, lactate, citrate, cinnamate, oxalate, glutamate in ratios equivalent to or greater than the positive charge on the chitosan.
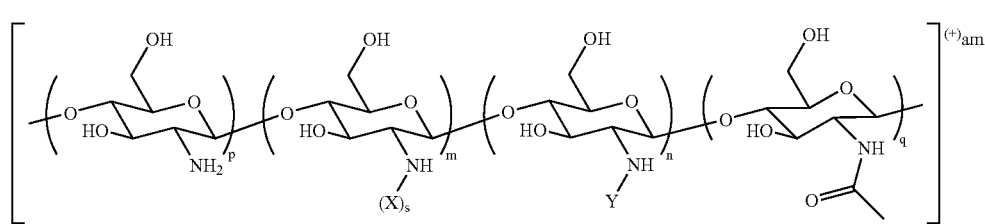
(24)
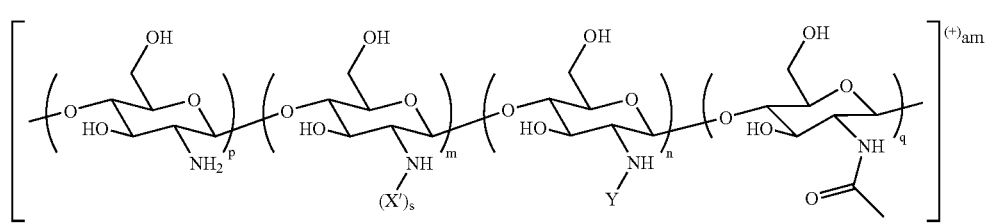
(25)
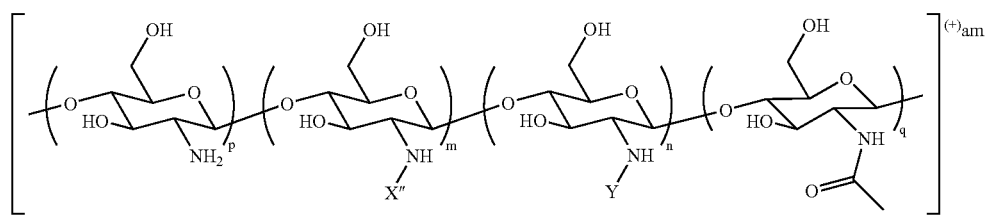
(26)

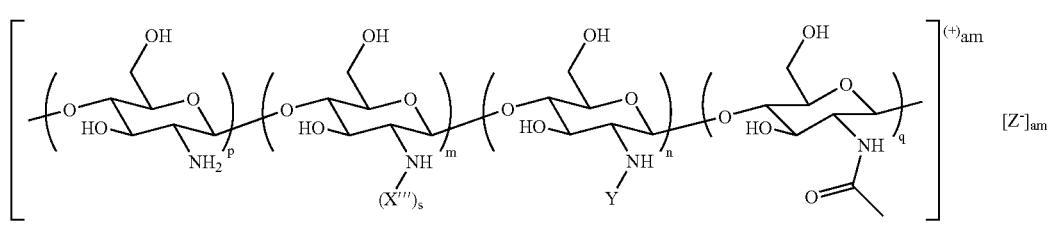

(27)

The chitosan-derivative compounds are synthesized with modifications to known standardized aqueous phase peptide coupling schemes that are, in turn, known variations of organic based synthetic schemes. As is understood by one of ordinary skill, the selection of coupling techniques is dictated by the unique solubility properties of chitosan relative to polypeptides and other acid-amines, and the requirements for biocompatible solvents. In particular, chitosan is insoluble in organic solvents and most aqueous solutions. It is most soluble in acetic acid, which is incompatible with the amino acid peptide coupling schemes as its carboxylate group would react. Chitosan is similarly mostly insoluble in a variety of non-carboxylate acids, inorganic acids, unless at high acid concentrations. Chitosan is reacted in hydrochloric acid. The preferred protocol involves solubilizing the chitosan in HCl at a pH of 2-3 and adding sodium hydroxide (base) until the pH is 5-7. When the pH is increased rapidly, the amines on the chitosan are fractionally deprotonated; however, the chitosan remains solvated for a limited time as the kinetics of precipitation for this highly solvated polyelectrolyte are very slow. Consequently, the deprotonated amines are available to react with the electrophilic carboxyl group that has been activated by the coupling agents. The methodology for forming the chitosan-arginine compounds and the chitosan-derivative compounds and the reaction pathway for the compounds is discussed below.

The amino acids in the above-described compounds, natural and unnatural, are either D or L. The naturally occurring amino acids have L stereochemistry. Naturally occurring enzymes do not have activity relative to the D stereochemical amino acids. Consequently, chitosan-derivative compounds where X or X''' is a D-amino acid will not be degraded by naturally occurring enzymes. The resistance to degradation results in longer activity of the chitosan-derivative compounds.

Salts of above defined chitosan derivative compounds include but are not limited to chloride, hydroxide, phosphate, carbonate, acetate, lactate, citrate, cinnamate, oxalate, glutamate (G) Chitosan-guanidine and Related Chitosan-guanidine Derivatives The chitosan-derivative compounds of the present invention include chitosan-guanidine and related chitosan-guanidine derivative compounds. Chitosan-guanidine is shown in (28), below, where the guanidinyl group can be protonated as shown in (3). The position of each of the m monomers with the guanidine functionalized primary amine is distributed along the chitosan backbone where m is 0.02-0.75, related to the degree of functionalization of the primary amines. In (28), p and q represent the degree of deacetylation such that q is between 0.50 and 0.01 and the position of each of the p or q monomers is distributed along the backbone. In a preferred embodiment q is less than 0.20. The sum p+q+m=1. Note that not all of the monomers on the chitosan backbone are deacetylated. Given a particular degree of deacetylation the number of free amines is calculated. The degree of functionalization is determined relative to the number of free amines and is presented as a percent, $m/(1-q) \cdot 100\%$. The upper limit of functionalization is determined by both sterics and electrostatics as discussed above. The guanidinyl group is relatively small. However, the distributed positive charge with its extensive resonance over three atoms as shown in (3) provides an electrostatic repulsion that is difficult to overcome, even in very high salt concentrations. Consequently, an upper limit of approximately 0.75 fractional functionalization is achieved. One of ordinary skill in the art will recognize that the functionalized chitosans will have an average degree of functionalization.

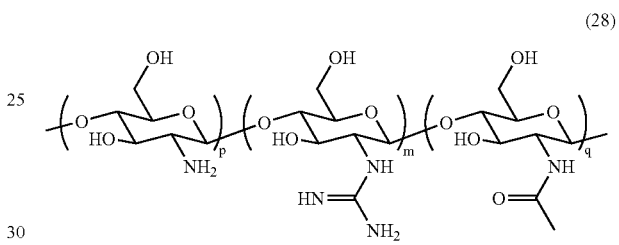

(28)

In accordance with the present invention, chitosan is functionalized with a guanidinyl group because of the stable positive charge residing on the terminal guanidinium moiety on an arginine molecule. The pKa of this species is similar to that of arginine, but are distinguished due to the need for significantly fewer chemical processing steps and the molecular weight of the material is better preserved due to the elimination of the high acid deprotection step, as discussed below. For this method of functionalization, the primary amine of chitosan is converted directly into a guanidinium ion as shown in (3). Placing this guanidinyl moiety in such close proximity to the chitosan backbone of the polymer, as shown in (28) above, mimics more closely the properties of chitosan. Particularly, at low pH where the amine is protonated, the charge is permanent and distributed for the guanidinyl moiety, rather than a point charge. The positive charge is also located very close to the chitosan backbone, and has significant antibacterial efficacy, similar to the chitosan-arginine.

Examples 14 and 15, below demonstrate in-vitro activity of chitosan-guanidine compounds. These compounds have a preferred MW between 25 kDa and 400 kDa and have broad antimicrobial activity against both gram-negative and gram-positive bacteria. Chitosan-guanidine also exhibits higher activity against gram negative bacteria than does the chitosan arginine. This is likely due to the fact that chitosan-guanidine, as shown in (28), above, has the positive guanidinium group positioned a shorter distance from the chitosan backbone and possesses a higher molecular weight than chitosan-arginine. As is understood by one of ordinary skill, the activity of chitosan-guanidine exhibits different efficacy with different bacteria.

EXAMPLE 14

Bacteriocidal Activity of Chitosan-guanidine

Both gram positive (*S. aureus*, *S. pyogenes* (Strep A), *S. epidermidis*, *B. subtilis*) and gram negative (*A. baumannii*, *P.* fluorescens and E. coli) bacteria were exposed to chitosan-guanidine (<5% functionalized and broad MW distribution having a peak near 370 kDa) in planktonic growth S. aureus, S. pyogenes (Strep A), B. subtilis, A. baumannii, S. epidermidis, P. fluorescens and E. coli were inoculated into LB (Luria Broth) (except A. baumannii which were grown in Nutrient Broth) and grown overnight to saturation resulting in a final density of about $10^9$ cells per ml ($OD_{600}$<<0.7). All strains were then diluted 1:50, mixed with or without 150 ul of 0.1% chitosan-guanidine to give a final concentration of 50 ppm and incubated at 37° C. with continuous shaking for 24 hours. OD measurements at 600 nm were used to represent relative live bacterial concentrations. The two bars in the data indicate the initial OD at 0 min that contains both live and dead cells and the OD at 30 minutes after settling which indicates the remaining live bacteria. The results of the bacteriocidal assay demonstrated in FIGS. 18(a) through 18(g) show broad efficacy for chitosan-guanidine. Chitosan-guanidine is most effective at these doses against Strep A and S. epidermidis as demonstrated in FIGS. 18(b) and 18(e). Chitosan-guanidine inhibits, but not as dramatically A. baumannii, P. fluorescens, E. coli and B. subtilis as shown in FIGS. 18(d), 18(g), 18(a) and 18(c). At these conditions, chitosan-guanidine has no inhibitory effect on S. aureus.

EXAMPLE 15

Antibacterial Activity of Chitosan-guanidine at Short Exposure Times

Figure 19A:
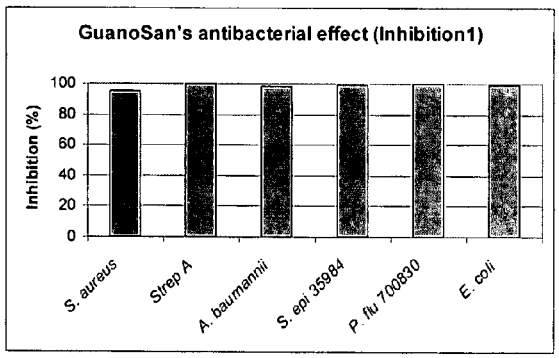
FIG. 19 (a) shows chitosan-guanidine's rapid antibacterial effect on a broad spectrum of bacteria: *S. aureus, S. pyogenes* (Strep A), *A. baumannii, S. epidermidis, P. fluorescens* and *E. coli*.
Figure 19B:
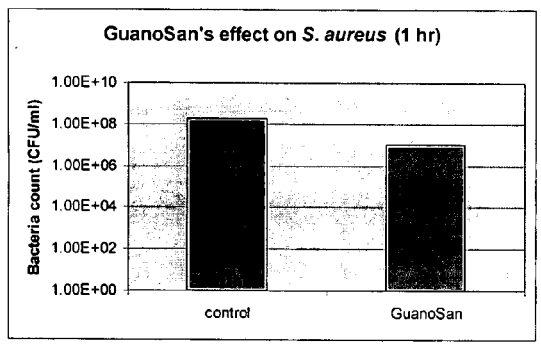
Figure 19C:
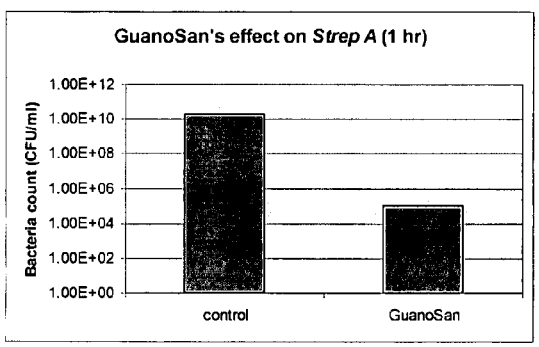
Figure 19D:
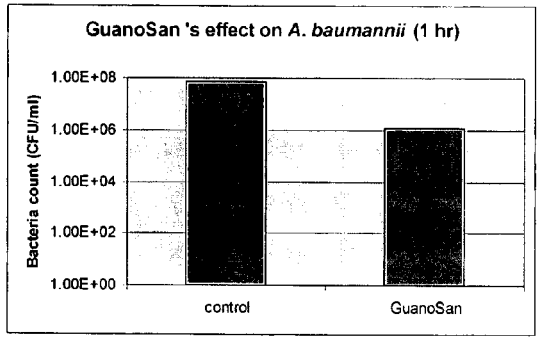
Figure 19E:
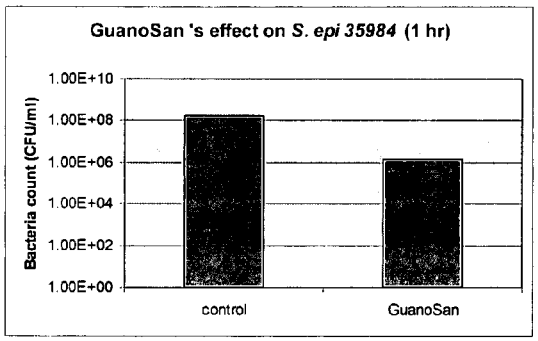
Figures 19F, 19G:
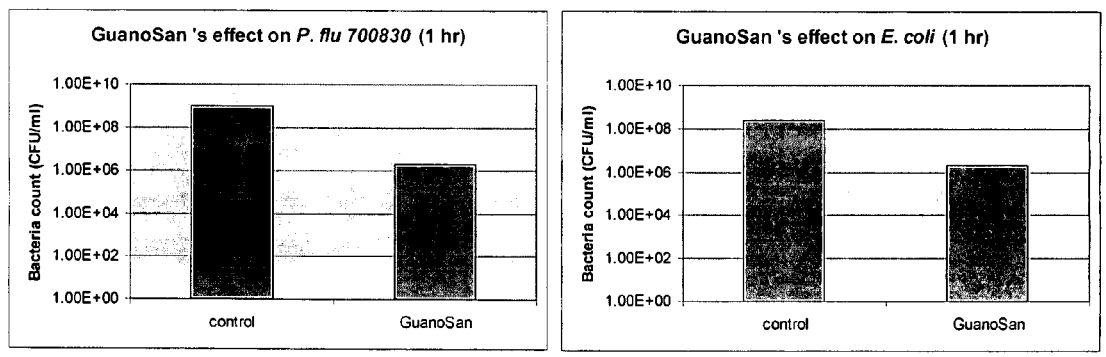

Both gram positive and gram negative bacteria were exposed to chitosan-guanidine (<5% functionalized and broad MW distribution similar to the starting material with a peak ~370 kDA). S. aureus, S. pyogenes (Strep A), A. baumannii, S. epidermidis, P. fluorescens and E. coli were inoculated into LB (except A. baumannii which were grown in Nutrient Broth) and grown overnight at 37° C. to saturation resulting in a final density of about $10^9$ cells per mL ($OD_{600}$<<0.7) for all strains tested. Cells were diluted 1:100 and were mixed with arginine-guanidine to the final concentration of 400 ppm (0.4 mg/ml), incubated at 37° C. with continuous shaking in the presence of chitosan-guanidine for one hour only, washed & serial dilutions plated onto LB-agar plates. The number of cells surviving the treatment was back-calculated from the colonies that grew on the plates within 24 hours. The percentage of inhibition was calculated and is shown in FIG. 19(a). The percentage inhibition was calculated as a percent where Inhibition %=[1−(CFU with chitosan-guanidine)/(CFU without chitosan-guanidine)]*100%. The highest inhibition rates are demonstrated for E. coli, P. fluorescens and Strep A, those which tended to be inhibited but more mildly by chitosan-arginine. Note that this level of bacteriocide occurred in only one hour treatment. The actual colony counts used to produce the summary chart for S. aureus, S. pyogenes (Strep A), A. baumannii, S. epidermidis, P. fluorescens and E. coli are demonstrated in FIGS. 19(b) through 19(g), respectively against their controls without exposure to chitosan guanidine.

In view of examples 14 and 15 above, and in accordance with the present invention, chitosan-guanidine has a higher molecular weight, lower charge density and charge closer to the backbone than chitosan-arginine. Its efficacy against gram negative bacteria is mildly superior to that of chitosan-arginine and provides the complement in activity to the chitosan-arginine derivatives. As is understood by one of ordinary skill, control of microbial populations in a variety of environments is achieved by selective application of the chitosan-derivative compounds of the present invention.

Additional wound healing effects, cell stimulation and fluorescent tracking are achieved by the functionalized guanidine-chitosan compounds shown in (29) below, having a co-derivative Y that is a iron chelating molecule or an antioxidant. In (29) below, the degree of guanidine functionalization is reported as a percent where m/(1−q)·100%.

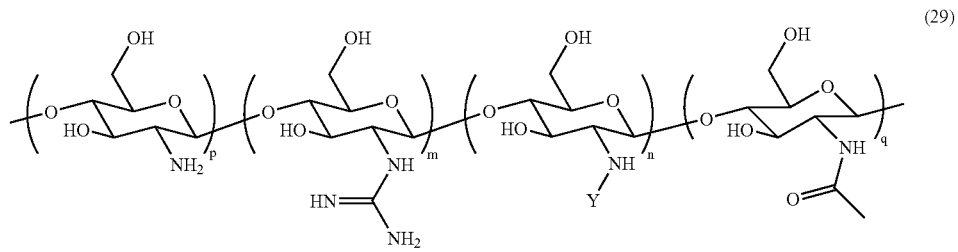

(29)

In (29), Y includes, but are not limited to, desferoxamine (desferrioxamine), alpha hydroxy acids, poly alpha hydroxy acids, retinol, alpha lipoic acid, flavinoids, coenzmye Q, Q10, fluorescein, Texas Red, rhodamine, Prodan, polypeptides and chemical cellular growth factors. Y also includes, but are not limited to, lysine (lys), histidine (his), aspartic acid (asp), glutamic acid (glu), alanine (ala), aspargine (asn), glutamine (gln), methionine (met), proline (pro), threonine (thr), serine (ser), tyrosine (tyr), and cysteine (cys). Additionally, Y is a naturally hydrophobic or weakly hydrophobic amino acids including, but not limited to, tryptophan (trp), phenylalanine (phe), valine (val), leucine (leu) and isoleucine (ile). As understood by one of ordinary skill, Y is not limited to above compounds but includes others in this class of compounds.

In (29), n is related the degree of functionalization of Y such that the degree of functionalization is reported as a percent where n/(1−q)·100%. The subscript n is 0.001 to 0.10. The subscripts p and q represent the degree of deacetylation such that q is between 0.50 and 0.01. In a preferred embodiment q is less than 0.20 and p+q+m+n=1.

Solid chitosan guanidine compounds and chitosan-guanidine co-derivatives shown in (28) and (29), above, are precipitated with an anionic counterion as shown in (30) and (31), below, where the counterion Z includes, but is not limited to, chloride, hydroxide, phosphate, carbonate, acetate, lactate, citrate, cinnamate, oxalate, glutamate in ratios equivalent to or greater than the positive charge on the chitosan.

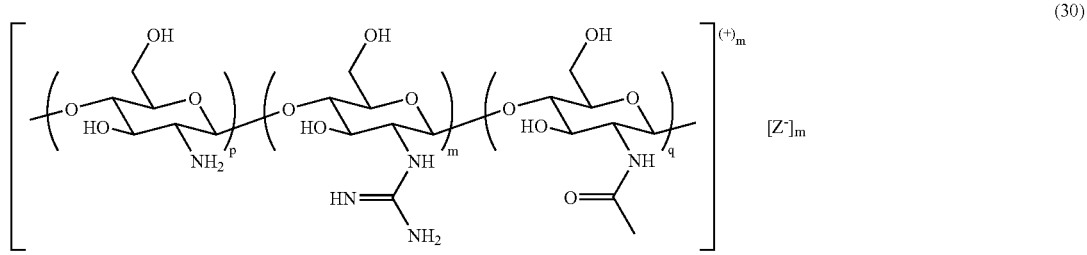

(30)

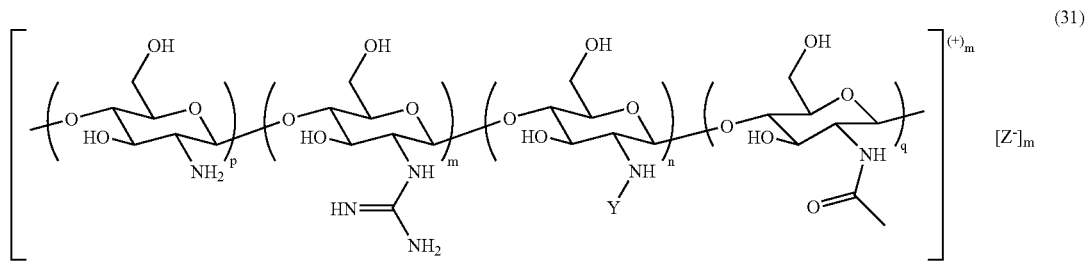

(31)

The chitosan-derivative compounds as taught in (A) through (E) above, their applications and formulations are summarized in Table III, below.

TABLE III

| Compounds | Applications | |
|---|---|---|
| | Soluble Formulations | Insoluble Formulations |
| Chitosan-derivative compounds where X is: | | |
| Arginine | Antibacterial (burns treatment) | Antibacterial coatings (including bioflim prevention) |
| Charged Amino Acids (where amino acid is D or L) including Lysine | | |
| Unnatural amino acids with amine or guanidine (where amino acids is D or L) | Antibacterial (wound treatment, prosthesis induced infections, diabetic ulcers, bedsores, lacerations, scrapes | Freeze dried sponge as absorbent for deep bacterial infection |
| Acid-amines (X = COOH —$C_r$—$NH_2$, COOH—$C_r$—($CN_3H_4$))) where r = 1-6 | | |
| Guanidine | Antibacterial for topical treatment of antibacterial resistant strains | Hydrogels (tissue engineering, cell growth, stem cell scaffold) |
| | Antibacterial in cell culture media (in particular for antibacterial resistant bacteria) | Antiviral binding surface (mask, clothing, gloves, textiles, water filter, etc) |
| | Antiviral (viral in water supplies, influenza) | |
| Chitosan-derivative compounds where X is above and Y is: | Control of microflora populations in gut | |
| desferoxamine, alpha hydroxy acids, poly alpha hydroxy acids, retinol, alpha lipoic acid, favinoids, coenzyme Q, Q10, formulation of hydroxy acids, fluorescein and other other antioxidants, fluorescent markers and the natural amino acids | Antioxidant (wound healing, cosmetic) | |
| Chitosan-derivative compounds where the counterion salt Z is: chloride, hydroxide, phosphate, carbonate, acetate, lactate, citrate, cinnamate, oxalate, glutamate and other non toxic or antioxidant counterions. | Reduction of bacteria associated with peritonitis | |
| | Control of enterophathic bacteria in the gut | |

A preferred method for synthesizing chitosan-arginine and related chitosan derivatives, in accordance with the present invention, is shown and described below:

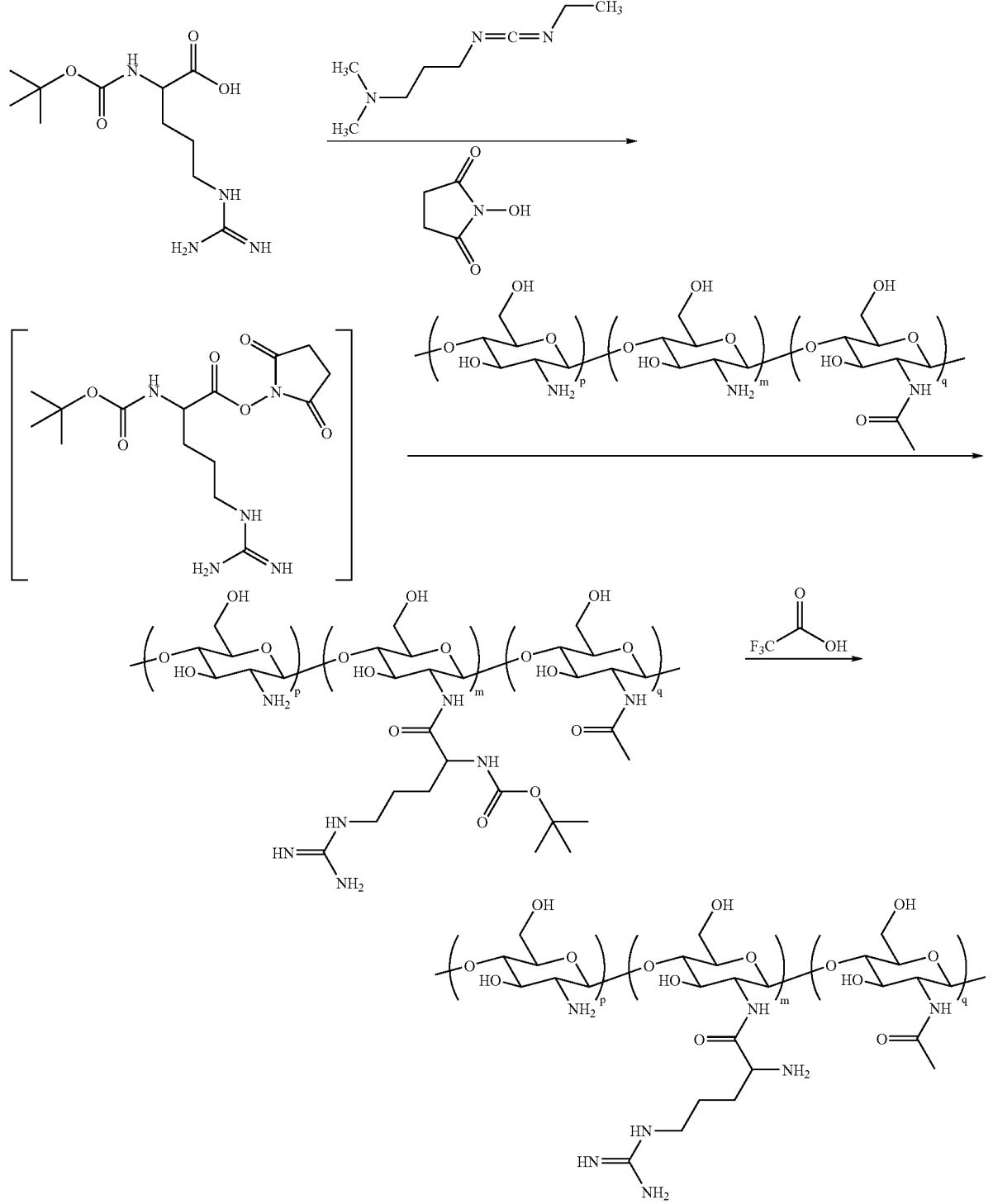

(32)

The method as shown in (32), above, utilizes N-(3-Dimethylaminopropyl)-N'-ethylcarbodiimide (EDC) and N-hydroxysuccinimide, (NHS) to activate the carboxylic acid group of singly N-Boc-protected arginine forming the N-hydroxysuccinimide ester in aqueous solution. Other protecting group/deprotection schemes include, but are not limited to, 9-fluorenylmethoxycarbonyl (FMOC) and other water soluble or solubilized benzylic esters. Other activating/coupling schemes include, but are not limited to, carbodiimides other than EDC, sulfo-NHS, 2-(1H-Benzotriazole-1-yl)-1,1,3,3-tetramethyluronium hexafluorophosphate (HBTU), 1-Hydroxybenzotriazole (HoBt). A preferred embodiment of the present invention includes the process for coupling arginine to chitosan including the steps of dissolving chitosan in aqueous acetic acid solution (HCl, pH≦5), and bringing the chitosan solution to pH 5-7 by dropwise addition of base (NaOH, 1M). When the pH is increased rapidly, the amines on the chitosan are fractionally deprotonated; however, the chitosan remains solvated for a limited time as the kinetics of precipitation for this highly solvated polyelectrolyte are very slow. Consequently, the deprotonated amines are available to react with the electrophilic carboxyl groups that have been activated by the coupling agents.

In a separate vessel, the boc-arginine is preactivated by reaction with EDC and NHS in specific ratios to the free amines on the chitosan that will determine the final arginine functionalization percent relative to the free amines on the chitosan. The formation of an amide bond between the free primary amine of chitosan and boc-arginine is dependent on the activation of the free acid, nucleophilic attack of the primary amine and the ability of the activating group to leave subsequent to the attack. Activation of the free acid is required for nucleophilic attack by the primary amine. This activation is accomplished through the use of N-(3-Dimethylaminopropyl)-N'-ethylcarbodiimide and N-hydroxysuccinimide, forming the N-hydroxysuccinimide ester in-situ followed by addition to the dissolved chitosan. It is important to note that reaction efficiency drops without sufficient pre-activation of the acid. The ratio of this activated product is directly related to functionalization of the chitosan. Using two equivalents of activated acid provides approximately 18% functionalization, while 3 equivalents (or more) provides approximately 30% functionalization. The preactivated boc-arginine is added dropwise to the chitosan solution to assure uniform distribution of the mixture into the fairly viscous chitosan solution. Note that other protecting group/deprotection schemes and other coupling/activating agents are within the scope of the present invention. The final mixture is allowed to react under ambient conditions for up to 20 hours, with vigorous shaking. Note that stirring does not suffice, as the stir bar only interacts with a small volume of the solution due to the high viscosity.

The present invention is also directed to an alternative method for making chitosan-arginine and chitosan-derivatives, as shown in (33), below. This method involves a 1-pot synthesis where higher ratios of reactants are needed to produce similar results. Chitosan solution is prepared, as indicated above, to provide soluble chitosan. Arginine, NHS and EDC are added stepwise, in ratios to amine that determine the final arginine functionalization percent relative to the free amines on the chitosan. Since the desired NHS-ester formation is the stable and reactive intermediate, arginine and NHS are added to the solution before the EDC. The EDC preactivates the carboxyl group for faster reaction with the NHS. The EDC activates the carboxyl group, but may also be hydrolyzed by water, returning the reactants to their original form. Addition of the NHS first minimizes this unwanted side reaction.

(33)

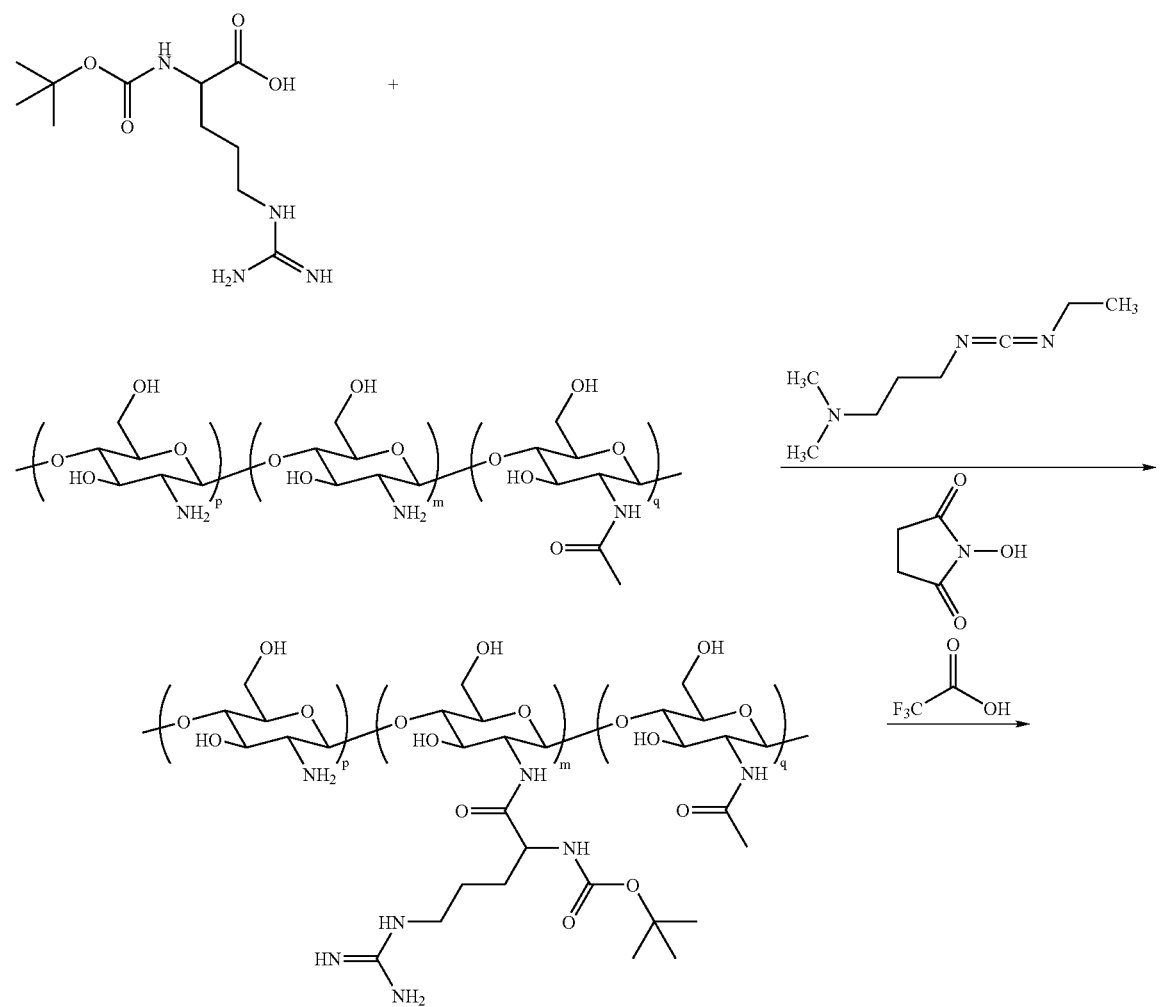

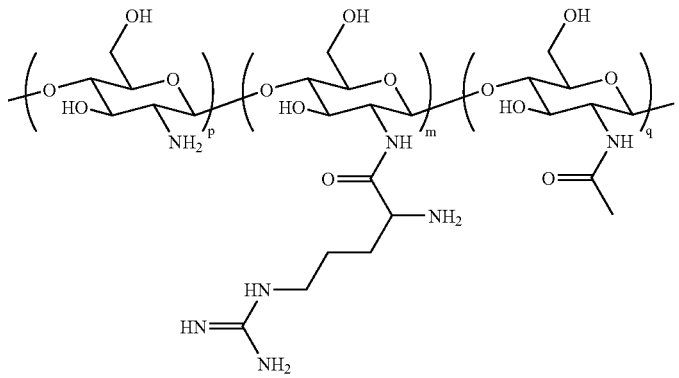

It is important to note that the chitosan-arginine coupling is optimized by the ex situ activation of the boc-arginine. To minimize organic contaminants, this reaction is performed in aqueous solution. However, this preactivation may also be conducted in organic solvents, precipitated, cleaned and the activated boc-arginine added as a solid NHS-ester. Other coupling agents include, but are not limited to, sulfo-NHS, carbodiimides and HoBt. The organic solvent include, but are not limited to, methanol, dimethylsulfoxide or dimethylformamide. The activated boc-arginine mixture is then added to a chitosan solution to initiate the coupling reaction.

In all preparations, the boc-protected chitosan conjugate is dialyzed in standard cellulose dialysis membranes with a 5000 molecular weight cut-off. The cut-off value can be varied, depending on the chitosan molecular weight desired. For these embodiments, the MW cut off is greater than 5000 Da. The use of counterions in dialysis are significant, particularly in the final dialysis step described below. In order to prevent precipitation and to assure removal of undesirable by-products such as urea and NHS that result from the first activation step, the chitosan must remain soluble for all dialysis steps. The pH does not need to be adjusted by acid because the protected boc-arginine-chitosan is soluble at pH 7. For low functionalization (below 10%), the protected boc-arginine-chitosan may be insoluble at pH 7 due to the presence of the boc group and the dialysis solution is lowered to pH 6 by HCl. The low functionalization is soluble when deprotected. The dialysis solution is changed 4 to 5 times using a volume 10-20× that of the reaction volume or until the solution ion concentration does not change. Alternatively, continuous flow ultra-filtration dialysis tubing is used. The boc-protected chitosan-arginine product is lyophilized or concentrated in a cross-flow filtration system.

Figure 14:
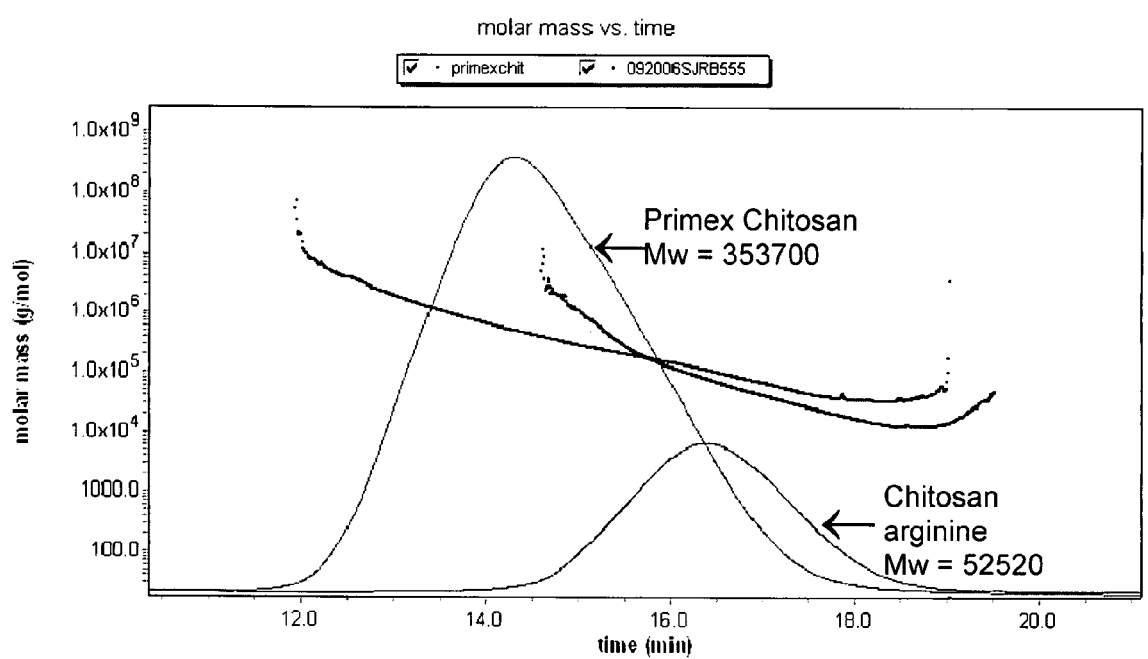
FIG. 14 shows MW data of chitosan prior to functionalization and post-arginine functionalization with 19 hours deprotection in 95% TFA.

Deprotection of the boc group from the lyophilized or concentrated product is achieved by addition of strong acid, such as trifluoroacetic acid (TFA). Other strong acids such as hydrochloric acid, hydrofluoric acid, or sulfuric acids may be used. In a preferred embodiment, the lyophilized intermediate is deprotected using a minimal volume of 95% trifluoroacetic acid, such that all of the lyophilized material is completely dissolved. In another embodiment, the concentrated intermediate is deprotected using 1M HCl. The deprotection is allowed to proceed for a variety of times between 2 and 24 hours depending on the desired molecular weight distribution of the product. Because strong acids break the glycosidic bond between monomeric units of the chitosan, the length of time exposure to such acids determines the average molecular weight and molecular weight distribution. As shown in FIG. 14, as determined by HPLC and 8-angle multi-angle light scattering with index of refraction, the size distribution of the chitosan before reaction is large and peaks at a molecular weight of 370,000 kDa. Given a 19 hr deprotection, the chitosan-arginine has a peak MW of 50,200 kDa with a high end tail trailing to the 370,000 of the parent molecule. In order to dry the chitosan-arginine, the TFA can be evaporated by blowing pure nitrogen or purified air over the solution until dry. Alternatively, the solution is neutralized by addition of NaOH until the solution is between a pH of 3 and 5. The dried residue is taken up in a HCl solution of 3 to 5 pH.

Either the dried and acidified solution or the partially neutralized solution is dialyzed using cellulose dialysis tubing as described above for two days against counterions, for example, for the chloride salt against 0.01 NaCl or HCl to assure exchange of any remaining trifluoroacetate. As is understood by one of ordinary skill in the art, any biocompatible salt is acceptable for displacement of the negative counterions, trifluoroacetate. The dialyzed chitosan-arginine is lyophilized to produce the solid product.

In a preferred embodiment, the chitosan-arginine solid product is lyophilized as the hydrochloride salt or phosphate buffer. Depending upon the intended use of the chitosan-arginine solid product, a variety of salts may be used. Common buffering salts include, but are not limited to, phosphate or carbonate. If the intended use is directed to a wound or environment where free radicals are present, the compounds containing Z antioxidant salts as described above are the preferred embodiment.

For large scale production or mass manufacture of chitosan-arginine and other related chitosan-derivative compounds requiring deprotection of an amine protecting group by strong acid, the process is simplified by the use of ultra-filtration, dialysis filtration (UFDF) in-line systems. The dialysis steps and/or lyophilization steps are replaced by UFDF. In a preferred embodiment, the protected chitosan arginine or related chitosan derivative is placed in a continuous flow UFDF against 0.01M NaCl for up to 100× the total volume of the solution. The product is lypholilized and returned to the UFDF for final filtration, dialysis and concentration.

In another preferred embodiment of the present invention, the protected chitosan-arginine or related chitosan derivative is placed in a continuous flow UFDF against 0.01M NaCl for over 100× the total volume of the solution. Lyophilization is replaced by concentration in the UFDF system, the solution is changed to 1-5M HCl for deprotection. The deprotected chitosan-derivatives are placed in gradient flow in the UFDF from 0.01M NaCl to water or Z counterions as described above for at least 100× the total volume of the solution.

Chitosan is not soluble at physiological pH; however, chitosan-arginine is soluble at pH 7. Consequently, the final dialysis step is conducted at a pH of 7. However, the pH of the final solution will not significantly affect the charge on or solubility of the chitosan-arginine to pH's above 11. A preferred embodiment of this invention is that the chitosan-arginine and chitosan derivatives have a broad range of solubility and functionality across a wide range of pH, thereby allowing it to have applications in a variety of environments. For example, antibacterial activity is preserved across the entire gut and bowel that starts acidic, as in the stomach, and becomes more basic, as in the duodenum.

The synthesis of all chitosan-derivatives follows the same methodology and coupling scheme as described for chitosan-arginine. The general scheme for synthesis of molecules with an active amine that requires boc protection to control the reaction is shown in (30). The methodology of (34), below, applies to (5a), (5b), (8a) through (8c), (9a) through (9c), and (11) as described above.

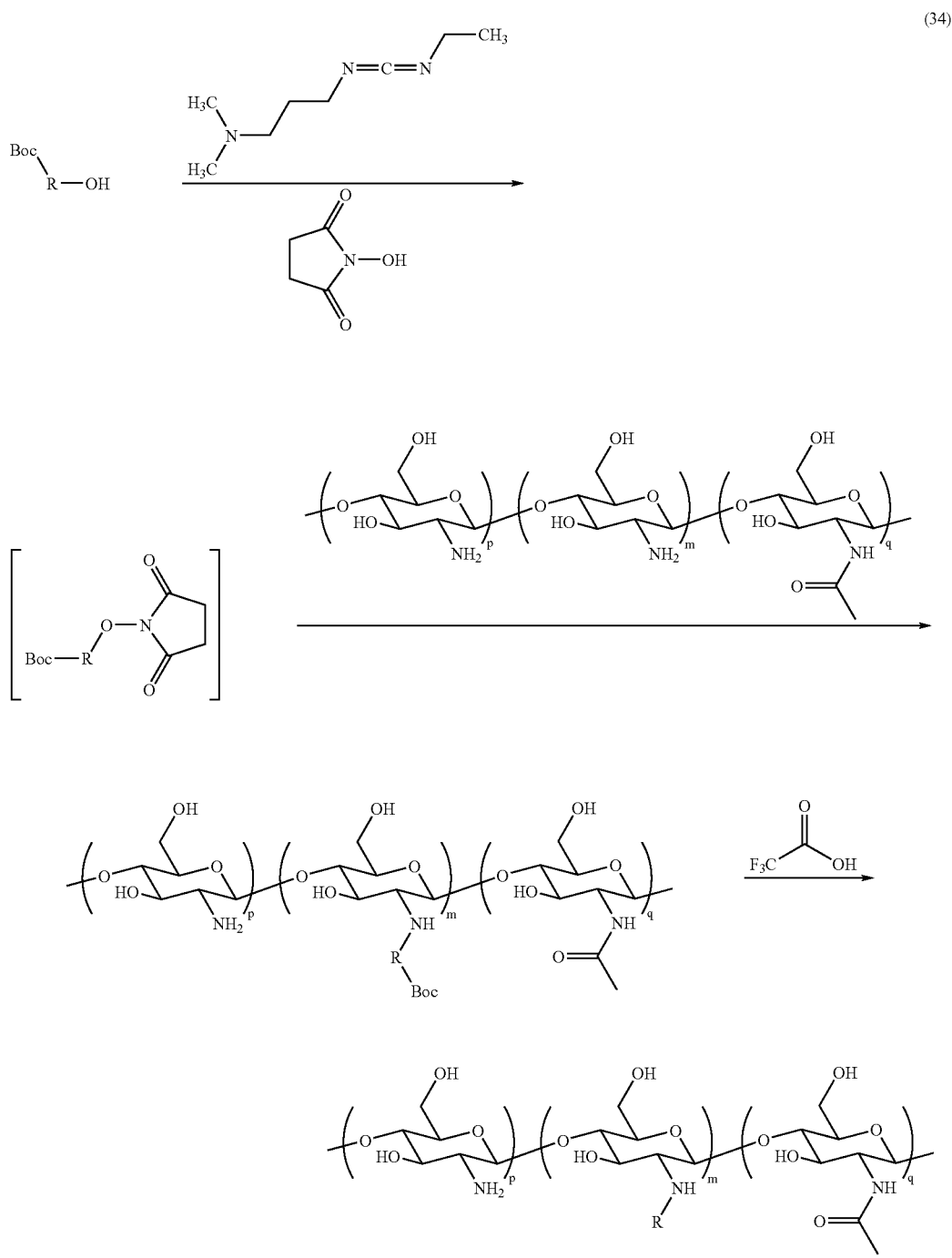

The general scheme for synthesis of molecules with a no active amine requiring chemical protection is shown in (35), below. The methodology of (35) applies to (12) as described above.

Figure 15:
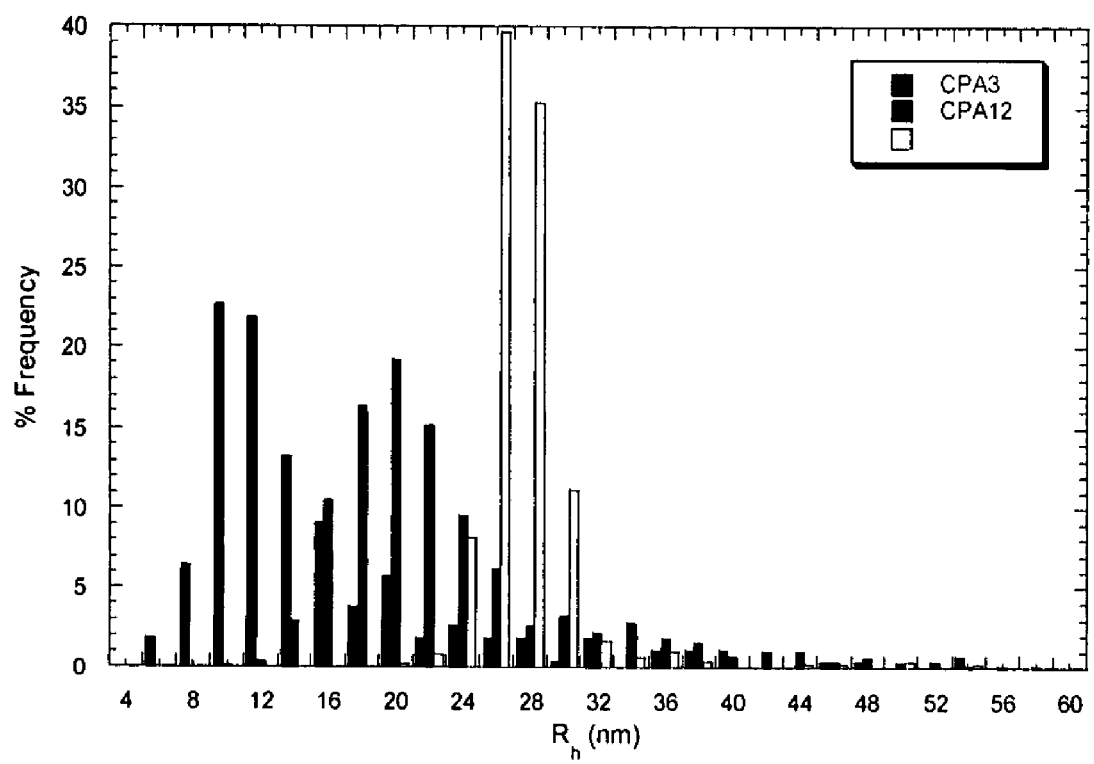
FIG. 15 shows dynamic light scattering measurements of chitosan and chitosan-arginine at different deprotection times.

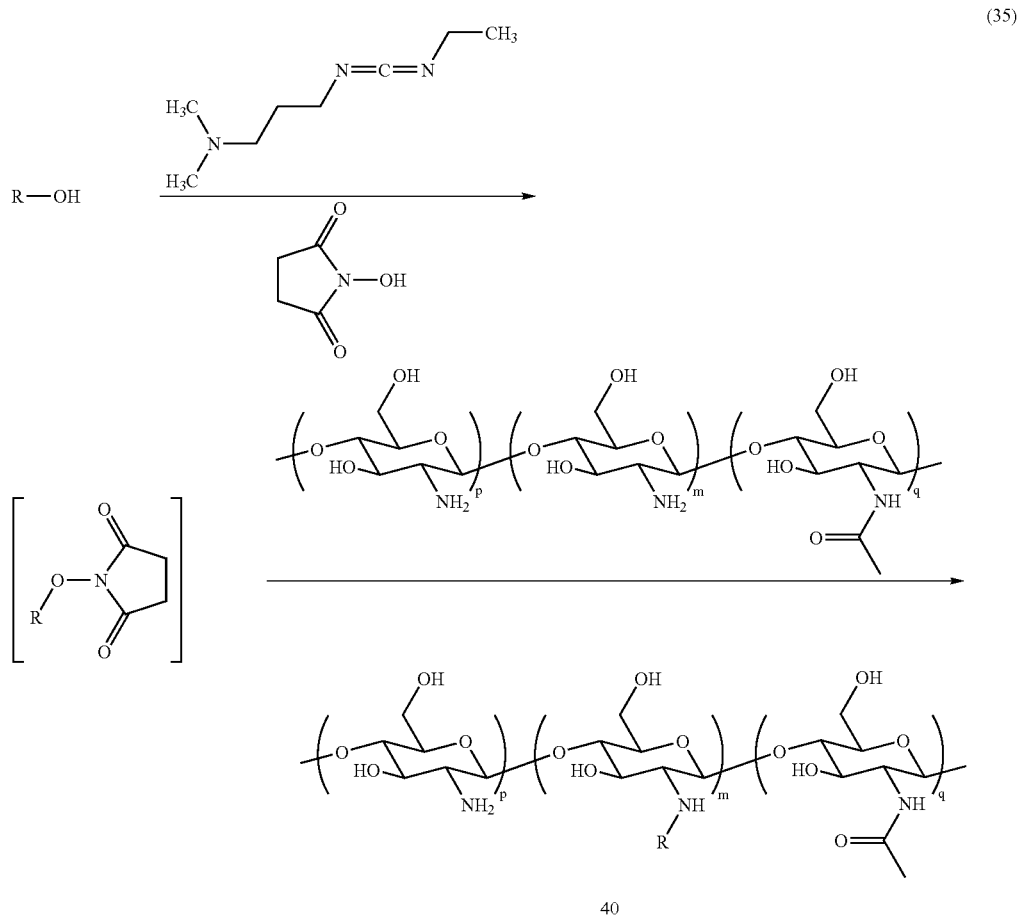

Where R is X, X', X", or X''', as defined above. In accordance with the present invention, selective bacteriocide and/or bacteriostasis is dependent upon molecular weight. Molecular weight of the chitosan-derivative compounds is selected by choice of deprotection time and the molecular weight of the starting chitosan material. In a preferred embodiment, 2 hours of deprotection, at room temperature with constant stirring, is sufficient to remove all of the boc to levels below detectable by NMR. Longer deprotection times, ie exposure to strong acid, result in the continual breakdown of the polymer to produce a distribution of molecular sizes, radius of hydration in solution, relative to the starting material with the longer time resulting in a broader distribution and a lower average molecular size. FIG. 15 shows the shift in radius of hydration shifts from ~28 nm (chitosan) to ~20 nm (CPA12, chitosan-arginine 6%) after 8 hours of deprotection and to ~10 nm (CPA3, chitosan-arginine 6%) after 19 hrs deprotection. This is a preferred embodiment of the present invention where a variety of molecular weights is desired for broad spectrum antibacterial activity.

Molecular weight of the chitosan-derivative compounds of the present invention is selected by pre-fractionation of original chitosan source by dialysis membranes or purchase of a particular molecular weight. In a preferred embodiment for high MW chitosan derivatives, subsequent deprotection is minimized to 2 hours to remove all of the TFA, HCl or similar strong acids. It is important to note that higher molecular weights are maintained at lower deprotection times. Selected narrower ranges of MW are obtained by gel permeation chromatography/size exclusion columns after long deprotection times.

EXAMPLE 16

Synthesis of Chitosan-arginine

The following is an example of the synthesis for a ratio of free amine:boc-arginine:NHS:EDC 1:3:3:3. Chitosan (2.5 g, 0.0127 moles) is dissolved in 190 mL 0.1 M HCl solution by agitation for 30 minutes. In a separate vessel, boc-Arginine-OH (12.54 g, 0.038 moles, 3 equivalents) and N-hydroxysuccinimide (4.39 g, 0.038 equivalents) is dissolved in 200 mL millipore water. After dissolution of arginine and N-hydroxysuccinimide, N-(3-Dimethylaminopropyl)-N'-ethylcarbodiimide (EDC, 6.75 mL, 0.038 equivalents) added and stirred for one minute. This activated solution is then added to the dissolved chitosan solution and agitated overnight at room temperature. This solution is dialysed against 4 L each of solution, 5 steps in 2 days, after the functionalization reaction and after the TFA deprotection where the dialysis conditions are for each step 1) 0.01 M NaCl, 2) 0.01 M NaCl, 3) Millipore ultra pure 18.2MΩ-cm water, 4) Millipore ultra pure 18.2MΩ-cm water, 5) Millipore ultra pure 18.2MΩ-cm water. No pH adjustment is required on the dialyses.

Figure 16:
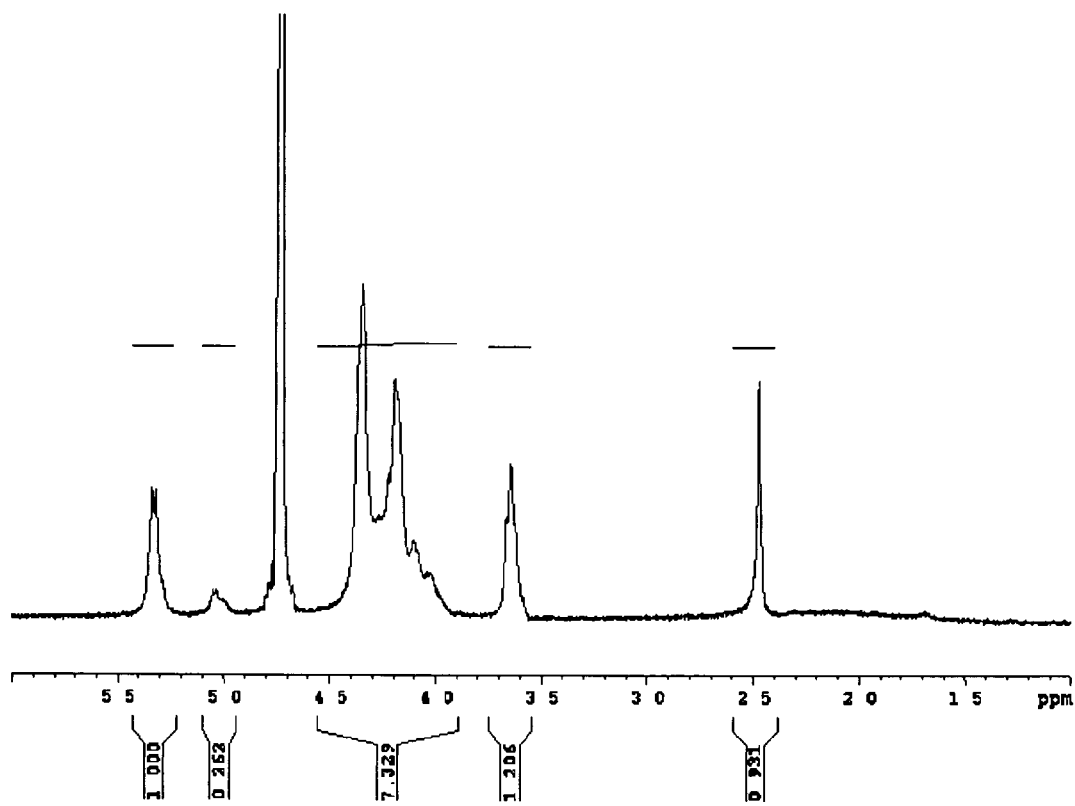
FIG. 16 NMR spectrum of chitosan at 70° C. with water peak suppression.

In accordance with the present invention, the lyophilized product is broadly characterized using a variety of techniques. It is important to determine any residual contaminants, to verify molecular weight and to quantify degree of functionalization. FT-IR spectroscopy is used to verify the absence of residual TFA. While not quantitative as to the degree of functionalization, the IR data is helpful in identifying the presence of the shifted amide bond to easily identify TFA contaminant. As shown in FIG. 16, an NMR spectrum with water suppression at 70° C. is used to assess the degree of deacetylation and any remaining contaminant of the starting material chitosan. For quantification of arginine functionalization, these high temperatures for NMR analysis are not necessary because the chitosan-arginine methylene peaks are located at ~1.8 ppm and 1.3 ppm, regions on the chitosan NMR spectrum demonstrated in FIG. 16 where there is very little proton structure. The water peak is significantly downfield and not obstructive. An NMR spectrum of chitosan-arginine taken at 70° C. with water suppression is shown in way, control of the degree of functionalization, control of the molecular weight and provide the basis for addition of any other carbonic acids as is understood by one of ordinary skill in the art.

The following is a preferred method for synthesizing chitosan-guanidine, in accordance with the present invention:

The chemical coupling of the chitosan amines to a guanidinyl group involves 1H-pyrazole-1-carboxamidine (HPC) and N,N-Diisopropylethylamine (DIEA). HPC and DIEA are used to couple guanidine with the amine on the chitosan and to provide a basic environment for more effective coupling, respectively. The pyrazole is a good, stable leaving group after the nucleophilic amine reacts with the electrophilic carbon of the carboxamidine.

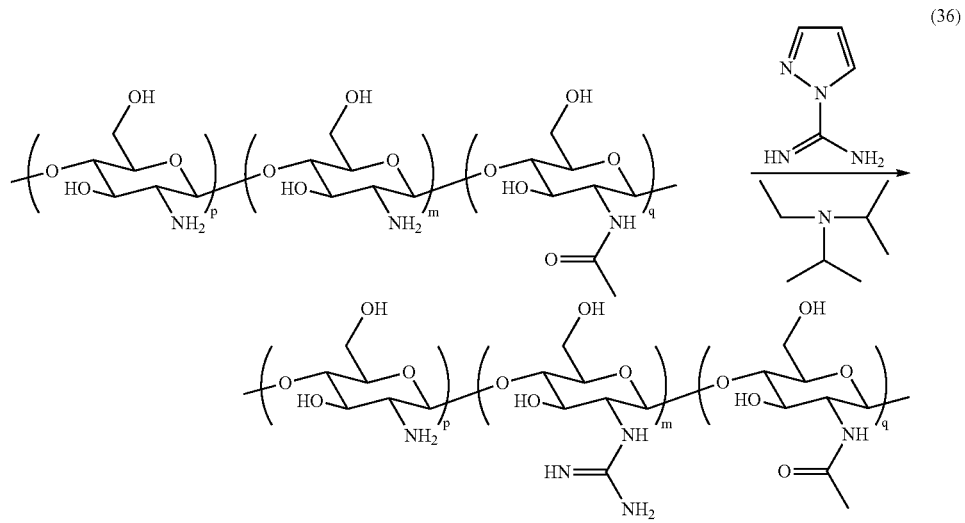

(36)

Figure 17A:
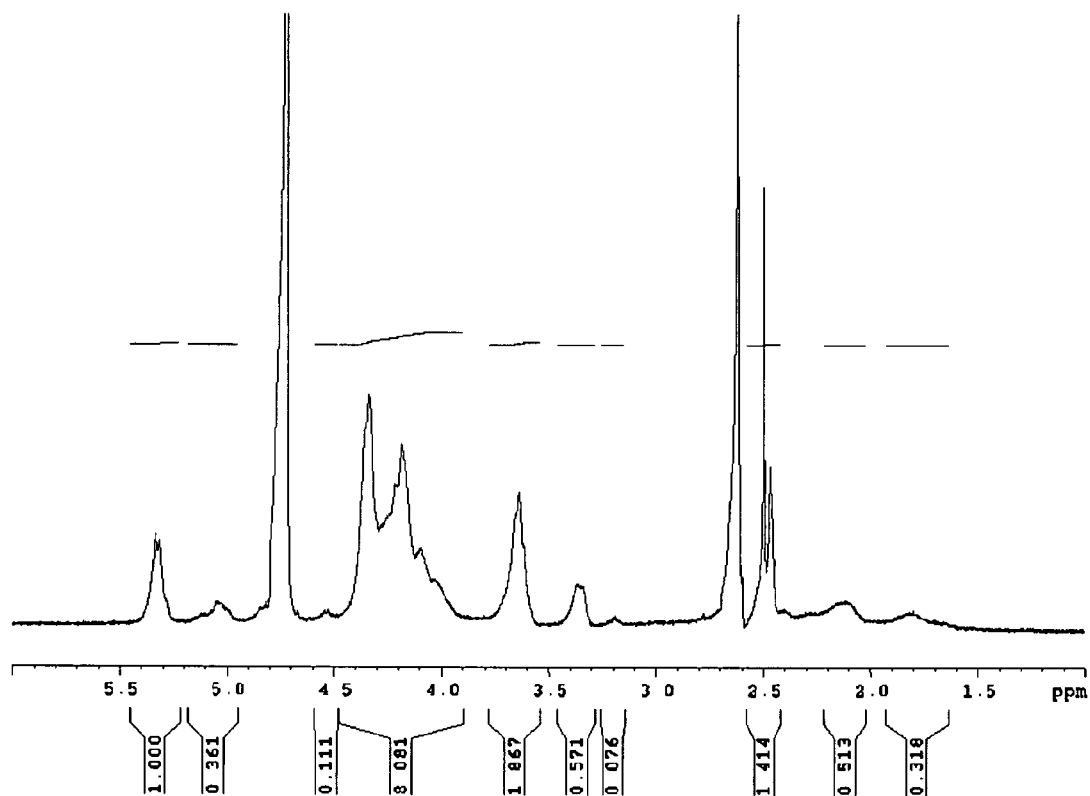
FIG. 17(a) NMR spectrum of chitosan-arginine at 70° C. with water peak suppression.
Figure 17B:
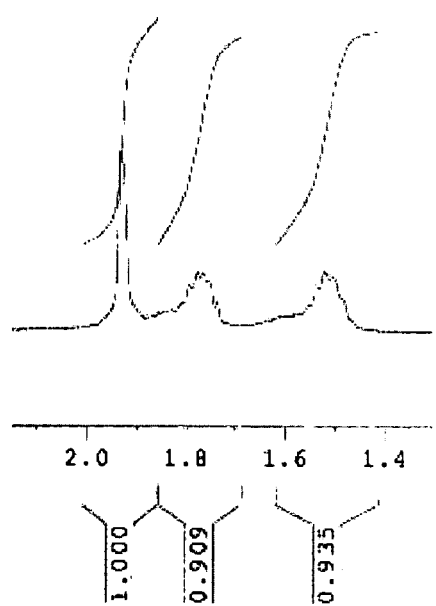
FIG. 17(b) NMR spectrum of chitosan-arginine at room temperature at a limited range between 2.2 and 1.3 ppm.
Figure 18A:
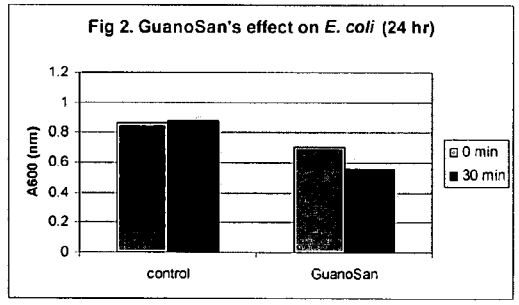
FIG. 18 (a) shows chitosan-guanidine's bacteriocidal effect on *E. coli*.
Figure 18B:
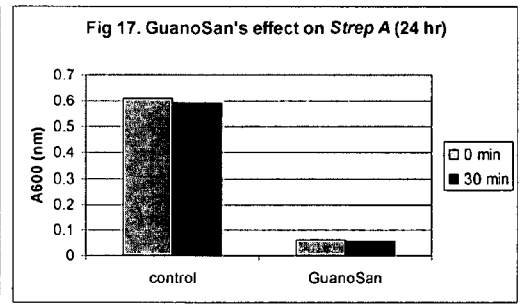
Figure 18C:
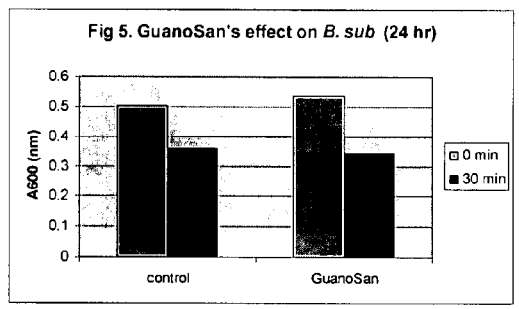
Figure 18D:
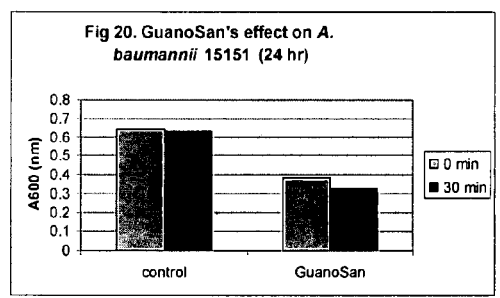
Figure 18E:
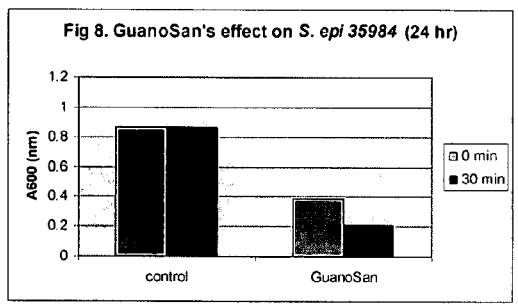
Figure 18E:
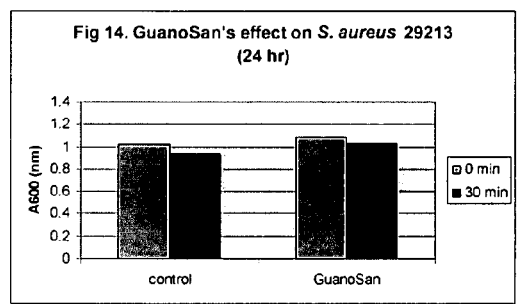
Figure 18G:
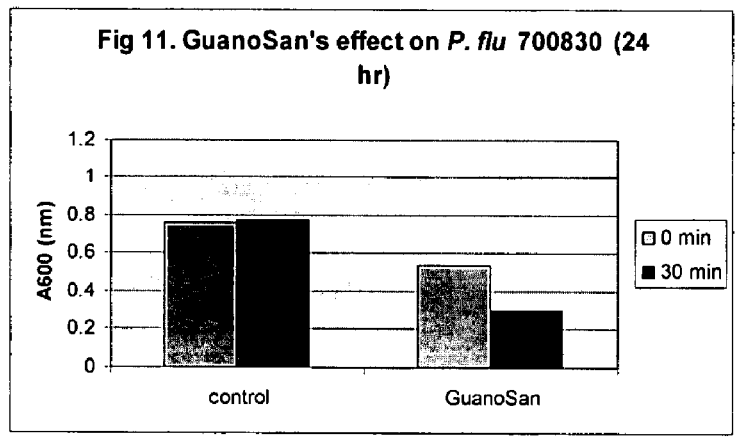
Figure 18H:
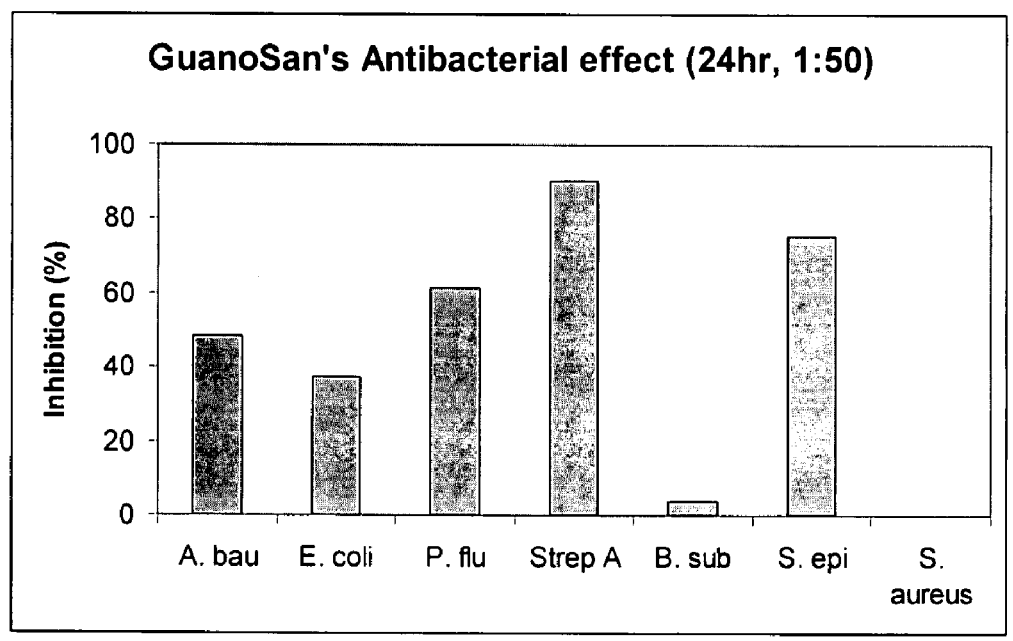

FIG. 17(a). Note the additional peaks at ~2.21 and 1.7 ppm in addition to a number of downfield peaks. These peaks represent the protons on the arginine side chain and move up and downfield depending on the neighboring groups and temperature. FIG. 17(b) shows the limited range of proton peaks between 2.2 and 1.3 ppm. Degree of functionalization is determined using the acetate hydrogens between ~2.0 and 1.9 as the comparison unit. The degree of acetylation is known, and thus the total number of acetates is known. The calculation is conducted by integrating the acetate hydrogens at 1.95 ppm to a normalized value of 1, and comparing each of the integrated arginine peaks (which are nearly identical) at a ratio of 2/3 to give the degree of functionalization relative to the degree of acetylation. For example 16, with 82% deacetylation, the degree of functionalization is 30±5%. The degree of functionalization relative to free amines is reported. A preferred method of arginine functionalization is by combustion analysis for CHN in which the arginine functionalization is directly determined relative to the starting chitosan to better than 1%. Dynamic light scattering is used to determine the size distribution of chitosan-arginine compounds. Multi-angle light scattering with a gradient gel HPLC column (Shodex) or standard column (TSK) is used to determine average molecular weight and molecular weight distributions. *Limulus* ameobate lysate assay (kinetic) is used to determine residual endotoxin levels.

The optimization of the synthesis, according to the present invention, allows for increased control of the synthetic path- A preferred embodiment of the present invention includes a process for coupling a guanidinyl group to chitosan, as shown in (36), above. The coupling process includes dissolving chitosan in water for equal particulate dispersion and dilution in aqueous acidic acid solution (pH ≦5) to produce a soluble starting material. In a separate vessel, the HPC and DIEA are vigorously mixed in water (by shaking). A two-phase solution occurs as the DIEA is insoluble in water. The highly emulsified solution is added to the chitosan solution which results in rapid precipitation of the chitosan. The pH is rapidly brought down to a pH of ~5, or just to the point where the chitosan is again soluble. The pH is maintained at an elevated level with concurrent solubility of the chitosan to assure sufficient availability of active, de-protonated amines for reaction. The formation of a guanidinyl nitrogen requires a nucleophilic amine. It is important to note that reaction efficiency is enhanced by addition of simply equimolar DIEA to the chitosan amines. The final mixture is allowed to react under ambient conditions for up to 20 hours, with vigorous shaking. Note that stirring does not suffice, as the stir bar only interacts with a small volume of the solution due to the high viscosity.

In accordance with the present invention, chitosan-guanidine can be produced by an alternate process. Here, chitosan guanidine is prepared by reacting formamidine sulfonic acid as shown in (38), below, that is prepared in one step from commercial materials, as shown in (37). The conditions necessary for chitosan functionalization are somewhat different than the conditions under which the reagent was originally intended to operate (absolute MeOH, in this case).

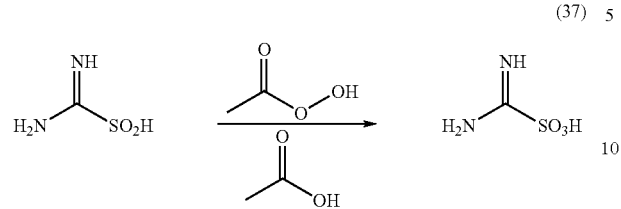

(37)

Guanidinylation reactions are performed as in (38), below with excess sulfonic acid with the unreacted reagent being removed via dialysis. The solution is dialysed against 0.01M NaCl 2× and then against ultrapure Millipore water adjusted to pH 7 3× with a cellulose membrane with a 5 kDa cutoff. The chitosan-guanidine product is then lyophilized.

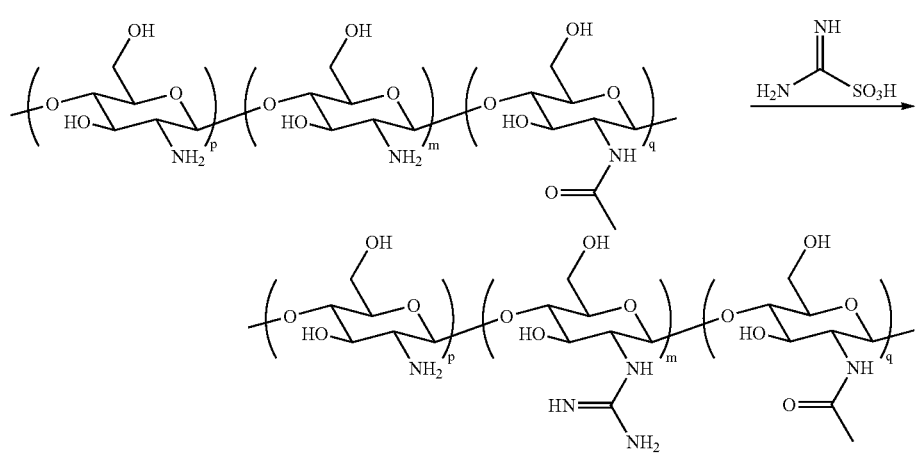

The methodology shown in (36) is the preferred embodiment for the process of guanidinylation of amines of chitosan, of the unnatural amino acids and of the acid-amines described above.

EXAMPLE 17

Synthesis of Chitosan-guanidine

Synthesis of 6% functionalized chitosan guanidine while preserving the initial average molecular weight of chitosan.

Chitosan (1.0 g, 0.005 moles) is added to 15 mL of millipore water. To this solution, 1% acetic acid is added until the chitosan is completely solubilized (30 mL). In a separate vessel 1H-pyrazole-1-carboxamidine (3.66 g, 0.025 moles, 5 equivalents) and N,N-Diisopropylethylamine (4.35 mL, 0.025 moles, 5 equivalents) are mixed in 5 mL millipore water. This biphasic solution is vigorously shaken to provide an emulsion. This emulsified solution is added to the chitosan solution, resulting in chitosan precipitation. The pH of this mixed solution is adjusted with 10% acetic acid until the chitosan dissolves (pH 4-5.5). This solution is shaken overnight at ambient temperature and dialysed as normal. The freeze-dried material is analyzed by combustion analysis for C, N and H content and the degree of functionalization determined to be less than 5%.

What is claimed is:

1. A purified preparation comprising a chitosan-derivative compound of the following formula:

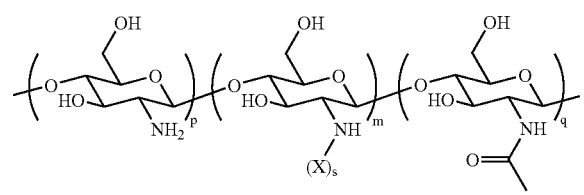

where m is 0.02-0.50; q is 0.50-0.01; s is 1; p+q+m=1; the percentage degree of functionalization is m/(1−q) ·100%; and X is selected from the group consisting of:

(38)

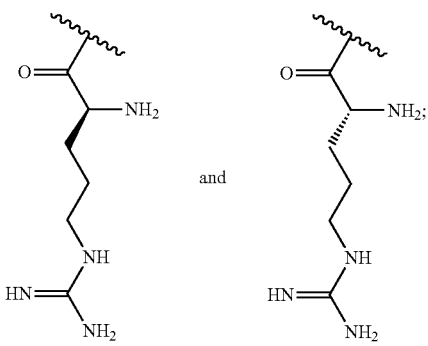

wherein the preparation is substantially free of compounds having a molecular weight of less than 5000 Da, and wherein the preparation is substantially free of polyarginine polymers.

2. The preparation as recited in claim 1, wherein the compound comprises the following properties: a molecular weight between 25,000 and 350,000 Da, solubility at pH between 6.8 and 7.4, wherein said q is at least 0.20 and said functionalization is between 6% and 30%.

3. A purified preparation comprising a compound of the following formula:

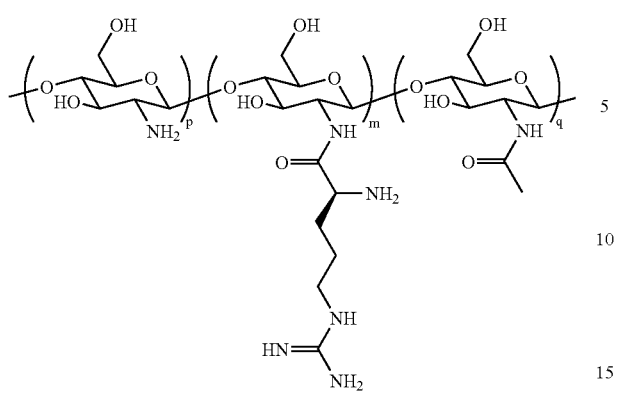

where m is 0.02-0.50; q is 0.50-0.01; p+q+m=1 and percentage degree of functionalization is m/(1−q) ·100%; wherein the preparation is substantially free of compounds having a molecular weight of less than 5000 Da, and wherein the preparation is substantially free of polyarginine polymers.

4. The preparation as recited in claim 3, wherein the compound comprises the following properties: a molecular weight between 25,000 and 350,000 Da, solubility at pH between 6.8 and 7.4, wherein said q is at least 0.20 and said functionalization is between 6% and 30%.

5. A purified preparation comprising a chitosan-derivative compound of the following formula:

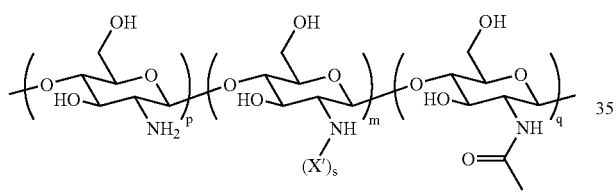

where m is 0.02-0.50; q is 0.50-0.01; s=1; p+q+m=1; and X' is selected from the group consisting of:

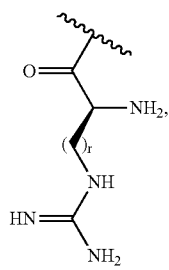 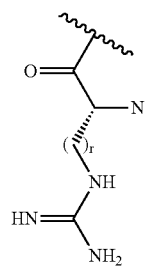 and

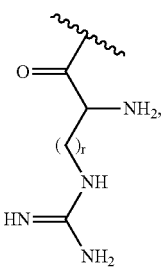

where r is 1–6;
wherein the preparation is substantially free of compounds having a molecular weight of less than 5000 Da, and wherein the preparation is substantially free of polyarginine polymers.

6. A purified preparation comprising a chitosan-derivative compound of the following formula:

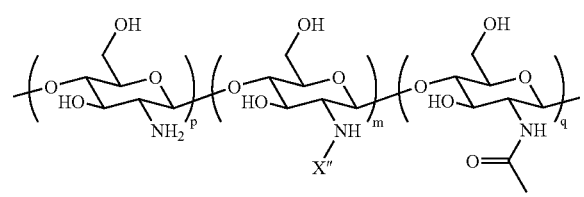

where m is 0.02-0.50; q is 0.50-0.01; p+q+m=1; and X″ is:

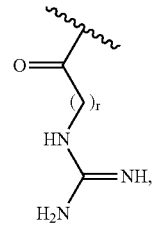

where r is 1–6.

7. A purified composition comprising chitosan-derivative compound of the following formula:

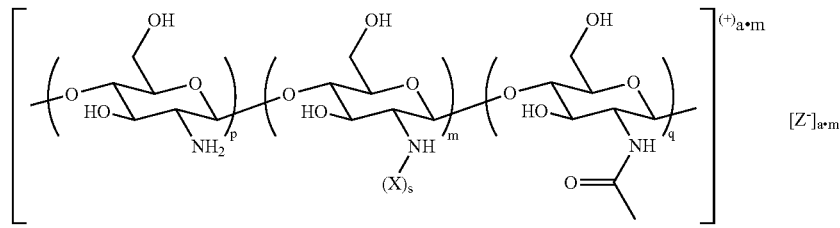

| 61 | 62 |

Where a=1; m is 0.02-0.50; q is 0.50-0.01; s=1; p+q+m=1; Z is a counterion; and X is selected from the group consisting of:

where a=1; m is 0.02-0.50; q is 0.50-0.01; s=1; p+q+m=1; Z is a counterion; and X' is selected from the group consisting of:

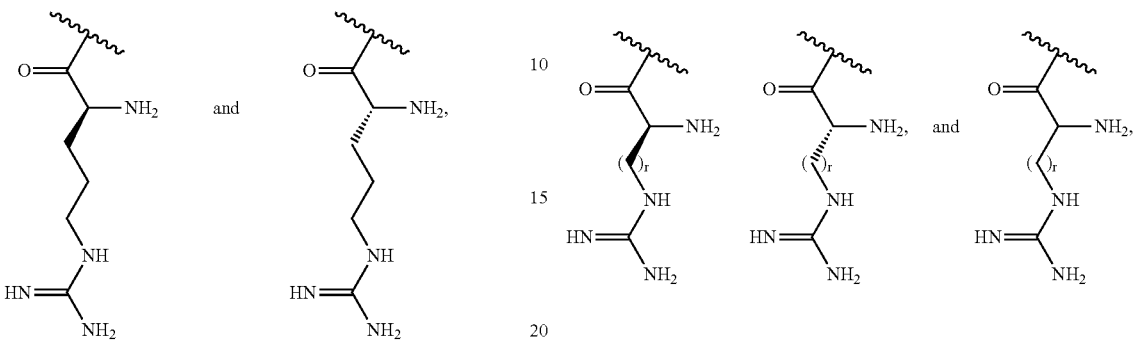

wherein the guanidine moiety is positively charged;
wherein the preparation is substantially free of compounds having a molecular weight of less than 5000 Da, and wherein the preparation is substantially free of polyarginine polymers.

8. The preparation as recited in claim 7, wherein Z is selected from the group consisting of chloride, hydroxide, phosphate, carbonate, acetate, lactate, citrate, cinnamate, oxalate, and glutamate.

9. A purified preparation comprising a chitosan-derivative compound of the following formula:

where r is 1–6, and wherein the guanidine moiety is positively charged;
wherein the preparation is substantially free of compounds having a molecular weight of less than 5000 Da, and wherein the preparation is substantially free of polyarginine polymers.

10. The preparation as recited in claim 9, wherein Z selected from a group consisting of:
chloride, hydroxide, phosphate, carbonate, acetate, lactate, citrate, cinnamate, oxalate, and glutamate.

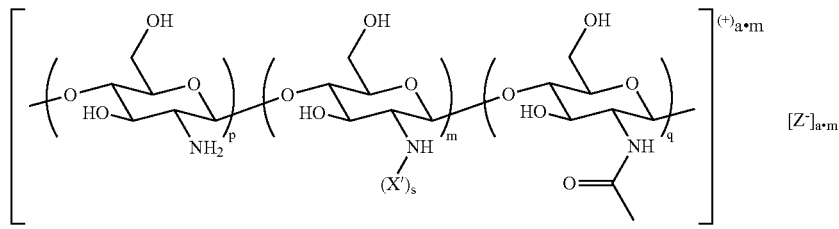

11. A purified preparation comprising a chitosan-derivative compound of the following formula:

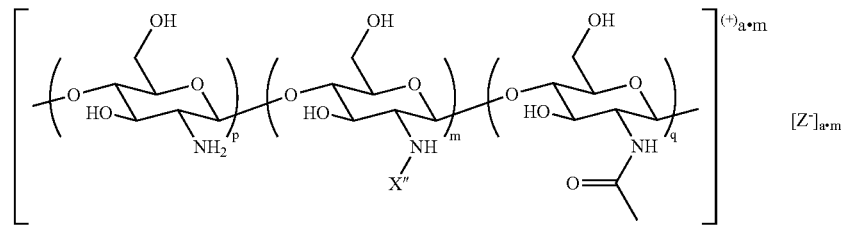

where a=1; m is 0.02-0.50; q is 0.50-0.01; p+q+m=1; Z is a counterion; and X" is:
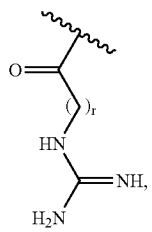
where r is 1–6, and wherein the guanidine moiety is positively charged.
12. A preparation as recited in claim 11, wherein Z is selected from a group consisting of:
chloride, hydroxide, phosphate, carbonate, acetate, lactate, citrate, cinnamate, oxalate, and glutamate.
* * * * *